US006888143B2

(12) United States Patent
Vogt et al.

(10) Patent No.: US 6,888,143 B2
(45) Date of Patent: May 3, 2005

(54) APPARATUS AND METHOD FOR INSPECTING PRE-FASTENED ARTICLES

(75) Inventors: Brian R. Vogt, Oshkosh, WI (US); Henry L. Carbone, II, St. Paul, MN (US); Clinton D. Clark, Menasha, WI (US); Jack Couillard, Menasha, WI (US); Tim G. Dollevoet, Kimberly, WI (US); Joseph J. Gimenez, Appleton, WI (US); Matthew L. Koele, Chilton, WI (US); Kurt G. Krupka, Hortonville, WI (US); Bradley M. Marohl, Neenah, WI (US); David A. Maxton, Appleton, WI (US); Archie D. Morgan, Neenah, WI (US); Robert L. Popp, Hortonville, WI (US); Michael W. Protheroe, Neenah, WI (US); Steven L. Schnasse, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 28 days.

(21) Appl. No.: 10/209,751

(22) Filed: Jul. 31, 2002

(65) Prior Publication Data

US 2003/0168614 A1 Sep. 11, 2003

Related U.S. Application Data

(60) Provisional application No. 60/362,833, filed on Mar. 9, 2002, provisional application No. 60/372,866, filed on Mar. 9, 2002, provisional application No. 60/364,264, filed on Mar. 14, 2002, provisional application No. 60/364,329, filed on Mar. 14, 2002, and provisional application No. 60/382,812, filed on May 23, 2002.

(51) Int. Cl.[7] .................................................. G01J 5/02
(52) U.S. Cl. ................................ 250/341.1; 250/341.6; 250/341.8
(58) Field of Search ........................... 250/341.1, 341.6, 250/341.8

(56) References Cited

U.S. PATENT DOCUMENTS

| 2,935,559 | A | 5/1960 | Domier |
| 2,984,699 | A | 5/1961 | Domier |

(Continued)

FOREIGN PATENT DOCUMENTS

| EP | 0 043 723 A2 | 1/1982 |
| EP | 0 217 032 A2 | 7/1986 |

(Continued)

OTHER PUBLICATIONS

International Search Report, PCT/US 03/06148, from European Patent Office dated Aug. 8, 2003.
International Search Report, PCT/US 03/06074 dated Aug. 13, 2003, 4 pages.
International Search Report, PCT/US 03/06128, from the European Patent Office dated Aug. 1, 2003.
International Search Report for PCT/US 03/06073 dated Jul. 2, 2003.

Primary Examiner—Constantine Hannaher
Assistant Examiner—Shun Lee
(74) Attorney, Agent, or Firm—Senniger Powers

(57) ABSTRACT

In a method and apparatus for making and inspecting pre-fastened articles, such as disposable training pants, having at least two generally flexible elements capable of connection with each other during initial assembly of the article, the elements are arranged in overlapping relationship with each other and connected together to define an engagement seam of the article. The article is arranged to define an interior space thereof whereby the interior space is bounded in part by the engagement seam. The elements are irradiated at the engagement seam by a radiation source within the interior space of the article and an image of the irradiated engagement seam is captured by an image capturing device. In one embodiment, the image capturing device is positioned within the interior space of the article and the radiation source is either within the interior space or exterior of the article.

143 Claims, 28 Drawing Sheets

U.S. PATENT DOCUMENTS

| | | | |
|---|---|---|---|
| 3,711,176 | A | 1/1973 | Turner, Jr. et al. |
| 4,166,541 | A | 9/1979 | Smith, Jr. |
| 4,170,419 | A | 10/1979 | Van Tyne et al. |
| 4,543,141 | A | 9/1985 | Bradley et al. |
| 4,614,969 | A | 9/1986 | Gerundt et al. |
| 4,663,220 | A | 5/1987 | Wisneski et al. |
| 4,680,205 | A | 7/1987 | Lerner et al. |
| 4,685,475 | A | 8/1987 | Ridler et al. |
| 4,704,116 | A | 11/1987 | Enloe |
| 4,806,776 | A | 2/1989 | Kley |
| 4,811,002 | A | 3/1989 | Otsubo |
| 4,837,715 | A | 6/1989 | Ungpiyakul et al. |
| 4,877,940 | A | 10/1989 | Bangs et al. |
| 4,900,384 | A | 2/1990 | Sanders et al. |
| 4,940,464 | A | 7/1990 | Van Gompel et al. |
| 4,972,093 | A | 11/1990 | Cochran et al. |
| 4,982,103 | A | 1/1991 | Meiffren et al. |
| 5,045,135 | A | 9/1991 | Meissner et al. |
| 5,046,272 | A | 9/1991 | Vogt et al. |
| 5,103,337 | A | 4/1992 | Schrenk et al. |
| 5,104,116 | A | 4/1992 | Pohjola |
| 5,110,403 | A | 5/1992 | Ehlert et al. |
| 5,166,536 | A | 11/1992 | Rye |
| 5,182,722 | A | 1/1993 | Hain |
| 5,204,538 | A | 4/1993 | Genovese |
| 5,224,405 | A | 7/1993 | Pohjola |
| 5,226,992 | A | 7/1993 | Morman |
| 5,235,515 | A | 8/1993 | Ungpiyakul et al. |
| 5,246,433 | A | 9/1993 | Hasse et al. |
| 5,286,543 | A | 2/1994 | Ungpiyakul et al. |
| 5,343,049 | A | 8/1994 | Vareille et al. |
| 5,347,135 | A | 9/1994 | Harris et al. |
| 5,359,525 | A | 10/1994 | Weyenberg |
| 5,399,016 | A | 3/1995 | Martin |
| 5,483,893 | A | 1/1996 | Issac et al. |
| 5,500,063 | A | 3/1996 | Jessup |
| 5,547,531 | A | 8/1996 | Allen et al. |
| 5,549,537 | A | 8/1996 | Focke et al. |
| 5,552,007 | A | 9/1996 | Rajala et al. |
| 5,626,711 | A | 5/1997 | Herrmann |
| 5,635,724 | A | 6/1997 | Higgins |
| 5,637,864 | A | 6/1997 | Nicks et al. |
| 5,644,140 | A | 7/1997 | Biedermann et al. |
| 5,660,666 | A | 8/1997 | Dilnik et al. |
| 5,663,565 | A | 9/1997 | Taylor |
| 5,726,758 | A | 3/1998 | Hasegawa et al. |
| 5,755,902 | A | 5/1998 | Reynolds |
| 5,766,389 | A | 6/1998 | Brandon et al. |
| 5,772,825 | A | 6/1998 | Schmitz |
| 5,779,831 | A | 7/1998 | Schmitz |
| 5,818,719 | A | 10/1998 | Brandon et al. |
| 5,855,574 | A | 1/1999 | Kling et al. |
| 5,858,515 | A | 1/1999 | Stokes et al. |
| 5,870,203 | A | 2/1999 | Chiu et al. |
| 5,879,500 | A | 3/1999 | Herrrin et al. |
| 5,930,139 | A | 7/1999 | Chapdelaine et al. |
| 5,980,087 | A | 11/1999 | Brandon et al. |
| 6,040,903 | A | 3/2000 | Lysen et al. |
| 6,067,155 | A | 5/2000 | Ringlien |
| 6,082,732 | A | 7/2000 | Hutchison et al. |
| 6,092,002 | A | 7/2000 | Kastman et al. |
| 6,166,393 | A | 12/2000 | Paul et al. |
| 6,198,102 | B1 | 3/2001 | Shepherd |
| 6,217,794 | B1 | 4/2001 | Neal et al. |
| 6,224,699 | B1 | 5/2001 | Bett et al. |
| 6,245,168 | B1 | 6/2001 | Coenen et al. |
| 6,253,159 | B1 | 6/2001 | Bett et al. |
| 6,259,526 | B1 | 7/2001 | Pace et al. |
| 6,270,599 | B1 | 8/2001 | Wood |
| 6,323,954 | B1 | 11/2001 | Halter |
| 6,352,497 | B1 | 3/2002 | Hensley et al. |
| 6,444,064 | B1 | 9/2002 | Henry et al. |
| 6,652,686 | B1 * | 11/2003 | Coenen et al. ............... 156/64 |
| 2001/0016059 | A1 | 8/2001 | Krahn et al. |
| 2002/0000291 | A1 | 1/2002 | Coenen et al. |
| 2002/0055430 | A1 | 5/2002 | Coenen et al. |

FOREIGN PATENT DOCUMENTS

| | | |
|---|---|---|
| EP | 0 217 032 A3 | 8/1987 |
| EP | 0 217 032 B1 | 8/1987 |
| EP | 0 320 991 A2 | 6/1989 |
| EP | 0 328 890 A1 | 8/1989 |
| EP | 0 554 911 A1 | 8/1993 |
| WO | WO96/17303 A1 | 6/1996 |
| WO | WO96/19346 A3 | 6/1996 |
| WO | WO96/19346 A2 | 6/1996 |
| WO | WO96/19347 A3 | 6/1996 |
| WO | WO96/19347 A2 | 6/1996 |
| WO | WO99/36809 A1 | 7/1999 |
| WO | WO99/36810 A1 | 7/1999 |
| WO | WO00/37009 A2 | 6/2000 |
| WO | WO00/40196 A1 | 7/2000 |
| WO | WO00/45767 A1 | 8/2000 |
| WO | WO01/83347 A1 | 11/2001 |
| WO | WO01/87210 A1 | 11/2001 |
| WO | WO01/87211 A3 | 11/2001 |
| WO | WO01/87211 A2 | 11/2001 |
| WO | WO01/87218 A2 | 11/2001 |
| WO | WO01/87562 A2 | 11/2001 |
| WO | WO01/87753 A3 | 11/2001 |
| WO | WO01/87753 A2 | 11/2001 |

* cited by examiner

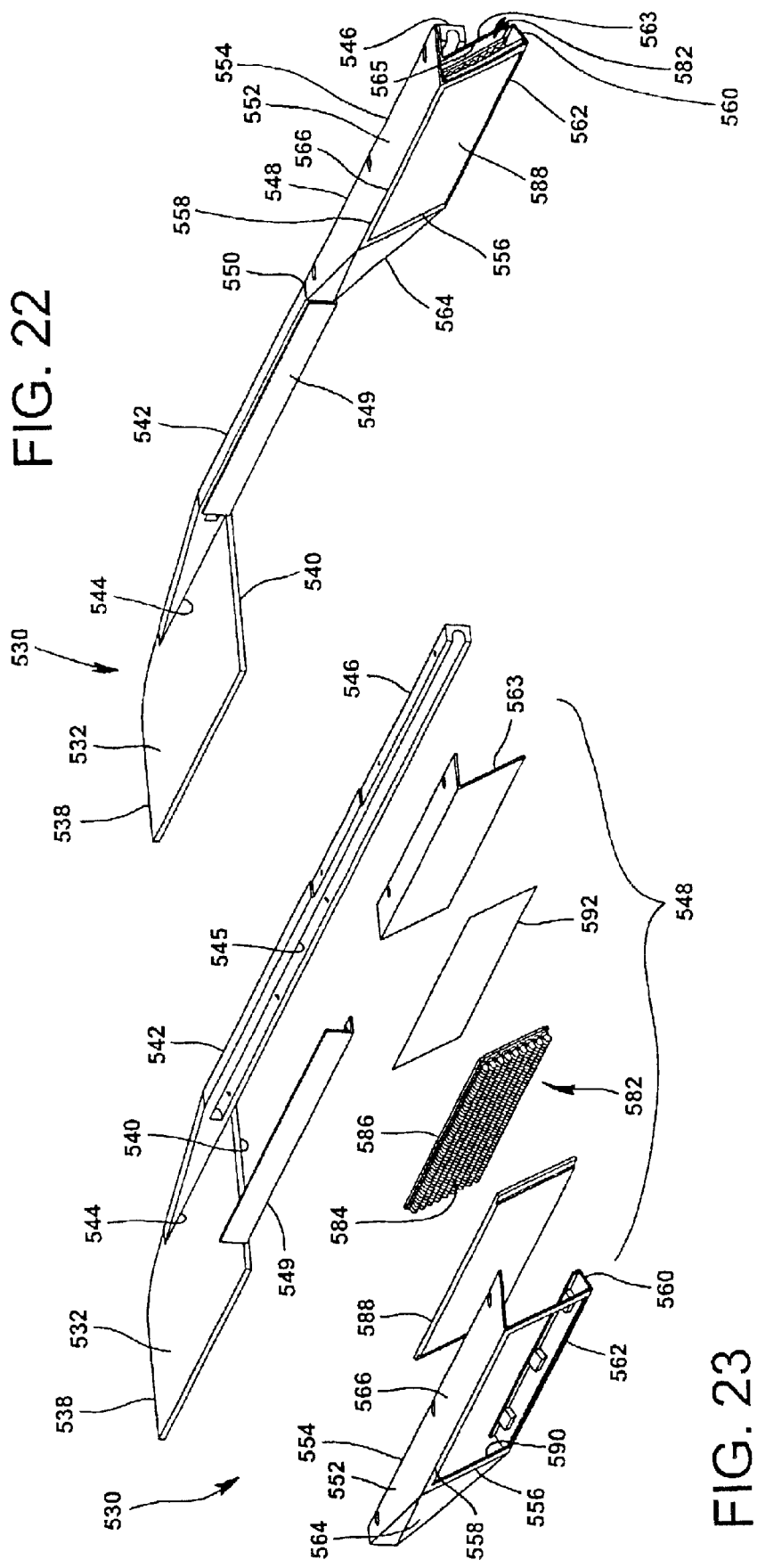

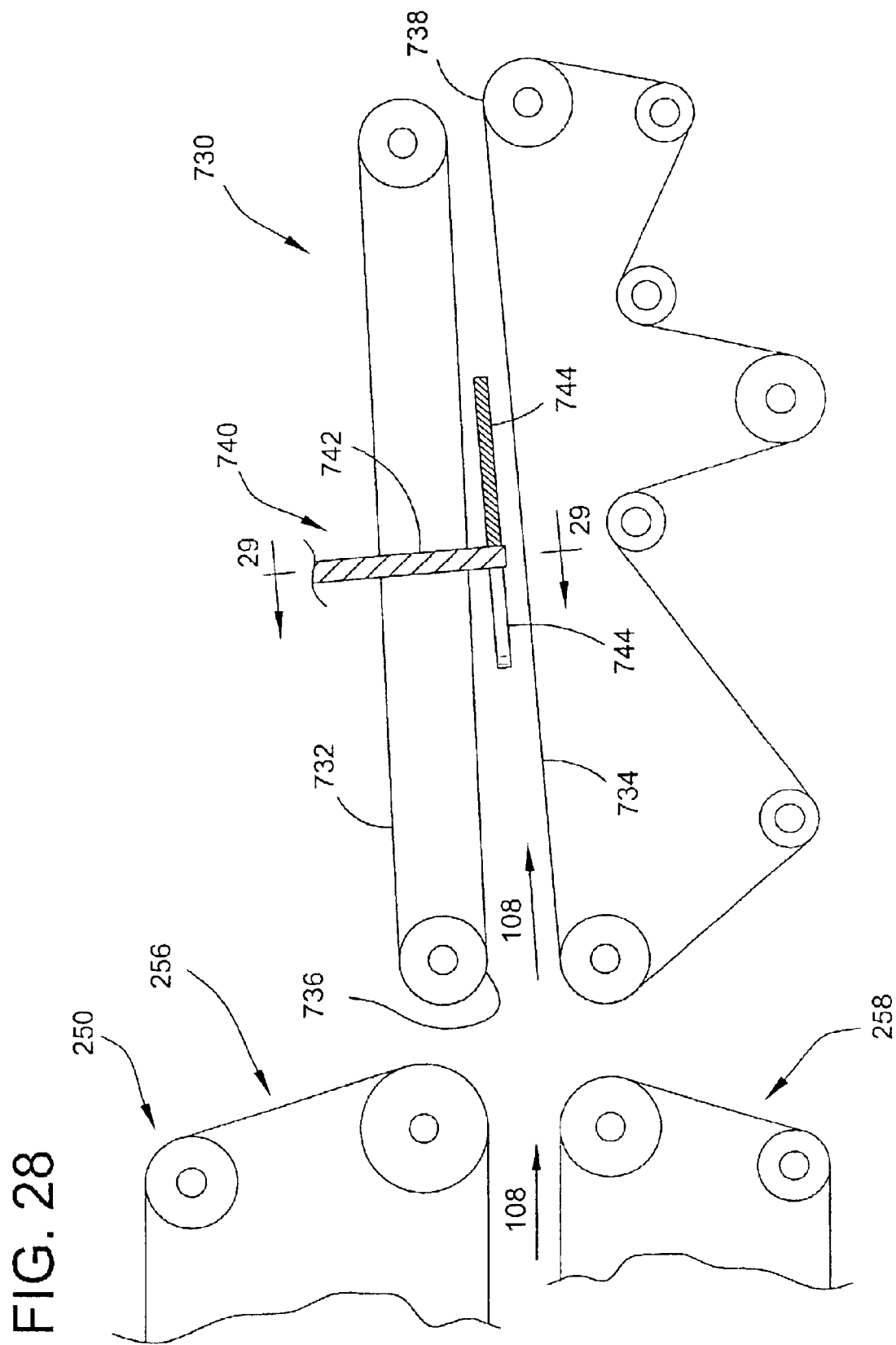

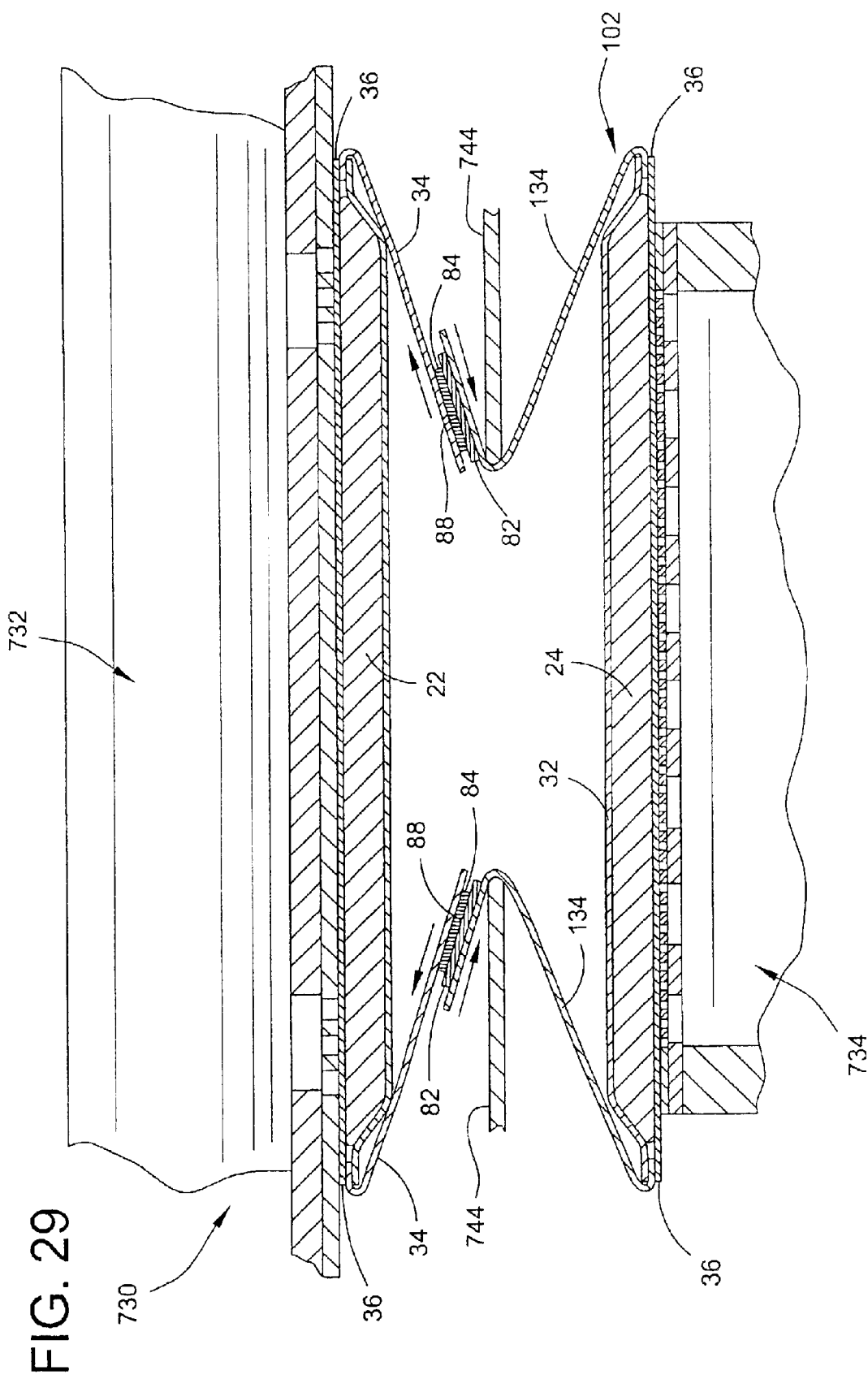

APPARATUS AND METHOD FOR INSPECTING PRE-FASTENED ARTICLES

This application claims the benefit of provisional application Ser. No. 60/362,533. filed Mar. 9, 2002, provisional application Ser. No. 60/372,866, filed Mar. 9, 2002, provisional application Ser. No. 60/364,264, filed Mar. 14, 2002, provisional application Ser. No. 60/364,329 filed Mar. 14, 2002, and provisional application Ser. No. 60/302,812, filed May 23, 2002, all of which are hereby incorporated by reference an their entirety for all purposes.

BACKGROUND OF THE INVENTION

The present invention relates generally to apparatus and methods for making and inspecting pre-assembled or pre-fastened articles, and more particularly to apparatus and methods for connecting two elements of such articles to define an engagement seam and for inspecting the engagement seam of such articles.

Articles such as disposable absorbent garments have numerous applications including diapers, training pants, feminine care products, medical garments and adult incontinence products. A typical disposable absorbent garment is formed as a composite structure including an absorbent assembly disposed between a liquid permeable bodyside liner and a liquid impermeable outer cover. These components can be combined with other materials and features such as elastic materials and containment structures to form a product which is specifically suited to its intended purposes. A number of such garments include fastening components which are intended to be connected together (e.g., pre-fastened) during manufacture of the garment so that the product is packaged in it's fully assembled form.

For example, one such pre-fastened garment is a child's training pants, which has a central absorbent chassis and front and back side panels extending laterally out from the chassis adjacent longitudinally opposite ends thereof. A portion of each of the front and back side panels has a respective fastening component disposed thereon. During manufacture of the training pants, the central absorbent chassis is initially formed generally flat and then folded over so that the front and back side panels face each other. The respective fastening components of the front and back side panels are then aligned and connected together to define an engagement seam. Upon securing the front and back side panel fastening components together, the pre-fastened pair of training pants is in its fully assembled three-dimensional form having an interior space bounded in part by the engagement seam.

For quality control purposes, it is often desirable to monitor the presence of and/or interrelationships between one or more elements of a disposable absorbent garment. For instance, elements such as outer covers, liners, absorbent pads, side panels, elastic components, fastener components, etc. must be positioned or aligned with respect to each other and/or to other components as desired or otherwise intended in order to produce an acceptable product. Accordingly, inspection systems are commonly used to detect the presence and/or relative positions of such components during manufacturing. If an inspection system determines that one or more components are out of position and thus do not properly register with other components, the inspection system typically outputs one or more signals indicating that certain articles should be culled and discarded, that the process should be adjusted so as to bring out-of-position components into proper position, that the process should be adjusted so that subsequent components are brought into proper registration with one another, etc.

One such registration inspection system is disclosed in U.S. Pat. No. 5,359,525, the entire disclosure of which is incorporated herein by reference. As described therein, registration inspection of a composite product during fabrication is accomplished by producing an image of the article and then analyzing the image to detect the relative positions of one or more components. The detected positions are then compared to desired positions to thereby determine whether one or more components are improperly positioned. This registration inspection system employs conventional video cameras for capturing visible and/or ultraviolet light reflected by and/or transmitted through components of the product in order to produce still video images of such components. Thus, after producing a video image of a composite article and its several components, the image can be analyzed to determine whether the components are properly positioned and registered with one another.

Although highly useful for many applications, the inspection system disclosed in the aforementioned patent has certain shortcomings with respect to the inspection of engagement seams formed by connecting two elements together such that the engagement seam is essentially two layers. For example, engagement seams formed by connected side panels of the training pants described previously has heretofore entailed connecting the side panels in face-to-face relationships with outer edges of the side panels aligned with each other. To inspect such an engagement seam, it was necessary only to inspect the exposed outer edges of the side panels so that there was no need to actually capture an image of any underlying elements or edges of the training pants.

However, more recent engagement seams are formed by connecting the side panels in overlapping relationship so that the outer edge of one side panel underlies the other side panel at the engagement seam. For inspection purposes, it is desirable to capture an image of the underlying panel at the engagement seam to determine the position and relative alignment of the outer edge of the underlying panel. Because the light emitting source and camera of the inspection system described in U.S. Pat. No. 5,359,525 are positioned exterior of the inspected component, it is ill-equipped to inspect the outer edge of an underlying panel of the more recent engagement seams once the panels are connected. For example, it is difficult to lay the engagement seam flat over the light emitting source of the disclosed inspection system, thereby increasing the risk that the image captured by the camera will appear fuzzy. It is also difficult for the visible or ultraviolet light to pass through or reflect from the underlying layer of the multiple layers present at such an engagement seam.

Moreover, it may be desirable to capture an image from both sides of the engagement seam, or at least from the interior space of the pants, so that the camera has to look through fewer layers of material to capture an image of the underlying panel at the engagement seam. However, because of the three dimensional configuration of disposable articles such as training pants following formation of the engagement seam (e.g., having a generally closed cross-section parallel to the transverse axis of the pants) the light emitting source and camera have heretofore been located only on the outside of the pants (e.g., in opposed relationship with the overlapping component of the lap seam) to avoid obstructing the movement of training pants through the manufacturing apparatus.

SUMMARY OF THE INVENTION

In general, one method of the present invention for making a pre-fastened article having at least two generally flexible elements capable of connection with each other during initial assembly of the article to at least partially form said pre-fastened article comprises arranging a portion of one of the generally flexible elements in overlapping relationship with a portion of the other element and connecting the element portions together to define an engagement seam of the article. The article is arranged to define an interior space thereof whereby the interior space is bounded in part by the engagement seam. The elements are irradiated at the engagement seam from within the interior space of the article and an image of the irradiated engagement seam is captured.

Another method for making a pre-fastened article having at least two generally flexible elements capable of connection with each other during initial assembly of the article to at least partially form said pre-fastened article generally comprises arranging a portion of one of the generally flexible elements in overlapping relationship with a portion of the other element and connecting the element portions together to define an engagement seam of the article. The article is arranged to define an interior space thereof whereby the interior space is bounded in part by the engagement seam. The elements are irradiated at the engagement seam and an image of the irradiated engagement seam is captured from generally within the interior space of the article.

One method of the present invention for inspecting an engagement seam of pre-fastened disposable pants generally comprises irradiating front and back side panels of the pants at the engagement seam thereof from generally within an interior space of the pants and capturing an image of the irradiated engagement seam.

Another method for inspecting an engagement seam of pre-fastened disposable pants generally comprises irradiating front and back side panels of the pants at an engagement seam thereof and capturing an image of the irradiated engagement seam from generally within an interior space of the pants.

In general, one method of the present invention for making pre-fastened disposable pants comprises arranging front and back side panels of the pants relative to each other such that connectable portions of the front and back side panels are in at least partially opposed relationship with each other. The side panel portions are connected together to define an engagement seam. At least a portion of the pants is expanded to tension the front and back side panels generally at the engagement seam and the engagement seam is inspected while the portion of the pants is expanded.

One embodiment of apparatus of the present invention for making a pre-fastened article comprising two generally flexible elements capable of connection with each other to assemble the generally comprises a seaming section adapted to connect the elements in overlapping relationship with each other to define an engagement seam and to configure the article so as to define an interior space thereof whereby the interior space is bounded in part by the engagement seam. An inspection system is provided for inspecting the engagement seam and comprises a source of radiation operable to emit radiation generally within the interior space of the article toward the engagement seam for irradiating the elements at the engagement seam. The inspection system also comprises an image capturing device adapted to capture an image of the irradiated engagement seam.

In another embodiment the apparatus for making a pre-fastened article generally comprises a seaming section adapted to connect the flexible elements in overlapping relationship with each other to define an engagement seam and to configure the article so as to define an interior space thereof whereby the interior space is bounded in part by the engagement seam. An inspection system is provided for inspecting the engagement seam and comprises a source of radiation adapted to irradiate the engagement seam. The inspection system also comprises an image capturing device operable to capture an image of the irradiated engagement seam generally from within the interior space of the article.

One apparatus of the present invention for making pre-fastened disposable pants generally comprises a seaming section adapted to connect the side panels in overlapping relationship with each other upon movement of the pants in the machine direction to define an engagement seam and to configure the pants so as to define an interior space thereof whereby the interior space is bounded in part by the engagement seam. An inspection system is provided for inspecting the engagement seam and comprises a source of radiation operable to emit radiation generally within the interior space of said pants toward the engagement seam for irradiating said engagement seam. The inspection system also comprises a support member, and an image capturing device adapted to capture an image of the irradiated engagement seam.

In another embodiment, the apparatus for making pre-fastened disposable pants generally comprises a seaming section adapted to connect the side panels in overlapping relationship with each other upon movement of the pants in the machine direction to define an engagement seam and to configure the pants so as to define an interior space thereof whereby the interior space is bounded in part by the engagement seam. An inspection system is provided for inspecting the engagement seam and comprises a support member for supporting the side panels at the engagement seam generally within the interior of the pants. The inspection system also comprises a source of radiation operable to irradiate said side panels at the engagement seam upon tensioning thereof, and an image capturing device operable to capture an image of the irradiated engagement seam.

In general, one embodiment of an inspection system of the present invention for inspecting an engagement seam of pre-fastened pants generally comprises a support member adapted for configuring the pants to define an interior space thereof bounded in part by the front and back side panels at the engagement seam. The support member is further configured to generally expand the pants to tension the side panels at the engagement seam. A source of radiation irradiates the side panels at the engagement seam and an image capturing device captures an image of the irradiated engagement seam.

In general, another embodiment of a method for making a pre-fastened article having at least two generally flexible elements capable of connection with each other during initial assembly of the article to at least partially form the pre-fastened article generally comprises arranging a portion of one of the generally flexible elements in overlapping relationship with a portion of the other element. The element portions are connected together to define an engagement seam of said article. The article is arranged to define an interior space thereof whereby the interior space is bounded in part by the engagement seam. The elements are urged at the engagement seam to lay generally flat on a source of radiation and radiation is emitted from the radiation source toward the engagement seam to irradiate the elements at the engagement seam. An image of the irradiated engagement seam is then captured.

Another embodiment of apparatus for making a pre-fastened article generally comprises a seaming section adapted to connect the elements in overlapping relationship with each other to define an engagement seam and to configure the article so as to define an interior space thereof whereby the interior space is bounded in part by the engagement seam.

An inspection system is provided for inspecting the engagement seam and comprises a source of radiation operable to emit radiation toward the engagement seam for irradiating the elements at the engagement seam. A fluid delivery device directs pressurized fluid to impact at least one of the elements generally at the engagement seam whereby the pressurized fluid urges the engagement seam to lay generally flat over the radiation source. An image capturing device is adapted to capture an image of the irradiated engagement seam.

Another embodiment of a method for making prefastened disposable pants generally comprises assembling the pants in a generally unfolded configuration with the front and back side panels disconnected from each other. The pants are folded on a foldline extending laterally through the crotch region of the absorbent chassis such that the front waist region is in at least partially opposed relationship with the back waist region and the front side panel is in at least partially opposed relationship with the back side panel. The side panel portions are connected together to define an engagement seam and the engagement seam is inspected. At least a portion of the front and back side panels at the engagement seam is tucked between the at least partially opposed front and back waist regions of the absorbent chassis.

Definitions

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning. The longitudinal axis lies in the plane of the garment and is generally parallel to a vertical plane that bisects a standing wearer into left and right body halves when the article is worn. The transverse axis lies in the plane of the article generally perpendicular to the longitudinal axis. The garment as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

FIG. 22 is a perspective of a portion of an inspection system of apparatus for making articles such as training pants;

FIG. 23 is an exploded perspective of the inspection system of FIG. 22;

FIG. 28 is a schematic side elevation of a tucking station of apparatus for making articles such as training pants; and FIG. 29 is a fragmented section taken in the plane of line 29—29 of FIG. 28.

DETAILED DESCRIPTION OF THE DRAWINGS

The methods and apparatus of the present invention can be used to make a variety of pre-fastened articles such as disposable absorbent garments including diapers, training pants, feminine hygiene products, incontinence products, medical garments, other personal care or health care garments, swim pants, athletic clothing, pants and shorts, and the like. More particularly, the methods and apparatus of the present invention can be used to make articles in which at least two elements of the article are connected together during the making thereof to assemble or "prefasten" the article. For ease of explanation, the methods and apparatus of the present invention are hereafter described in connection with making pre-fastened child's training pants, generally indicated as 20 in FIG. 1. In particular, the methods and apparatus will be described in terms of those for making pre-fastened disposable training pants as described in U.S. patent application Ser. No. 09/444,083, U.S. Pat. No. 6,761,711 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference. Training pants 20 can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; the disclosures of which are also incorporated herein by reference.

Figure 1:
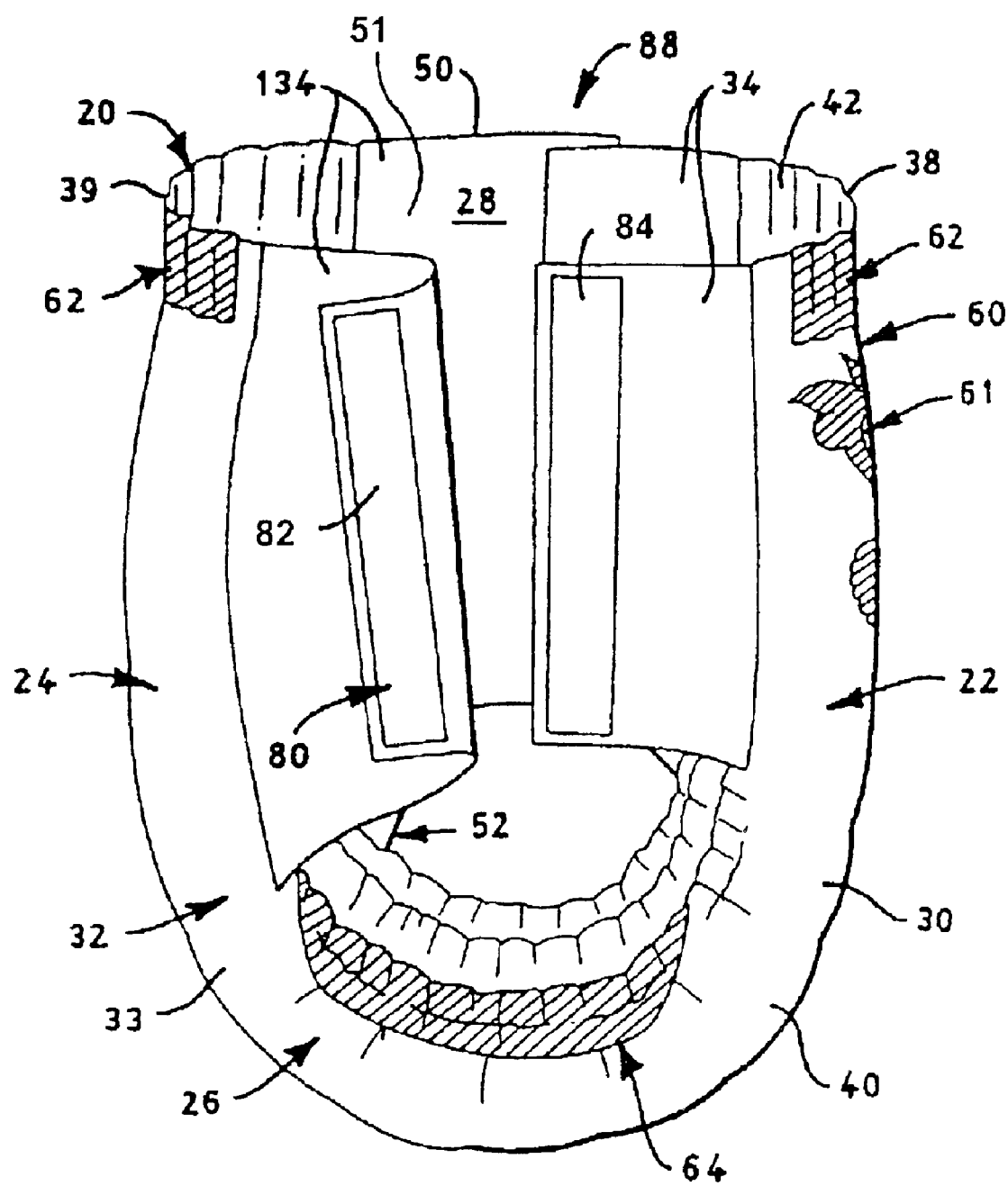
FIG. 1 is a side elevation of a child's training pants with a fastening system of the training pants shown connected on one side of the training pants and disconnected on the other side of the training pants.

With reference now to the drawings, and in particular to FIG. 1, a pair of training pants 20 is illustrated in a partially fastened condition and comprise an absorbent chassis 32 having a front waist region 22, a back waist region 24, a crotch region 26 interconnecting the front and back waist regions, an inner surface 28 which is configured to contact the wearer, and an outer surface 30 opposite the inner surface and configured to contact the wearer's clothing. With additional reference to FIGS. 2 and 3, the absorbent chassis 32 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
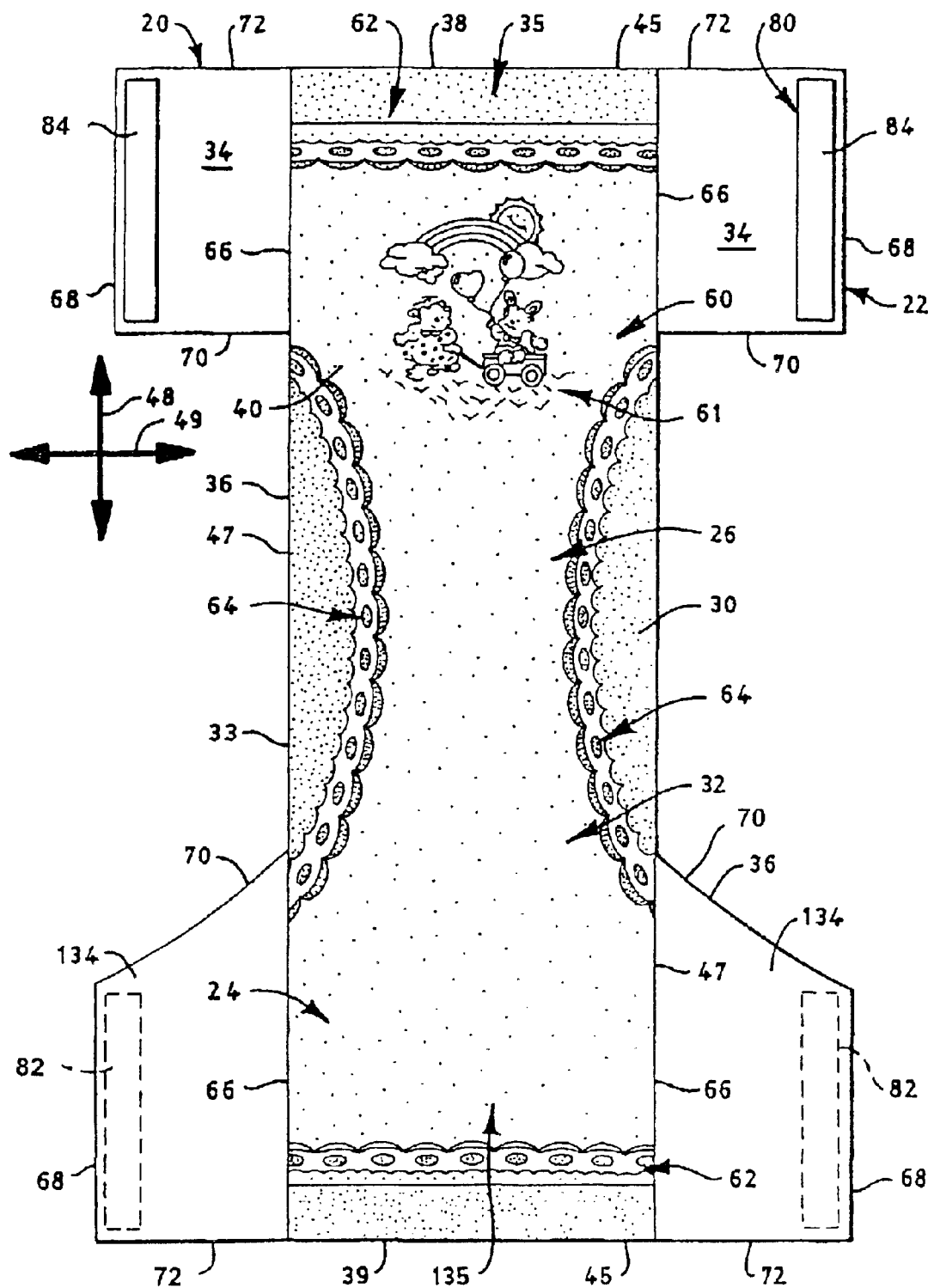
FIG. 2 is a bottom plan view of the training pants of FIG. 1 in an unfastened, stretched and laid flat condition to show the surface of the training pants which faces away from the wearer.
Figure 3:
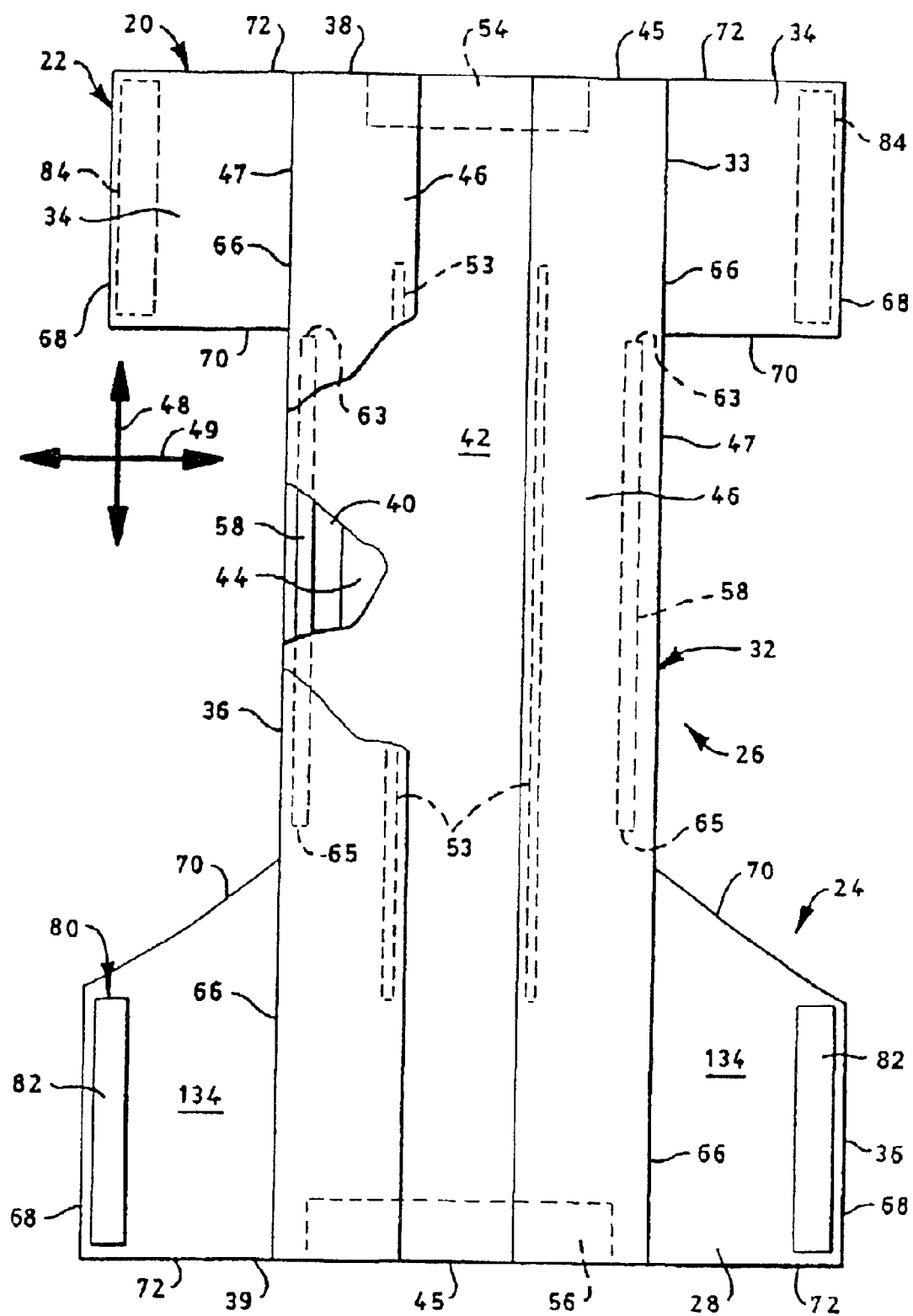
FIG. 3 is a top plan view of the training pants in its unfastened, stretched and laid flat condition to show the surface of the training pants which faces the wearer when the training pants are worn, with portions of the training pants being cut away to reveal underlying features.

The illustrated absorbent chassis 32 comprises a composite structure 33 (FIG. 3), which when laid flat can be rectangular or any other desired shape, and has a pair of laterally opposite front side panels 34 and a pair of laterally opposite back side panels 134 extending outward therefrom. The composite structure 33 and side panels 34, 134 may comprise two or more separate elements, as shown in FIG. 1, or be integrally formed. Integrally formed side panels 34, 134 and composite structure 33 would comprise at least some common materials, such as the bodyside liner, flap composite, outer cover, other materials and/or combinations thereof, and could define a one-piece elastic, stretchable, or nonstretchable pants. The illustrated composite structure 33 comprises an outer cover 40, a bodyside liner 42 (FIGS. 1 and 3) connected to the outer cover in a superposed relation, an absorbent assembly 44 (FIG. 3) disposed between the outer cover and the bodyside liner, and a pair of containment flaps 46 (FIG. 3). The illustrated composite structure 33 has opposite ends 45 which form portions of the front and back waist edges 38 and 39, and opposite side edges 47 which form portions of the side edges 36 of the absorbent chassis 32 (FIGS. 2 and 3). For reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are connected together by a fastening system 80 to define a three-dimensional pants configuration having an interior space 51, a waist opening 50 for receiving the wearer into the interior space of the pants, a pair of leg openings 52 and engagement seams 88 along which the side panels are connected. The interior space 51 of the pants 20 is thus bounded by the absorbent chassis 32, the engagement seams 88 and the portions of the side panels 34, 134 extending on opposite sides of the engagement seams 88 (e.g., between the engagement seams and the absorbent chassis. As used herein, the "interior space" 51 is intended to refer to the space between any two portions of a three-dimensional article which generally oppose each other. It is understood that a transverse cross-section of the article need not be closed, e.g., continuous, to define the interior space 51. For example, a two-dimensional article may be generally folded over on itself so that two portions of the article oppose each other to define an interior space of the article therebetween. Thus, the interior space 51 of the training pants 20 shown in FIG. 1 may be defined by the side panels 34, 134 themselves or, if the side panels are fully straightened therebetween, the interior space is defined by a combination of the side panels and the front and back waist regions 22, 24 of the absorbent chassis 32.

The front waist region 22 comprises the portion of the training pants 20 which, when worn, is positioned on the front of the wearer while the back waist region 24 comprises the portion of the training pants which, when worn, is positioned on the back of the wearer. The crotch region 26 of the training pants 20 comprises the portion of the training pants 20 which, when worn, is positioned between the legs of the wearer and covers the lower torso of the wearer. The front and back side panels 34 and 134 comprise the portions of the training pants 20 which, when worn, are positioned on the hips of the wearer. The waist edges 38 and 39 of the absorbent chassis 32 are configured to encircle the waist of the wearer when worn and together define the waist opening 50 (FIG. 1). Portions of the side edges 36 in the crotch region 26 generally define the leg openings 52.

The absorbent chassis 32 is configured to contain and/or absorb any exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright configuration in at least the crotch region 26 of the training pants 20 to form a seal against the wearer's body. The containment flaps 46 can be located along the side edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 desirably although not necessarily include a front waist elastic member 54, a rear waist elastic member 56, and leg elastic members 58, as are known to those skilled in the art (FIG. 3). The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the composite structure 33. Each leg elastic member 58 has a front terminal point 63 and a back terminal point 65, which represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene non-woven web. The outer layer may also be made of those materials of which the liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumberg, Ill., U.S.A.

If the outer cover 40 is a single layer of material, it can be embossed and/or matte finished to provide a more cloth-like appearance. As earlier mentioned, the liquid impermeable material can permit vapors to escape from the interior space 51 of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pants 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated pair of training pants 20 is designed for use by young girls and includes a registered outer cover graphic 60 (FIGS. 1 and 2). In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for training pants intended for use by young girls, so as to be aesthetically and/or functionally pleasing to them and the caregiver. The appearance-related components are desirably positioned on the training pants 20 at selected locations, which can be carried out using the methods disclosed in U.S. Pat. No. 5,766,389 issued Jun. 16, 1998 to Brandon et al., the entire disclosure of which is incorporated herein by reference. The primary pictorial image 61 is desirably positioned in the front waist region 22 along the longitudinal center line of the training pants 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pants 20 can comprise elastomeric or nonelastomeric materials.

The absorbent assembly 44 (FIG. 3) is positioned between the outer cover 40 and the bodyside liner 42, which can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 comprises a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C., U.S.A.

As noted previously, the illustrated training pants 20 have front and back side panels 34 and 134 disposed on each side of the absorbent chassis 32. The front side panels 34 can be permanently bonded along seams 66 to the composite structure 33 of the absorbent chassis 32 in the respective front and back waist regions 22 and 24. More particularly, as seen best in FIGS. 2 and 3, the front side panels 34 can be permanently bonded to and extend transversely outward beyond the side edges 47 of the composite structure 33 in the front waist region 22, and the back side panels 134 can be permanently bonded to and extend transversely outward beyond the side edges of the composite structure in the back waist region 24. The side panels 34 and 134 may be bonded to the composite structure 33 using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover 40, the bodyside liner 42, and/or another component of the absorbent chassis 32. The front and back side panels 34 and 134 can be permanently bonded together or be releasably connected with one another such as by the fastening system 80 of the illustrated embodiment.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the composite structure 33 to the outer edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pants 20 as compared to the front of the pants. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34, 134 desirably have an average length measured parallel to the longitudinal axis 48 which is about 15 percent or greater, and particularly about 25 percent or greater, of the overall length of the pants, also measured parallel to the longitudinal axis 48. For example, in training pants 20 having an overall length of about 54 centimeters, the side panels 34, 134 desirably have an average length of about 10 centimeters or greater, such as about 15 centimeters. While each of the side panels 34, 134 extends from the waist opening 50 to one of the leg openings 52, the illustrated back side panels 134 have a continually decreasing length dimension moving from the attachment line 66 to the outer edge 68, as is best shown in FIGS. 2 and 3.

Each of the side panels 34, 134 can include one or more individual, distinct pieces of material. In particular embodiments, for example, each side panel 34, 134 can include first and second side panel portions that are joined at a seam, or can include a single piece of material which is folded over upon itself (not shown).

The side panels 34, 134 desirably although not necessarily comprise an elastic material capable of stretching in a direction generally parallel to the transverse axis 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pants 20 includes the fastening system 80 for refastenably securing the training pants about the waist of the wearer. The illustrated fastening system 80 includes first fastening components 82 adapted for refastenable engagement to corresponding second fastening components 84. In one embodiment, one surface of each of the first fastening components 82, 84 comprises a plurality of engaging elements which project from that surface. The engaging elements of the first fastening components 82 are adapted to repeatedly engage and disengage engaging elements of the second fastening components 84.

The fastening components 82, 84 can comprise separate elements bonded to the side panels 134, 34, or they may be integrally formed with the side panels. Thus, unless otherwise specified, the term "fastening component" includes separate components which function as fasteners, and regions of materials such as the side panels 34, 134 which function as fasteners. Moreover, a single material can define multiple fastening components to the extent that different regions of the material function as separate fasteners. The fastening components 82, 84 can be located on the side panels 134, 34, between the side panels such as on the absorbent chassis, or a combination of the two. Alternatively, the fastening components 82, 84 can extend out from the edges of the side panels 134, 34.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

The refastenable fastening system 80 allows for easy inspection of the interior space 51 of the pants 20. When necessary, the fastening system 80 also allows the pants 20 to be removed quickly and easily. This is particularly beneficial when the pants contain messy excrement. For training pants 20, the caregiver can completely remove the pants 20 and replace it with a new one without having to remove the child's shoes and clothing.

In the illustrated embodiment, the first fastening components 82 comprise loop fasteners and the second fastening components 84 comprise complementary hook fasteners. Alternatively, the first fastening components 82 comprise hook fasteners and the second fastening components 84 comprise complementary loop fasteners, or the fastening components 82, 84 can comprise interlocking similar surface fasteners, adhesive or cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a greater average hook height, a greater percentage of directionally-aligned hooks, or a more aggressive hook shape.

Loop fasteners typically comprise a fabric or material having a base or backing structure and a plurality of loop members extending up from at least one surface of the backing structure. The loop material can be formed of any suitable material, such as acrylic, polyamide, polyethylene, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook fasteners typically comprise a fabric or material having a base or backing structure and a plurality of hook members extending upwardly from at least one surface of the backing structure. In contrast to the loop fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded from nylon, polypropylene, polyethylene or another suitable material. Suitable single-sided hook materials for the fastening components are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

With particular reference to FIG. 3, the fastening components 82 are disposed on the inner surface 28 of the back side panels 134. The fastening components 82 are desirably positioned along the outer edges 68 of the back side panels 134, and abutting or adjacent to the waist end edge 72. In certain embodiments, for example, the fastening components 82 can be spaced inward from the outer edges 68 of the front side panels 34 in the range of about 0 to 25 mm. With particular reference to FIG. 2, the second fastening components 84 are disposed on the outer surface 30 of the front side panels 134. The second fastening components 84 are sized to receive the first fastening components 82 and are desirably positioned along the outer edges 68 of the front side panels 34, and abutting or adjacent to the waist end edge 72. As an example, the second fastening components 84 can be spaced inward from the outer edges 68 of the back side panels 134 in the range of about 0 to 25 mm. It is understood that the fastening components 82, 84 may also extend laterally out beyond the outer edges 68 of the side panels 34, 134. Where the first fastening components 82 comprise loop fasteners disposed on the inner surface 28 and the second fastening components 84 comprise hook fasteners disposed on the outer surface 30, the first fastening components can be sized larger than the second fastening components to ensure coverage of the rigid, outwardly-directed hooks.

The fastening components 84, 82 can be adhered to the respective side panels 34, 134 by any means known to those skilled in the art such as adhesive bonds, ultrasonic bonds or thermal bonds. The fastening components 82, 84 may comprise separate fastening elements or distinct regions of an integral material. For example, the training pants 20 can include an integral second fastening material disposed in the front waist region 22 for refastenably connecting to the first fastening components 82 at two or more different regions, which define the second fastening components 84 (FIG. 1). In a particular embodiment, the fastening components 82, 84 can comprise integral portions of the waist regions 24, 22. For instance, one of the elastomeric front or back side panels 34, 134 can function as second fastening components 84 in that they can comprise a material which is releasably engageable with fastening components 82 disposed in the opposite waist region.

The fastening components 82, 84 of the illustrated embodiments are rectangular, although they may alternatively be square, round, oval, curved or otherwise non-rectangularly shaped. In particular embodiments, each of the fastening components 82, 84 has a length aligned generally parallel to the longitudinal axis 48 of the training pants 20 and a width aligned generally parallel to the transverse axis 49 of the training pants. For a child of about 9 to about 15 kilograms (20–30 pounds), for example, the length of the fastening components 82, 84 is desirably from about 50 to about 130 mm, such as about 100 mm, and the width is desirably from about 50 to about 30 mm, such as about 10 mm. With particular embodiments, the fastening components 82, 84 can have a length-to-width ratio of about 2 or greater, such as about 2 to about 25, and more particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

As shown in FIG. 1, when the fastening components 82, 84 are releasably connected, the side edges 36 of the absorbent chassis 32 in the crotch region 26 define the leg openings 52, and the waist edges 38 and 39 of the absorbent chassis, including the waist end edges 72 of the side panels 34, 134, define the waist opening 50. For improved formation of the leg openings 52, it can be desirable in some embodiments for the front side panels 34 to be longitudinally spaced from the back side panels 134 as shown in FIGS. 2 and 3. For example, the front side panels 34 can be longitudinally spaced from the back side panels 134 by a distance equal to about 20 percent or greater, particularly from about 20 to about 60 percent, and more particularly from about 35 to about 50 percent, of the overall length of the pants 20.

When connected, the fastening components 82, 84 of the illustrated embodiment define refastenable engagement seams 88 (FIG. 1) which desirably although not necessarily extend substantially the entire distance between the waist opening 50 and the leg openings 52. More specifically, the engagement seams 88 can cover about 80 to 100 percent, and particularly about 90 to about 98 percent, of the distance between the waist opening 50 and each leg opening 52, which distance is measured parallel to the longitudinal axis 48. To construct the engagement seams 88 to extend substantially the entire distance between the waist and leg openings 50 and 52, the fastening components 82, 84 can be formed to cover about 80 to 100 percent, and more particularly about 90 to about 98 percent, of the distance between the waist end edge 70 and the leg end edge 72 of the side panels 34, 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the engagement seams 88 to be located at the sides of the wearer, it can be particularly desirable for the transverse distance between the fastening components 82 of the back side panels 134 to be substantially equal to the transverse distance between the fastening components 84 of the front side panel 134. The transverse distance between each respective set of fastening components 82, 84 is measured parallel to the transverse axis 49 between the longitudinal center lines of the respective fastening components, measured with the side panels 34, 134 in an unstretched condition. Alternatively, the lateral spacing between the fastening components 82 may be greater or less than the lateral spacing between the fastening components 84. It is also contemplated that fastening components 82 (and/or the fastening components 84) may not be laterally opposite each other, or may be only partially laterally opposite each other, such as by being offset longitudinally, without departing from the scope of this invention.

Figure 4:
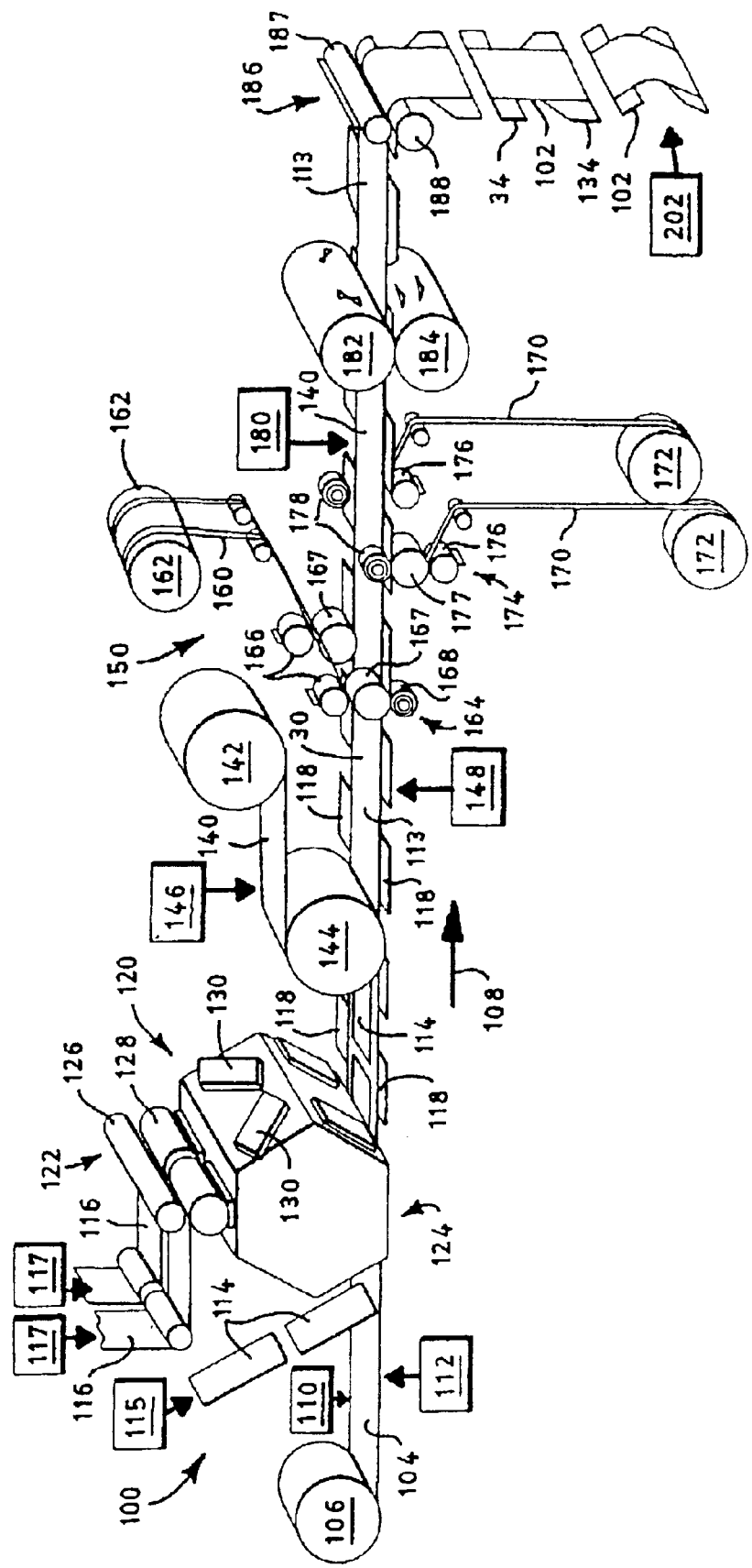
FIG. 4 is a schematic of an assembly section of apparatus for making articles such as training pants.
Figure 5:
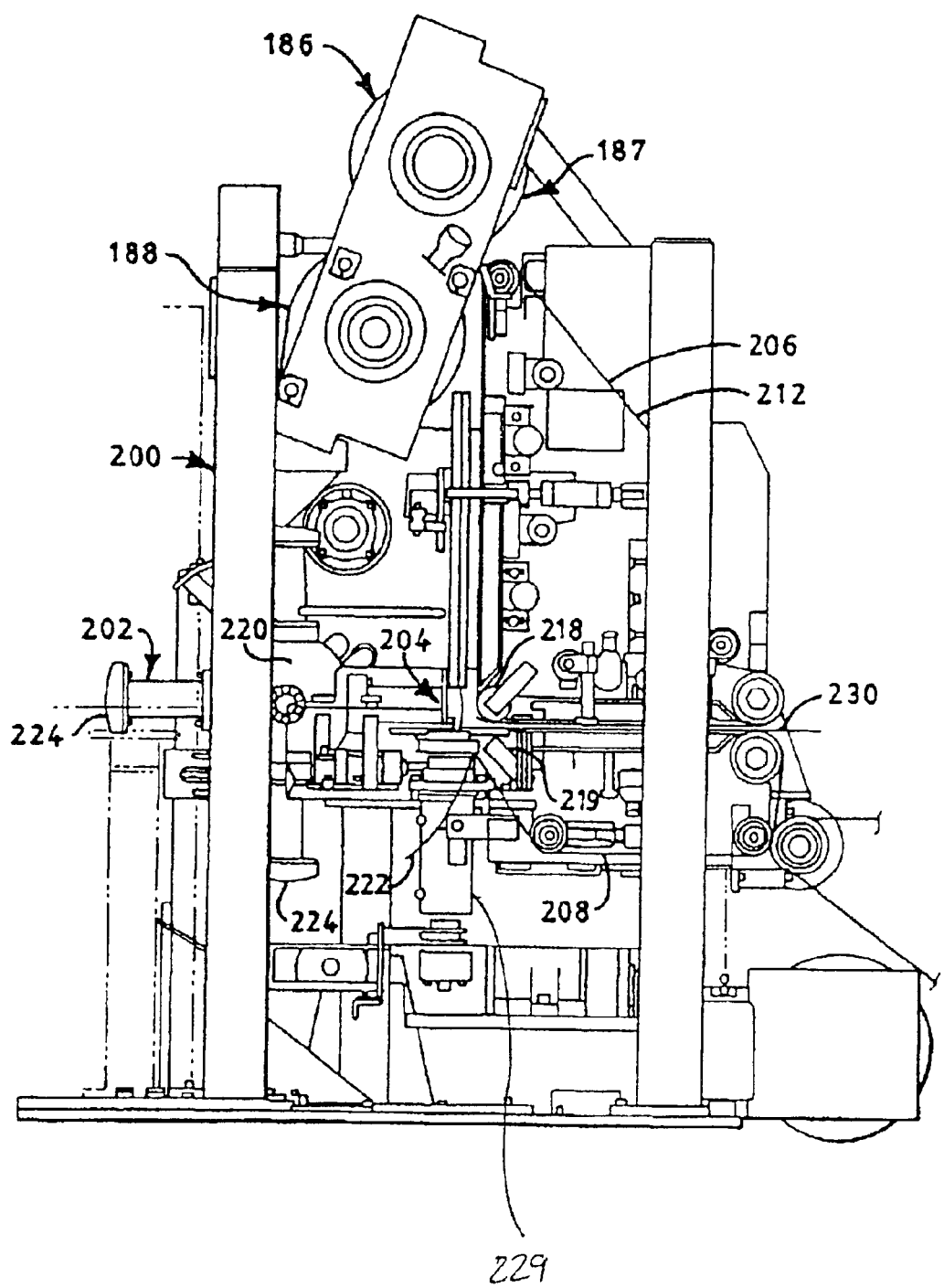
FIG. 5 is a schematic side elevation of a folding section of the apparatus for making articles such as training pants.
Figure 6:
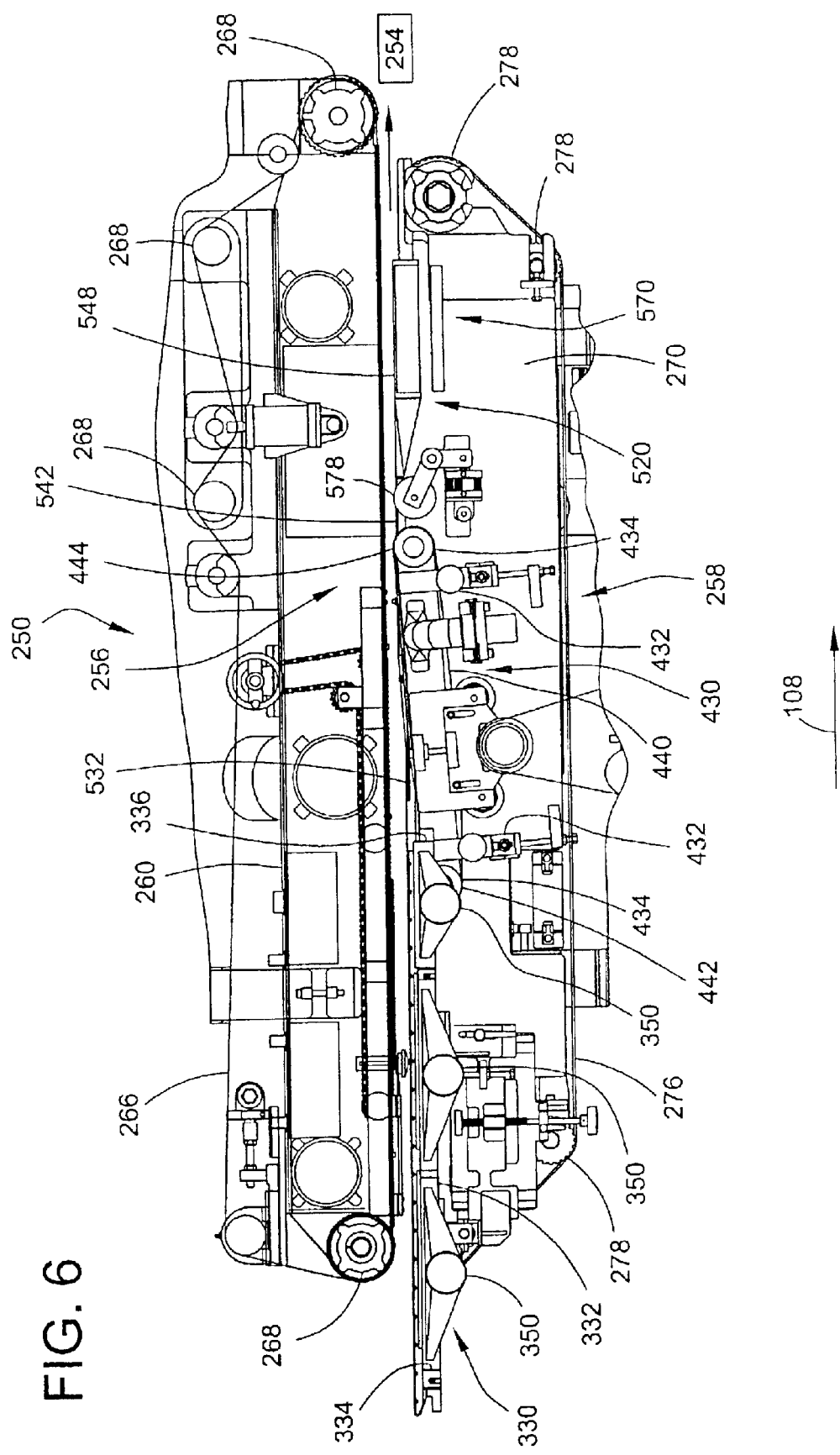
FIG. 6 is a schematic side elevation of a seaming section of the apparatus for making articles such as training pants.

FIGS. 4–6 generally illustrate apparatus of the present invention for making a pre-fastened article, and more particularly for making the pre-fastened, refastenable training pants 20 shown in FIG. 1. The apparatus comprises an assembly section, generally indicated at 100 in FIG. 4, for making partially assembled training pants 102 in an unfolded configuration, a folding section, generally indicated at 200 in FIG. 5, for folding the partially assembled pants generally at the crotch region 26, and a seaming section, generally indicated at 250 in FIG. 6, for connecting the fastening components 84, 82 of the respective front and back side panels 34, 134 to form the pre-fastened training pants.

The various elements of the training pants 102 can be connected together in the assembly section 100 by any means known to those skilled in the art such as, for example, adhesive, thermal and/or ultrasonic bonds. Desirably, most of the elements are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIGS. 4 and 5. Suitable absorbent supply mechanisms, web unwinds, conveyor systems, registration systems, drive systems, control systems and the like, for use with the present apparatus are disclosed in U.S. Pat. No. 5,766,389 issued Jun. 16, 1998 to Brandon et al., the entire disclosure of which is incorporated herein by reference. Also, the outer cover graphics 61 are not shown in FIGS. 4–7.

With particular reference to the assembly section 100 shown in FIG. 4, a continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension.

Various elements can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream from the supply source 106 for attaching pre-assembled containment flaps to the bodyside liner material 104. As various elements are added in the assembly section 100, a continuously moving product assemblage 113 is formed. The product assemblage 113 will be cut downstream to form the partially assembled, discrete training pants 102.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each pair of training pants. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34, 134 can be provided from suitable supply sources 117. The supply sources 117 can comprise one or more standard unwind mechanisms. The side panel material 116 can be cut into individual strips 118 and positioned partially on the bodyside liner material 104 using an applicator device 120. In the cross machine direction, the individual strips 118 desirably extend laterally outward from the bodyside liner material 104 (see FIGS. 4 and 7) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive pants 102.

One suitable applicator device 120 is disclosed in U.S. Pat. Nos. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips. As disclosed by Van Gompel et al., the material 116 used to form the side panels can alternatively be provided in continuous form and pressurized fluid-jets or a rotary die cutter can be employed to cut the material to form leg openings 52. Still alternatively, the side panels 34, 134 of the training pants 20 can be provided by portions of the bodyside liner 42 and/or outer cover 40.

A continuous supply of material 140 used to form the outer cover 40 can be provided from a supply roll 142 or other suitable source. The outer cover material 140 can be transported over a laminator roll 144 and bonded to the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various elements such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream from the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. No. 5,110,403 to Ehlert, which is incorporated herein by reference. Such rotary ultrasonic horns generally have a diameter of from about 5 to about 20 centimeters and a width of from about 2 to about 15 centimeters. Alternatively, the ultrasonic horn may be a stationary ultrasonic horn as is also known to those skilled in the art. Other suitable ultrasonic horns and ultrasonic bonders are commercially available from Branson Sonic Power Company, Danbury, Conn., U.S.A. The bonding devices 148 could otherwise be a thermal or adhesive bonder as are well known.

The continuously moving product assemblage 113 next advances to a fastener application station 150 where fastening components 82, 84 are bonded to the strips 118 of side panel material 116. The location of the fastening components 82, 84 on the composite is a function in part of the configuration of the assembly section 100. As shown in FIG. 4, the assembly section 100 of the illustrated embodiment is configured so that the upward facing surface of the product assemblage 113 will become the outer surface 30 of the training pants 20 and the downward facing surface will become the inner surface 28. Moreover, the illustrated assembly section 100 is configured to produce partially assembled training pants 102 having the front waist region 22 of a leading garment connected to the back waist region 24 of a trailing garment. However, it is understood that the assembly section 100 could alternatively employ any combination of different orientations. For example, the upward facing surface of the product assemblage 113 could form the inner surface 28 of the finished pants 20. Additionally or alternatively, the back waist region 24 of a leading pair of pants 102 can be connected to the front waist region 22 of the trailing pair of pants, or the pants can be arranged in a front-to-front/back-to-back relationship. Still alternatively, the assembly section 100 could be constructed as a cross-machine direction process wherein the longitudinal axis 48 of each pair of partially assembled pants 102 could be perpendicular to the machine direction 108 during part or all of the assembly process.

Figure 7:
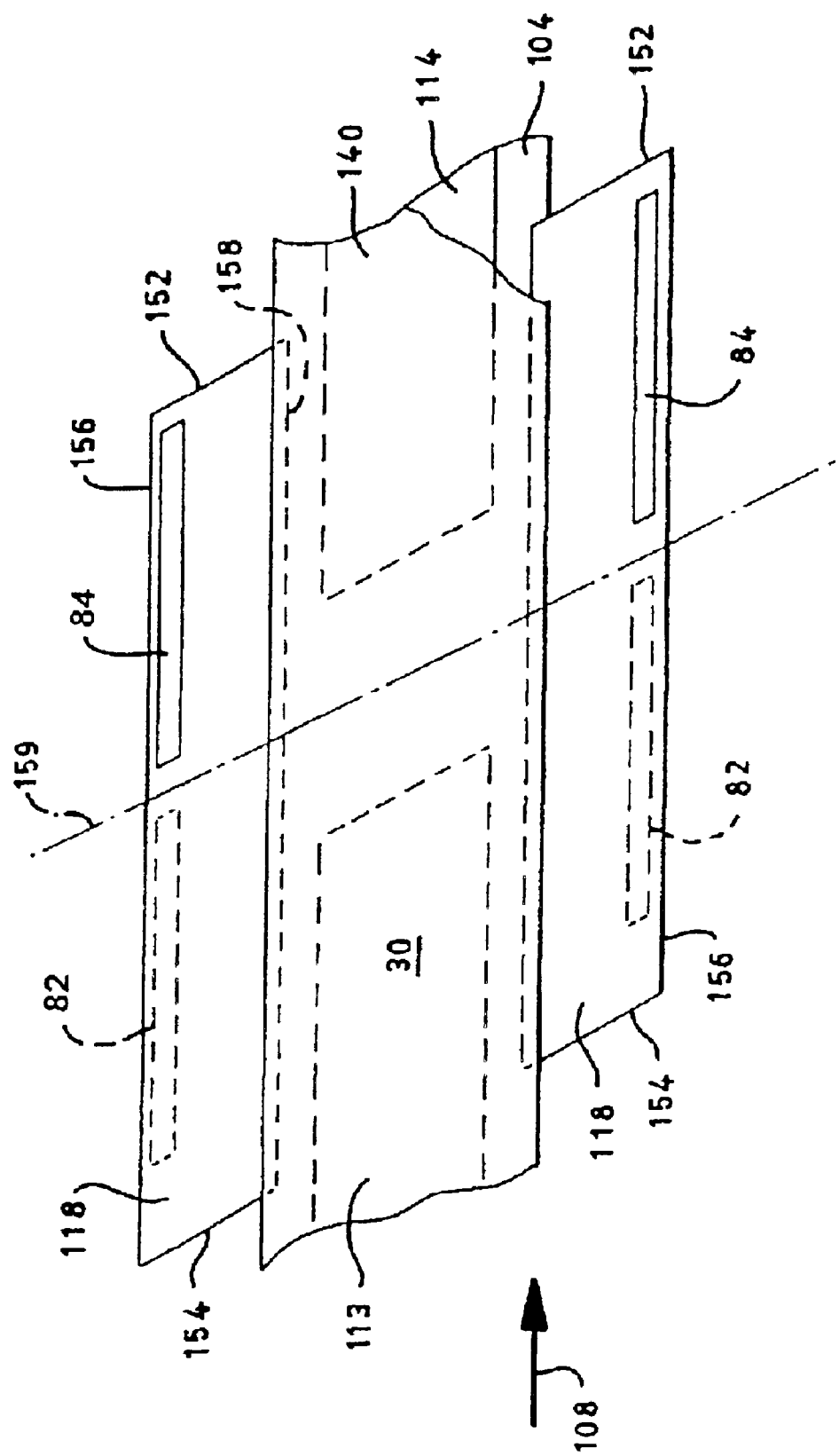
FIG. 7 is a schematic of a portion of a continuously moving assemblage at one location along the assembly section of FIG. 4.

The locations of the fastening components 82, 84 in this embodiment are best illustrated in FIG. 7, which shows a portion of the product assemblage 113 moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete partially assembled training pants 102. Based on the illustrated orientation of the continuously moving product assemblage 113, the first fastening components 82 can be bonded to the underside of the strips 118 and the second fastening components 84 can be bonded to the top of the strips. Additionally, the first fastening components 82 can be disposed relatively closer to the trailing edge 154 and the second fastening components 84 can be disposed relatively closer to the leading edge 152. The first fastening components 82 can be spaced in the machine direction 108 from the second fastening components 84 so that the cut line 159 passes therebetween.

With reference again to FIG. 4, continuous webs of a second fastener material 160 used to form the second fastening components 84 can be provided from supply rolls 162 or other suitable sources. The second fastener materials 160 can be cut into individual second fasteners 84 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 can be provided from supply rolls 172 or other suitable sources. The first fastener materials 170 can be cut into individual first fastening components by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and disposed on the undersides of the strips 118 of side panel material 116.

It is contemplated that other arrangements can be used to attach the fastening components 82, 84 to the side panel material 116. For example, the fastening components 82, 84 can be applied to the side panel material 116 prior to uniting the side panel material with the bodyside liner material 104 and/or the outer cover material 140; the fastening components can be applied to the bodyside liner material 104 and/or outer cover material 140, whether separate side panels 34, 134 are used or not; portions of other elements such as the bodyside liner and/or outer cover can form one or more of the fastening components; the separate side panels or integral side panels can themselves form one or more of the fastening components; the fastening components 82, 84 can be attached as pre-engaged composites or the like without departing from the scope of this invention.

After the fastening components 82, 84 are disposed on the strips 118 of side panel material 116, bonding devices 180 such as ultrasonic bonders can be employed to bond the fastening components to the strips. For example, the strips 118 can be transported between a rotary ultrasonic horn and an anvil roll, which devices are positioned on each side of the process at the cross machine direction location of the fastening components 82, 84. Alternatively, the fastening components 82, 84 could be transported using only adhesive. Particular ultrasonic bond patterns comprising individual, circular bonds which are compatible with mechanical fastening materials are disclosed in U.S. Pat. No. 5,660,666 issued Aug. 26, 1997 to Dilnik et al., which is incorporated herein by reference. Efficient arrangements for attaching the fastening components with nonadhesive bonding devices are further described in U.S. patent application Publication No. US 2002-000029, filed on May 15, 2001 by J. D. Coenen et al. and titled "Methods For Making Garments With Fastening Components," which is incorporated herein by reference. For secure attachment, it may be desirable to attach the fastening components 82, 84 to the side panel material 116 with both adhesive and thermal bonds. Suitable attachment adhesives are available from commercial vendors such as Findley Adhesive, Inc., Wauwatosa, Wis., U.S.A.

In particular embodiments, the bonding devices 180 can provide timed, non-uniform bonding of the fastening components to the side panel material 116. The degree of bonding, such as the number of bonds per unit area or the bond strength per unit area, can be greater in certain target areas compared to non-target areas. Enhanced bonding in target areas can be beneficial particularly near the waist and leg openings 50 and 52 to reduce delamination of the fastening components from the side panel material 116. Thus, the bonding devices 180 can be adapted to create relatively more bonds or stronger bonds between the fastening components 82, 84 and the side panel material 116 when the side panel material 116 reaches a particular machine direction 108 location. In one particular embodiment, the target areas correspond to portions of the fastening components 82, 84 near the waist edges 38 and 39. The bonding devices 180 can be registered to provide a relatively higher degree of bonding which begins while disposed on one fastening component (such as the fastening component 84 in FIG. 7), continues through the region where the product assemblage 113 will subsequently be cut (see cut line 159 in FIG. 7), and ends after being disposed on another fastening component (such as fastening component 82). Alternatively, the bonding devices 180 can destroy engaging elements of the fastening components 82, 84 in the target areas, so that the fastening components will be less able to aggressively attach to one another in the target areas.

The strips 118 of side panel material 116 can be trimmed if desired, for example to provide angled and/or curved leg end edges 70 in the back waist region 24 (FIGS. 2 and 3). To this end, the assembly section 100 can include a die cutting roll 182 and a backing roll 184. In the illustrated embodiment, a portion of each strip 118 is trimmed from the trailing edge 154 (FIG. 7) in order to form the angled and/or curved leg end edges 70 in the back waist region 24.

The method and apparatus to this point provides a continuous web of interconnected and partially assembled training pants moving in the machine direction indicated by arrow 108. This continuously moving product assemblage 113 is passed through a cutter 186 which selectively cuts the web into discrete, partially assembled training pants 102. Such cutters 186 are generally known to those skilled in the art and can include, for example, the combination of a cutting roll 187 and an anvil roll 188 through which the web travels. The anvil roll 188 can include a hardened steel rotating roll while the cutting roll 187 can include one or more flexible hardened steel blades clamped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

Figure 8:
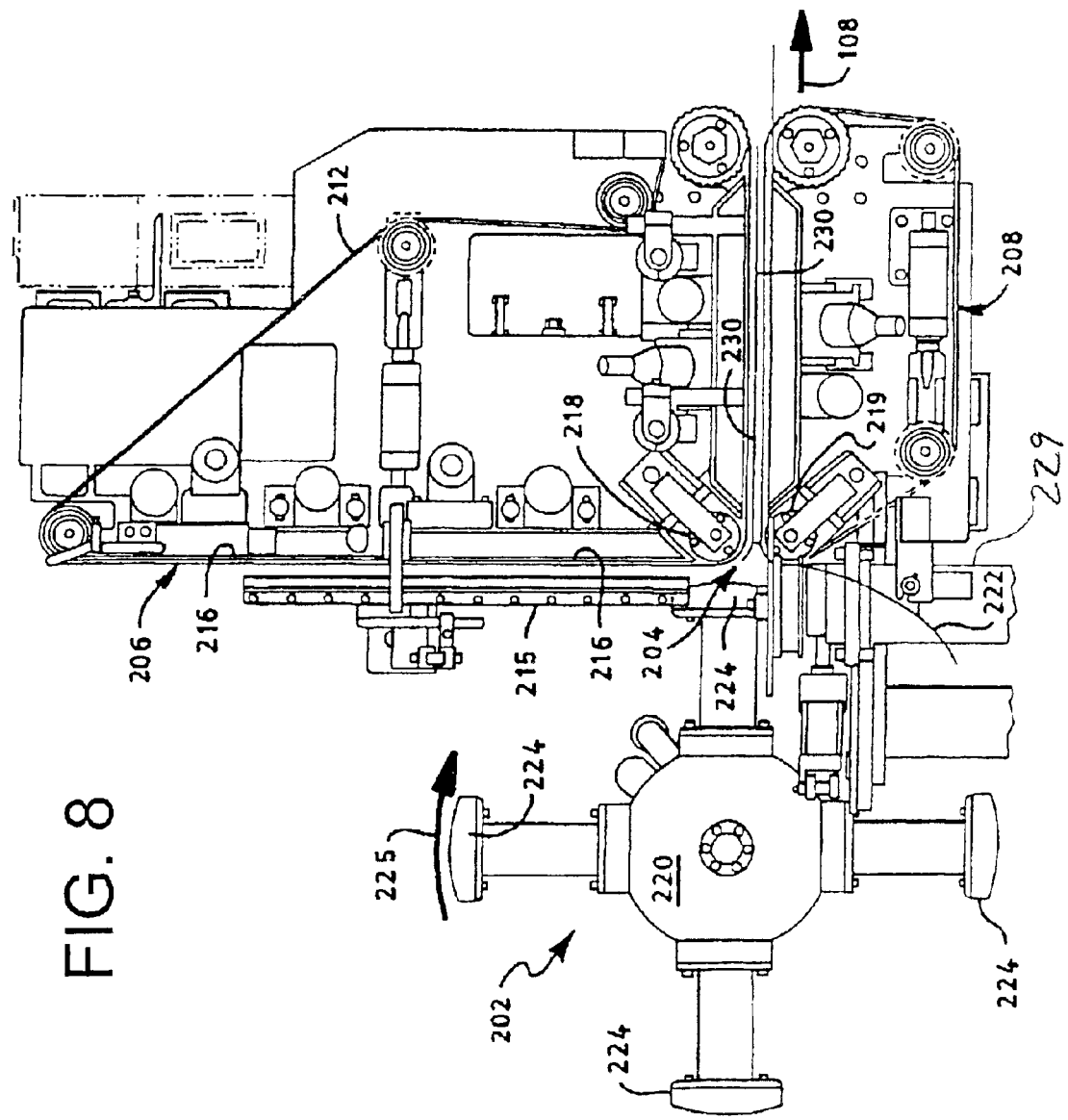
FIG. 8 is an enlarged side elevation of the folding section of FIG. 5.
Figure 9:
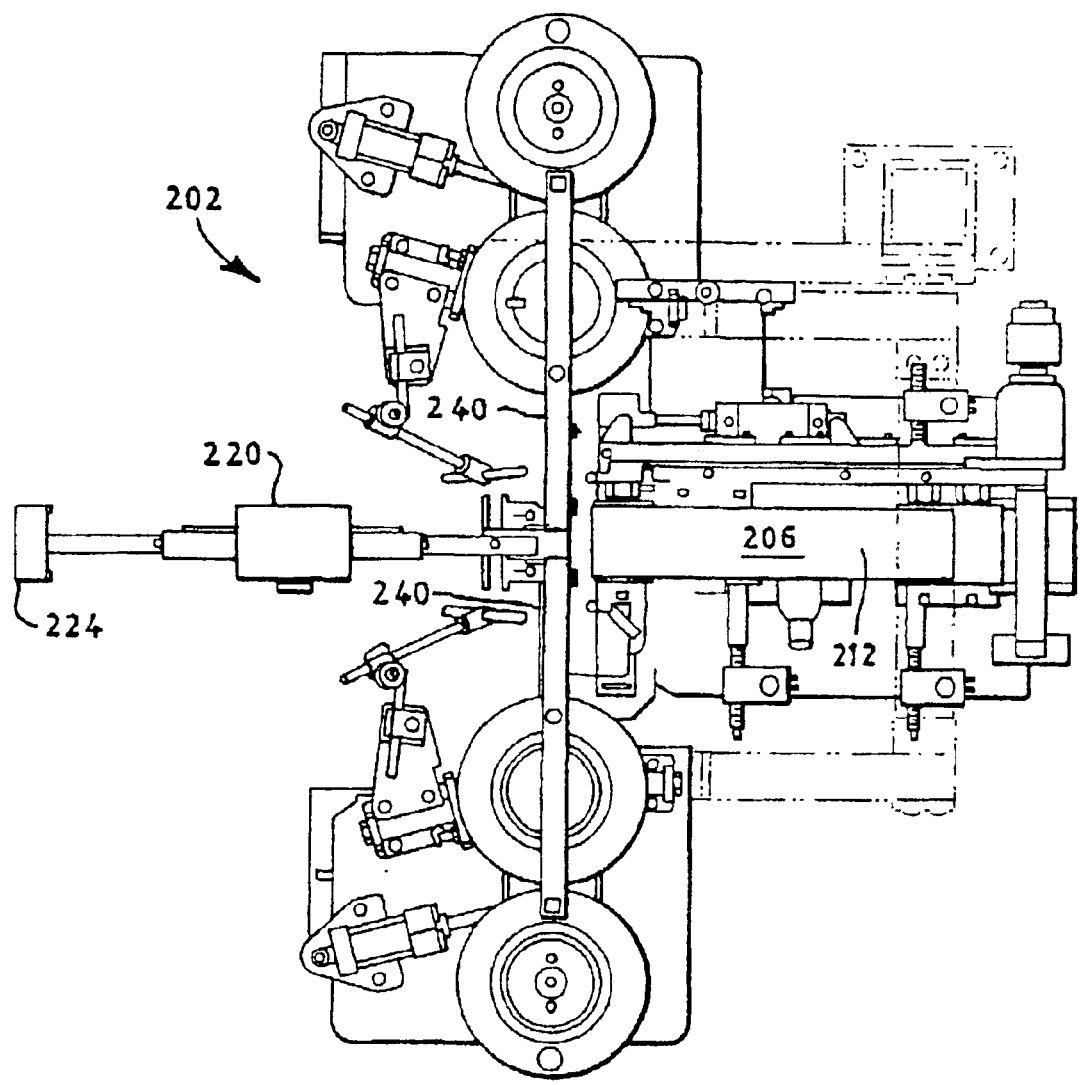
FIG. 9 is a top plan view of a portion of the folding section of FIG. 5.

With particular reference now to FIGS. 5, 8 and 9, the discrete partially assembled training pants 102 are delivered to and folded at the folding section 200 using any suitable folding mechanism 202. For example, the training pants 102 can be folded about a fold line which generally bisects the training pants laterally through the crotch region 26. As such, the waist regions 22 and 24 of the partially assembled pants 102 are positioned in opposed relationship with each other, with the side panels 34, 134 extending laterally outward therefrom parallel to the transverse axis 49 of the training pants in opposed relationship with each other. Desirably, each of the training pants 102 is consistently folded about the fold line such that the front and back waist edges 38 and 39 of the training pants align with each other.

A variety of folding mechanisms 202 can be used, such as blade folders, linear folders, book folders, tucker blades or the like. The specific type selected for a given application may depend upon the type of garment being manufactured and the type of fastening mechanism used to secure the garment in a pants configuration. In the illustrated embodiment, the folding mechanism 202 controls the side panels 34, 134 during folding so that the refastenable fastening components 82, 84 are inhibited against engaging one another or engaging another material during the folding operation. Other arrangements for maintaining separation of the side panels 34, 134 and fastening components 82, 84 during folding are disclosed in PCT Application No. WO 01/87210 by J. D. Coenen et al., titled "Folding And Manufacture Of Pants," which is incorporated herein by reference.

The illustrated blade folding mechanism 202 comprises a plurality of rotating folding or tucker blades 240 (FIG. 9) which are configured to contact the training pants 102 along the fold line. Rotation of the folding blades 240 can force the training pants 102 into a nip 204 between two rotating folding conveyors 206 and 208 causing the training pants to fold about the fold line. The folding conveyors 206 and 208 can form part of a transport system for moving the folded training pants 102 in the machine direction 108 (FIG. 8). The folded training pants 102 are illustrated as being transported in the machine direction 108 with the crotch region 26 leading the waist regions 22 and 24. Alternatively, the process and apparatus could be modified so that the waist regions lead the crotch region (not shown).

The series of unfolded, discrete training pants 102 can be transferred from the vacuum anvil roll 188 (FIG. 4) of the cutter 186 to the upper folding conveyor 206 (FIGS. 5, 8 and 9). The training pants 102 can be held by vacuum on the upper folding conveyor 206 and transported toward the nip 204 formed between the folding conveyors 206 and 208. While being transported toward the nip 204, the side panels 34, 134 can be smoothed out or straightened if desired by various means including fluid stabilizing devices. For example, air knives 215 (FIG. 8), air bars, air nozzles or the like can be mounted in proximity to the upper folding conveyor to provide a stream of fluid directed toward the side panels to stabilize and/or straighten the side panels. The air knives 215 can blow the side panels 34, 134 against skid plates 216 positioned transversely outward from the upper folding conveyor belt 212. Alternatively, or in addition thereto, the upper folding conveyor 206 can incorporate fluid stabilizing devices (not shown) consisting of fluid manifolds operatively connected to a high pressure fluid source to fluidly shake the side panels 34, 134. The fluid stabilizing devices (not shown) desirably prevent folding of the side panels 34, 134 as the training pants 102 move along the upper folding conveyor 206. Sensing devices can also be employed at this point to detect products that have folded side panels or that are misaligned relative to the machine center line.

The product folding nip 204 can be formed between a timed vacuum nose roll 218 of the upper folding conveyor 206 and a timed vacuum nose roll 219 of the lower folding conveyor 208 (FIGS. 5 and 8). As the leading edge of each pair of pants 102 is introduced onto the upper nose roll 218, a rotary valve 229 can be used to disrupt the vacuum draw of the nose roll 218 of the upper folding conveyor 206. This allows the leading edge of the pants 102 to pass by the nose roll 218 without getting drawn into the nip 204. Alternatively, the vacuum source can be temporarily disconnected from the nose roll 218 of the upper folding conveyor 206. Any suitable control system (not shown) may be used to control operation of the vacuum nose rolls 218, 219. For example, in certain embodiments, compressed air nozzles or jets (not shown) can be used to cycle vacuum through the nose rolls 218, 219, such as by injecting compressed air into interior chambers (not shown) of the nose rolls to negate the vacuum therein.

A product control drum 220 can guide the leading half of the training pants 102 onto a curved transfer plate 222 (FIGS. 5 and 8). The product control drum 220 can comprise a plurality of vacuum pucks 224 which rotate in the direction of arrow 225. The illustrated product control drum 220 includes four vacuum pucks 224 to guide four training pants 102 per revolution. Rotation of the product control drum 220 can be timed so that a vacuum puck 224 grabs the leading half of a training pants 102 and transfers the leading edge onto the curved transfer plate 222. The absorbent chassis 32 and/or side panels 134 of the leading half can be carried on a vacuum puck 224 past the nose roll 219 of the lower folding conveyor 208. Compressed air can be introduced inside this lower nose roll 219 at this point to negate vacuum draw and to permit the entire leading edge and side panels 134 to transfer onto the curved transfer plate 222. Alternatively of course, the vacuum source can be temporarily disconnected from the nose roll 219.

With reference to FIG. 9, the opposed tucker blades 240 move in an orbital manner to pass through the vertical path of the training pants 102. The tucker blades 240 can contact the crotch region 26 of the pants 102 and insert the crotch region into the folding nip 204. As this happens, the leading half of the pants 102 reverses direction over the curved transfer plate 222 and is pulled into the nip 204. The vacuum puck 224 can cease drawing vacuum at this point to release the leading half. Correspondingly, the trailing half of the pants 102 is pulled around the upper nose roll 218. Thus, both halves of the training pants 102 can change from motion in a generally vertical plane to motion between the folding conveyors 206 and 208 in a generally horizontal plane.

Figure 10:
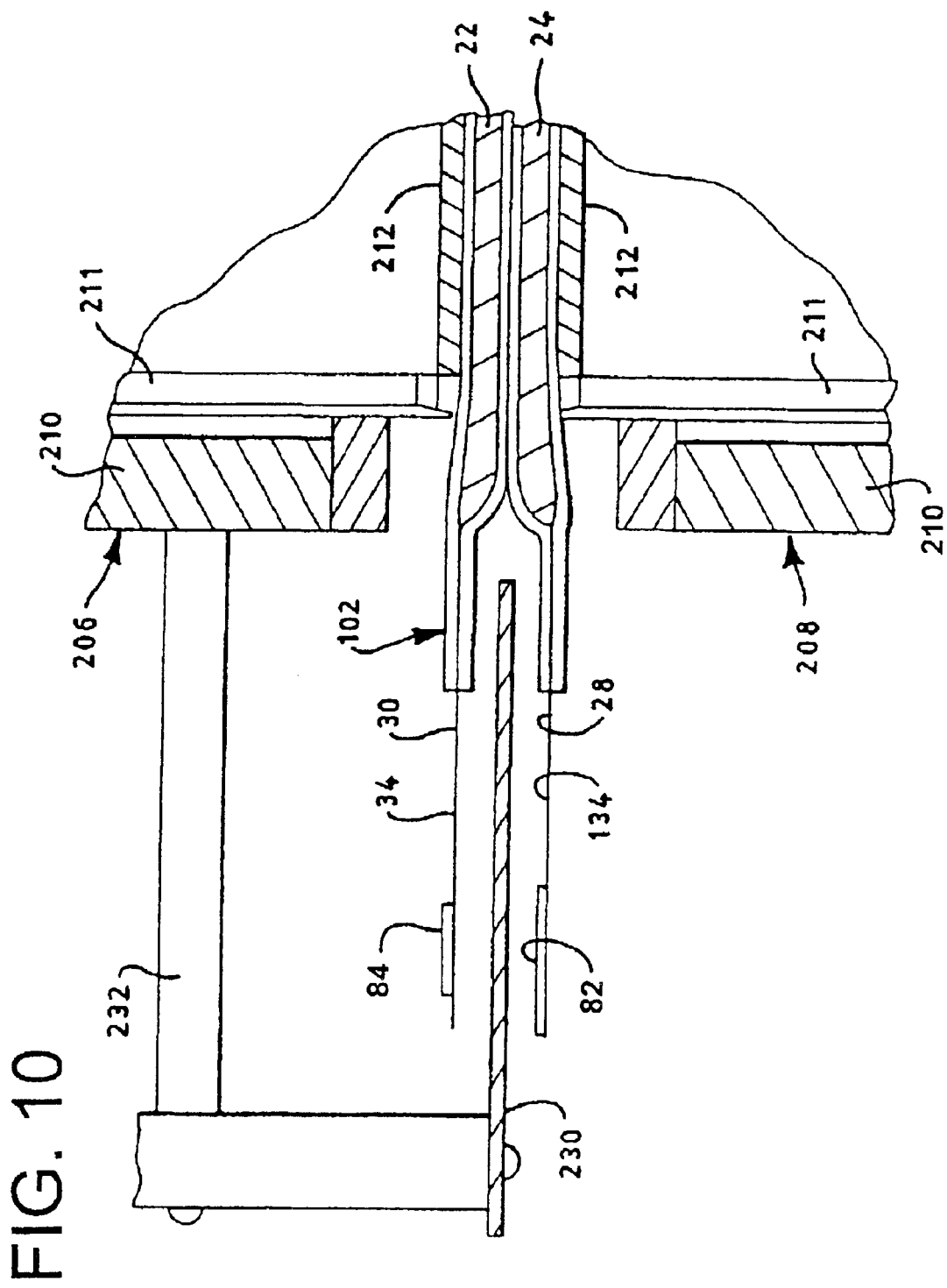
FIG. 10 is an enlarged section view of a portion of a pair of training pants at a location within the folding section of FIG. 2.

The illustrated folding mechanism 202 can maintain separation between the front and back side panels 34, 134. As the pants 102 enter the folding nip 204, compressed air can be shut off to the upper nose roll 218 so that the side panels 34 of the trailing half are drawn by vacuum to the upper nose roll. The trailing side panels 34 are thus drawn to the upper nose roll 218 and follow its rotation around the roll and over side panel separation plates 230 (FIGS. 8 and 10). Similarly, as the leading half of the pants 102 is pulled into the folding nip 204, compressed air can be shut off to the lower nose roll 219 so that the side panels 134 of the leading half are drawn by vacuum to the lower nose roll. The leading side panels 134 are thus drawn to the lower nose roll 219 and follow its rotation around the roll and beneath the side panel separation plates 230.

FIG. 10 illustrates a portion of partially assembled training pants 102 positioned between the upper and lower folding conveyors 206 and 208 at a location downstream from the nose rolls 218 and 219. At this point, the training pants 102 have been folded in half and transported in the machine direction 108 (FIG. 8) by the conveyors 206 and 208. The illustrated folding mechanism 202 can thus maintain the front side panels 34 separated from the back side panels 134 during folding.

Each folding conveyor 206 and 208 as illustrated in greater detail in FIG. 10 can comprise a frame structure 210, a plurality of rotatable pulleys 211 associated with the frame structure, and a continuous belt 212 carried on the pulleys. A drive system and conveyor shaft (not shown) can be used to rotatively drive one or more of the pulleys. The folding conveyors 206 and 208 can comprise vacuum conveyors as are well known in the art, in which case the continuous belt can be formed of a fluid permeable material. The folding conveyors desirably transport the training pants 102 with the longitudinal center line of the pants traveling on the longitudinal center line of the conveyors. As depicted, the front and back side panels 34, 134 can project laterally outward from the frame structure 210, outstretched in the cross-machine direction.

While traveling on the folding conveyors 206 and 208, the side panels 34, 134 can be smoothed out or straightened if desired by various means including fluid stabilizing devices (not shown). Suitable fluid stabilizing devices can comprise air knives, air bars, air nozzles, vacuum devices or the like to provide a stream of fluid directed toward the side panels. The fluid stabilizing devices can be incorporated within either or both of the folding conveyors 206 and 208 or can comprise separate devices positioned in proximity to the conveyors.

Following conveyance of the partially assembled training pants 102 through the illustrated folding mechanism 202, the front waist region 22 and front side panels 34 of the partially assembled training pants as shown in FIG. 10 are disposed above the back waist region 24 and back side panels 134. The fastening components 82 are disposed on the inner surface 28 of the back side panels 134 and the fastening components 84 are disposed on the outer surface 30 of the front side panels 34. The separation plates 230 can extend in the machine direction 108 to maintain separation between the front and back side panels 34, 134. The separation plates 230 can comprise a low friction material or coating, such as: stainless steel; Teflon®; aluminum; ultra-high molecular weight polyethylene (UHMW-PE); polyoxymethylene (acetals), for instance a homopolymer available from E. I. Du Pont de Nemours and Company, Wilmington, Del., USA under the tradename DELRIN; or the like. In particular embodiments, the separation plates 230 can comprise a thin layer of Teflon®, UHMW-PE, DELRIN or the like glued to a plate formed of steel, aluminum or the like. The separation plates 230 can be mounted using suitable support members 232 (FIG. 10) to either the folding conveyors 206 or 208 or other suitable frame structure (not shown). It is also contemplated that the separation plates 230 could include air stablization devices (not shown) to straighten and maintain stability of the side panels 34, 134.

From the folding station 200, the continuous stream of discrete, partially assembled and folded training pants 102 enters a seaming section 250 (FIG. 6) and is transported therethrough in a machine direction 108 indicated by the direction arrow in FIG. 6. In general, the seaming section 250 controls the unattached side panels 34, 134 so as to position portions of the side panels, and more particularly the respective fastening components 84, 82 of the side panels, in at least partially opposed relationship with each other; to connect the fastening components together to define the engagement seams 88; and to then inspect the engagement seams 88 to assess whether the side panels are properly aligned and connected. The seaming section 250 thus converts the discrete, partially assembled and folded training pants 102 into the pre-fastened training pants 20 (FIG. 1) having the waist opening 50, leg openings 52 and the interior space 51 bounded in part by the engagement seams 88.

Figure 11:
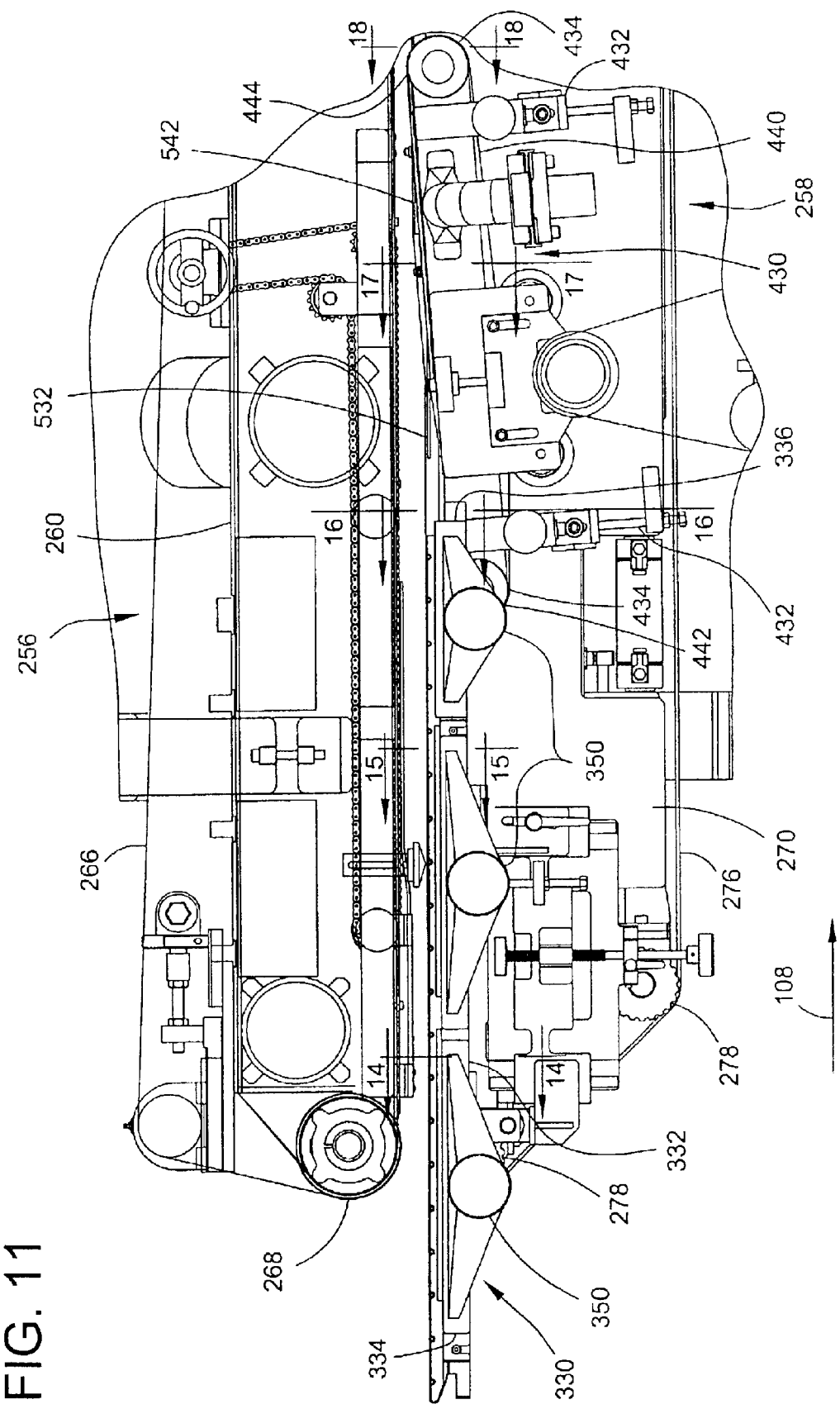
FIG. 11 is an enlarged side elevation of an upstream portion of the seaming section of FIG. 6.
Figure 12:
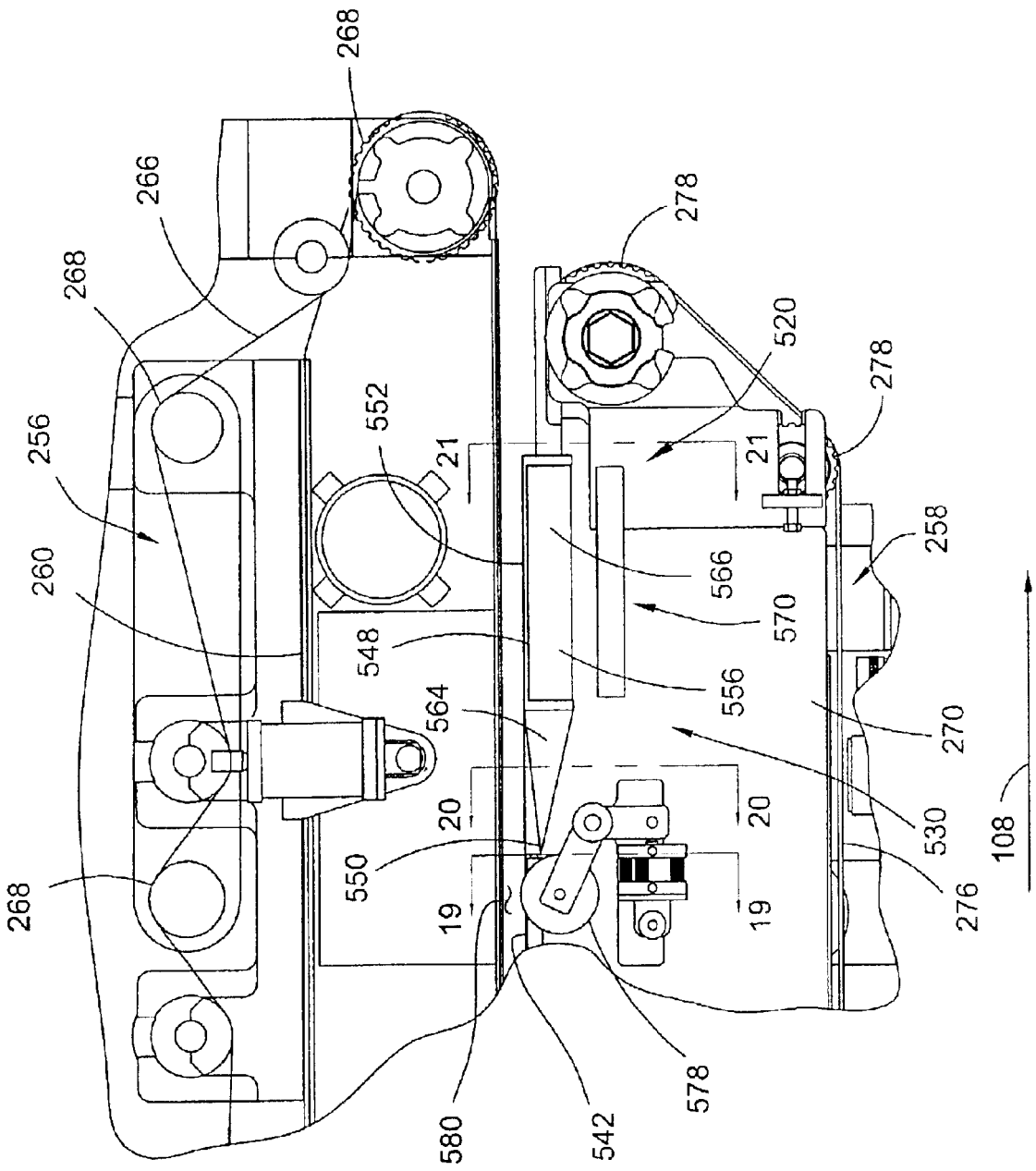
FIG. 12 is an enlarged side elevation of a downstream portion of the seaming section of FIG. 6.
Figure 13:
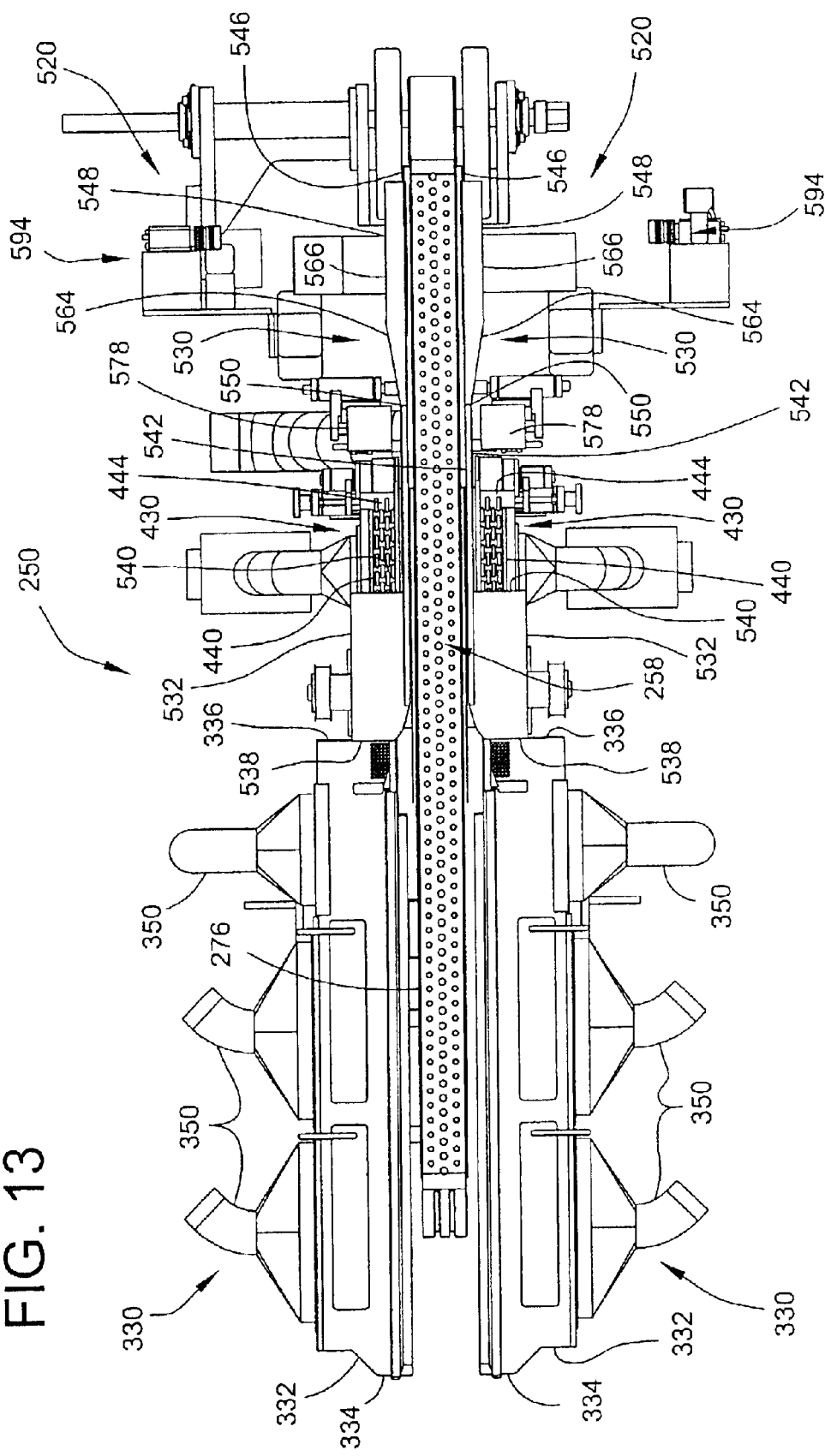
FIG. 13 is a top plan view of a lower portion of the seaming section of FIG. 6.
Figure 24:
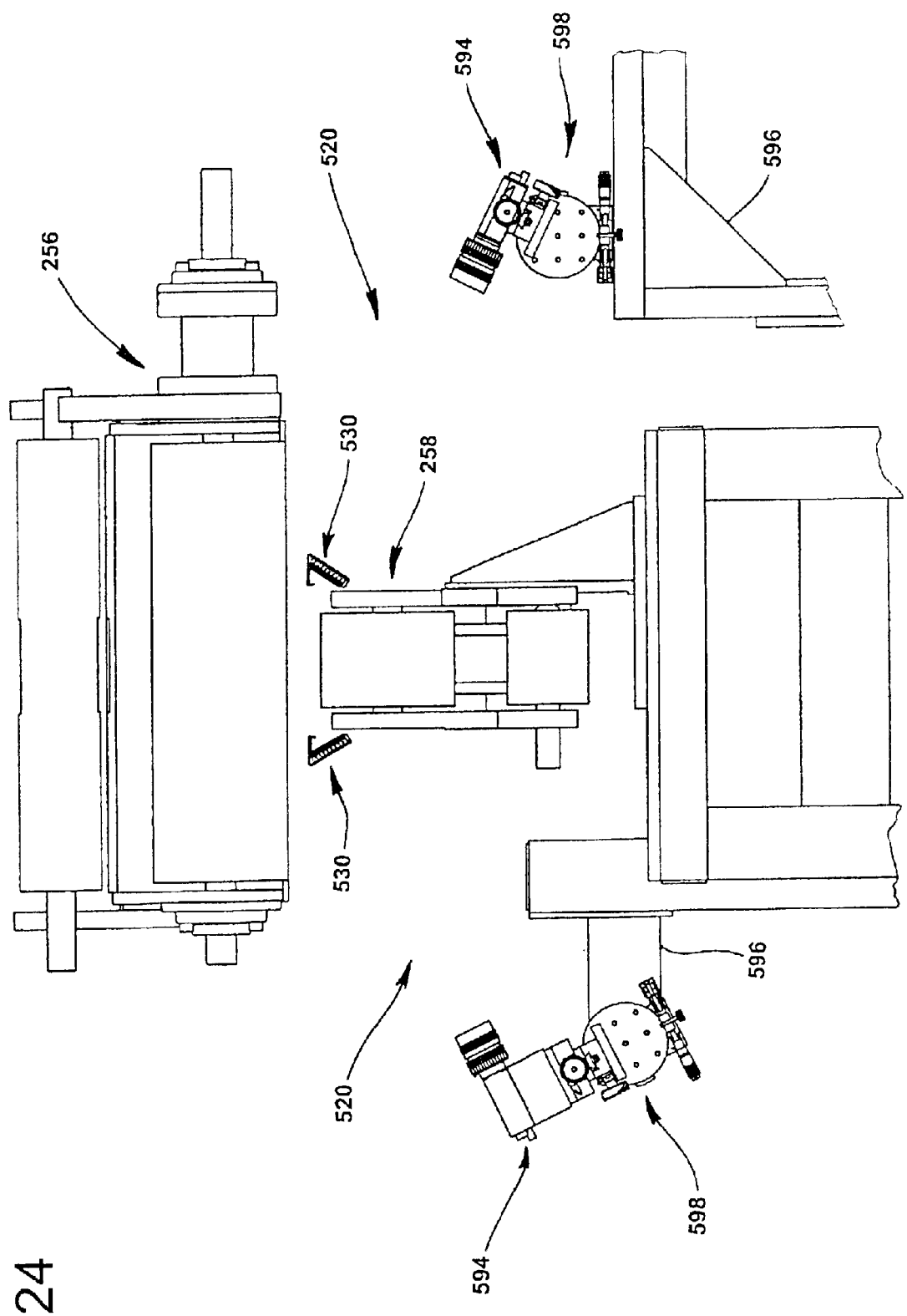
FIG. 24 is an end view of the downstream end of the seaming section of FIG. 6.

Construction and operation of the seaming section 250 is further described herein with particular reference to FIGS. 11–21 and 24. FIGS. 11 and 12 respectively illustrate side elevations of the upstream and downstream portions of the seaming section 250, FIG. 13 illustrates a top plan of a lower portion of the seaming section and FIG. 24 illustrates an end view of a downstream end of the seaming section. FIGS. 14–21 are sections taken at sequential locations along the seaming section 250. For ease of explanation, these sections illustrate only one side (e.g., the right hand side relative to the machine centerline) of the seaming section 250 and the training pants 102 conveyed therethrough, it being understood that the left hand side of the seaming section is constructed and operates substantially similar to the right hand side.

Figure 14:
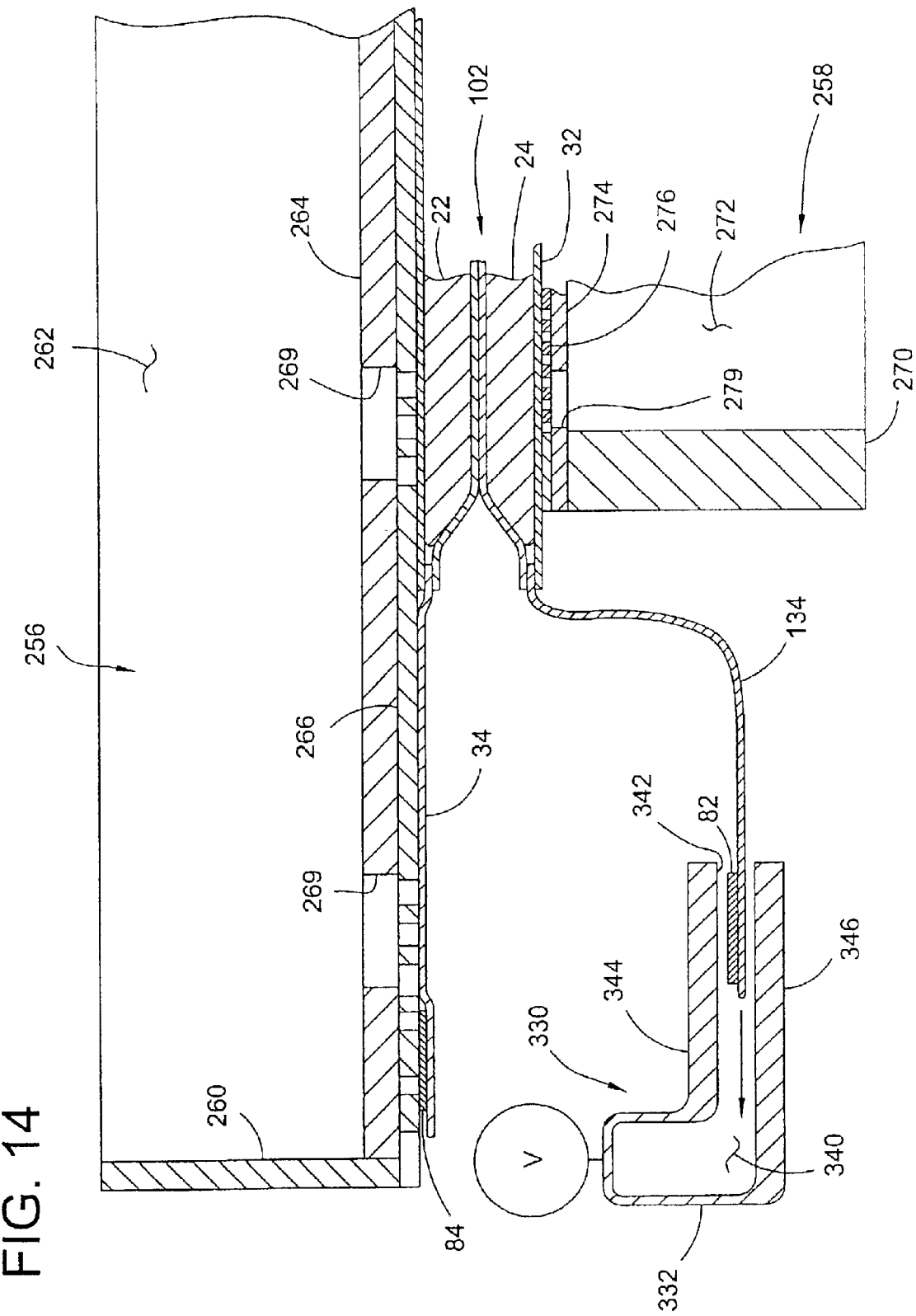
FIG. 14 is a partial section taken in the plane of line 14—14 of FIG. 11.

With particular reference to FIGS. 6, 11 and 14, the seaming section 250 comprises upper and lower alignment conveyors, generally indicated as 256 and 258, respectively, which broadly define a transport system for transporting discrete, partially assembled training pants 102 from the upper and lower folding conveyors 206 and 208 (FIG. 5) through the seaming section in the machine direction 108. More specifically, the alignment conveyors 256 and 258 define therebetween a pant transport plane, which in the illustrated embodiment is generally horizontal, in which the training pants 102 are transported through the seaming section 250. As illustrated, the upper alignment conveyor 256 comprises frame structure 260, one or more vacuum chambers 262 (FIG. 14) defined within the frame structure, one or more vacuum cover plates 264 (FIG. 14) mounted on the frame structure and one or more continuous fluid-permeable belts 266 carried on a plurality of rotatable pulleys 268 or other suitable devices.

Similarly, the lower alignment conveyor 258 comprises frame structure 270, a vacuum chamber 272 (FIG. 14) defined within the frame structure, a vacuum cover plate 274 (FIG. 14) mounted on the frame structure and a continuous fluid-permeable belt 276 carried on a plurality of rotatable pulleys 278 or other suitable devices. The vacuum cover plates 264 and 274 and related equipment can be adjustable if desired to accommodate various pants sizes. A drive system (not shown) and conveyor shaft (not shown) can be used to rotatively drive one or more of the pulleys 268 and 278. The vacuum chambers 262 and 272 can be operatively connected to a source of vacuum (not shown) and the vacuum cover plates 264 and 274 can be provided with a plurality of holes 269 and 279, respectively.

With reference to FIG. 14, the seaming section 250 is also illustrated and described herein with the training pants 102 oriented such that the front waist region 22 is drawn against the upper alignment conveyor 256 and the back waist region 24 is drawn against the lower alignment conveyor 258. Thus, the front side panels 34 are initially positioned above the back side panels 134, with the fastening component 84 of the front side panel facing up (e.g., away from the fastening component 82 of the back side panel). However, it is understood that the pants 102 may be inverted, e.g., such that the back waist region 24 is drawn against the upper alignment conveyor 256 while passing through the seaming section 250, without departing from the scope of this invention. Also, while the seaming section 250 of the illustrated embodiment assembles pre-fastened training pants 20 with the back side panel 134 overlapping the front side panel 34 as shown in FIG. 1, it is understood that the seaming section 250 could be configured so that the front side panel overlaps the back side panel after passing through the seaming section.

The upper alignment conveyor 256 of the illustrated embodiment has an operative width sufficient to draw the full width of the front waist region 22 and front side panels 34 of the training pants 102 against the upper conveyor belt 266 as shown in FIG. 14 fully or partially along the length of the seaming section 250. The lower alignment conveyor 258 is relatively narrow compared to the upper alignment conveyor 256 and has a width, for example, approximately equal to the width of the absorbent chassis 32, and more particularly the absorbent assembly 44. This permits the back side panels 134 to extend laterally out beyond the lower alignment conveyor 258. As another example, the width of the lower alignment conveyor 258 may generally correspond to the distance between the seams 66 (FIG. 2) along which the side panels 34 and 134 are bonded to the absorbent chassis 32.

The respective vacuum pressures acting on the upper and lower alignment conveyors 256, 258 are preferably sufficient to draw and retain the waist regions 22 and 24 of the training pants 102 against the respective conveyors to inhibit pinching of the waist regions between the conveyors. Vacuum control of the waist regions 22, 24 also inhibits lateral movement of the absorbent chassis 32 to thereby improve positioning and alignment of the side panels 34, 134. As an example, the upper alignment conveyor 256 can operate over a range of vacuum pressures, such as about one to about 30 inches of water or greater below atmospheric pressure. The lower alignment conveyor 258 can also operate over a range of vacuum pressures, such as in the range of about one to about 30 inches of water or greater below atmospheric pressure. Suitable conveyor mechanisms such as vacuum conveyors or non-vacuum conveyors are known in the art and available from various commercial vendors and thus will not be further described herein except to the extent necessary to set forth the present invention.

Referring to FIGS. 6 and 11–13, the seaming section 250 further comprises side panel positioning devices, generally indicated at 330, for vertically and laterally positioning the back side panels 134 relative to the front side panels 34; side panel transfer devices, generally indicated at 430, for moving the respective fastening components 84, 82 of the side panels 34, 134 into engagement with each other to define the engagement seams 88; and inspection systems, generally indicated at 520 for inspecting the engagement seams 88 following engagement of the fastening components.

The positioning devices 330 of the illustrated embodiment are mounted on opposite sides of the lower alignment conveyor 258 as shown in FIG. 13, although it is understood that the positioning devices may instead be mounted on the upper alignment conveyor 256 or other suitable frame structure of the seaming section 250. Each positioning device 330 comprises an elongate tubular member 332 extending generally in the machine direction 108 from an upstream end (FIGS. 6, 11) 334 adjacent an upstream end of the seaming section 250 to a downstream end 336. The tubular member 332 of the illustrated embodiment comprises opposed walls 344, 346 (FIG. 14) together defining a generally L-shaped cross-section of the tubular member and an internal flow chamber 340 extending longitudinally therethrough. A slot 342 (FIG. 14) is formed in the tubular member 342 in fluid communication with the internal flow chamber 340 and extends longitudinally substantially the length of the tubular member. The slot 342 faces laterally inward toward the lower alignment conveyor 258 for receiving the back side panel 134 into the internal flow chamber 340 (FIG. 14). The walls 344, 346 of the tubular member 332 may be formed separately and secured together by suitable methods, or they may be formed integrally. It is also understood that the tubular member 332 and internal flow chamber 340 may be other than L-shaped in cross-section without departing from the scope of this invention.

The tubular member 332 can be formed of any suitable material. For example, portions or surfaces of the tubular member 332 which may come into contact with the training pants 102 are desirably formed of a low friction material. Suitable low friction materials or coatings include but are not limited to: stainless steel; low carbon steel; polycarbonate material; Teflon®; aluminum; ultra-high molecular weight polyethylene (UHMW-PE); polyoxymethylene (acetals), for instance a homopolymer available from E. I. Du Pont de Nemours and Company, Wilmington, Del. USA under the tradename DELRIN; or the like.

The flow chamber 340 of the tubular member 332 is in fluid communication with a source of vacuum V via suitable vacuum hoses 350 (FIGS. 6, 11) for drawing fluid, such as air, into the flow chamber via the slot 342 formed in the tubular member such that the fluid flows generally laterally outward within the flow chamber as indicated by the direction arrows in FIG. 14. The vacuum pressure within the flow chamber 340 can vary, for example, from about one to about 20 inches of water or greater below atmospheric pressure, and more particularly from about 2 to about 8 inches of water below atmospheric pressure. It is also contemplated that instead of or in addition to the vacuum pressure, pressurized fluid (not shown) can be directed into the internal chamber 340 via the slot 342 to establish the fluid flow laterally outward within the internal chamber.

The fluid flow within the internal flow chamber 340 is sufficient to draw the back side panel 134 laterally outward relative to the machine center line, and desirably at least partially into the flow chamber, to thereby promote straightening of the back side panel. The slot 342 and the flow chamber 340 are thus desirably sized to accommodate the back side panel 134 and fluid flow therethrough. For example, the slot 342 desirably has a width of about 5 millimeters to about 20 millimeters, and more desirably about 10 millimeters to about 15 millimeters. The walls 344, 346 of the tubular member 332 can converge or diverge relative to one another, or be generally parallel as illustrated. The depth of the flow chamber 340 generally depends upon the application and the amount of back side panel 134 material to be received therein. For example, the internal flow chamber 340 may have a depth of about 10 to about 20 centimeters. As seen best in FIGS. 14 and 15, the tubular member 332 of each positioning device 330 is positioned lower than the lower alignment conveyor 258 so that when the back side panel 134 is drawn into the flow chamber 340, the back side panel extends laterally outward and down from the back waist region 24 being held against the conveyor.

Now referring to FIGS. 11 and 16–18, the side panel transfer devices 430 comprise vacuum conveyors spaced laterally outward of the lower alignment conveyor 258 a distance generally corresponding to the lateral positions of the fastening components 82 of the back side panels 134 as the panels exit the downstream end 336 of the positioning devices 330. More particularly, each side panel transfer device 430 comprises suitable frame structure 432, rotatable pulleys 434 (FIGS. 6 and 11) associated with the frame structure, a vacuum chamber 436 (FIG. 16) defined within the frame structure, a vacuum cover plate 438 (FIG. 16) mounted on the frame structure, and a continuous belt 440 carried by the pulleys. A drive mechanism (not shown) and corresponding conveyor shaft (not shown) can be used to rotatively drive one or more of the pulleys 434. The side panel transfer devices 430 can be aligned parallel to the machine direction 108 as shown in FIG. 13 or canted inward or outward, for example, to improve side panel 34, 134 alignment with the machine direction.

Each side panel transfer device 430 angles up toward the pants transport plane defined by the upper and lower alignment conveyors 256, 258 as the device extends in the machine direction 108 from an upstream end 442 disposed slightly upstream and below the downstream end 336 of the positioning device 330, to a downstream end 444 disposed in closely spaced relationship with the upper alignment conveyor 256. The side panel transfer device 430 and the upper alignment conveyor 256 thus define a nip therebetween at the downstream end of the device, the purpose of which will become apparent.

The side panel transfer device 430 can alternatively comprise other devices (not shown) for sequentially or simultaneously affecting upward movement of the laterally outward portion of the back side panel 134. By way of illustration, suitable side panel transfer devices 430 can alternatively comprise disks or wheels, either aligned in the machine direction 108 or canted and/or tilted relative thereto so that the disks or wheels raise the side panels and nip the fasteners together. Suitable wheel devices can, but need not, be timed elliptical wheels, and can comprise vacuum or traction surface wheels or the like. Still alternatively, the side panel transfer devices 430 can comprise 4-bar linkage mechanisms carrying a panel engagement head which contacts the back side panel 134 to raise the panel relative to the plane of the lower alignment conveyor 258. The rotary motion provided by the 4-bar linkage can allow the panel engagement head to raise a back side panel 134 relative to the lower alignment conveyor 258, with the back side panel being allowed to slip off the inward edge of the panel engagement head. A drive mechanism for the 4-bar linkage can be programmed to vary the angular velocity of the panel-engagement head such that its velocity in the machine direction 108 matches the speed of the back side panel 134 while the panel-engagement head is in contact with the back side panel. Alternatively, the angular velocity of the panel-engagement head can be matched with the velocity of the side panel using a cam gearbox, non-circular gearing, or the like. Such devices could further comprise a feedback system to register the panel-engagement head to the back side panel 134. In yet another alternative embodiment, the side panel transfer devices 430 can comprise folding boards or folding skis to provide sequential or simultaneous inward and upward relative movement of the laterally outward portions of the back side panels 134 and the fastening components 82.

Other suitable side panel positioning devices 330 and side panel transfer devices 430 are disclosed in co-assigned U.S. application Ser. No. 10/010110, which was filed Nov. 13, 2001 by Tomsovic et al. and titled "Fluid Flow Device and Method for Positioning Garment Side Panels," the entire disclosure of which is incorporated herein by reference.

Figure 17:
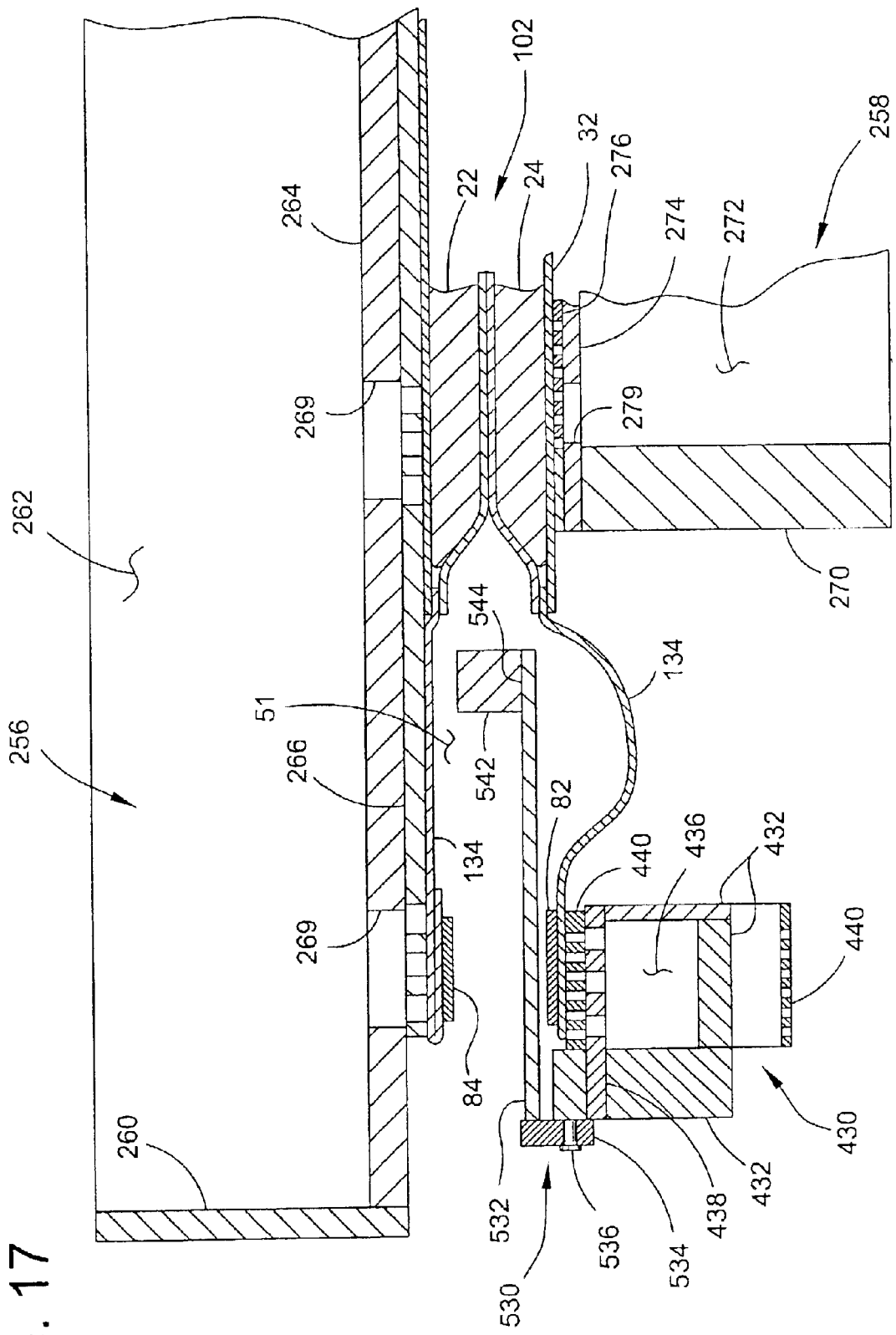
FIG. 17 is a partial section taken in the plane of line 17—17 of FIG. 11.

Now referring to FIGS. 12, 13 and 17–23, each inspection system 520 comprises a support assembly, generally indicated at 530, for supporting the front and back side panels 34, 134 in a generally expanded configuration to facilitate inspection of the engagement seam 88. The support assembly 530 comprises a rectangular plate 532 (FIGS. 17 and 22) mounted on the side panel transfer device 430 by a suitable mounting member 534 (FIG. 17) and fasteners 536. The rectangular plate 532 is oriented generally parallel to the pants transport plane defined by the upper and lower alignment conveyors 256, 258 (e.g., generally horizontal in the illustrated embodiment). A leading edge 538 (FIG. 13) of the plate 532 is disposed just downstream from the upstream end 442 of the transfer device 430 and terminates at a trailing edge 540 of the plate upstream of the downstream end 444 of the transfer device. As best seen in FIG. 17, the rectangular plate 532 also extends laterally inward toward the machine center line above the transfer device 430 (and hence above the back side panel 134 supported by the transfer device) to separate the fastening components 82, 84.

An elongate bar 542 is connected to the upper surface of the rectangular plate 532 as shown in FIGS. 17 and 23, such as by overlaying an inner edge margin 544 thereof and being secured to the plate by welding or suitable fasteners (not shown). The bar 542 extends in the machine direction 108 downstream beyond the trailing edge 540 of the plate 532 to a downstream end 546 (FIGS. 13, 23) of the bar. The bar 542 has a channel 545 formed in the outer side thereof and extending downstream from the trailing edge 540 of the rectangular plate 532 to the downstream end 546 of the bar. As an example, the bar 542 of the illustrated embodiment has a width of about 0.375 inches and a height of about 0.375 inches. It is understood, however, that the cross-sectional dimensions of the bar 542 may be larger or smaller, and that the cross-section of the bar may be circular, I-shaped, T-shaped or other suitable shape without departing from the scope of this invention.

Figure 18:
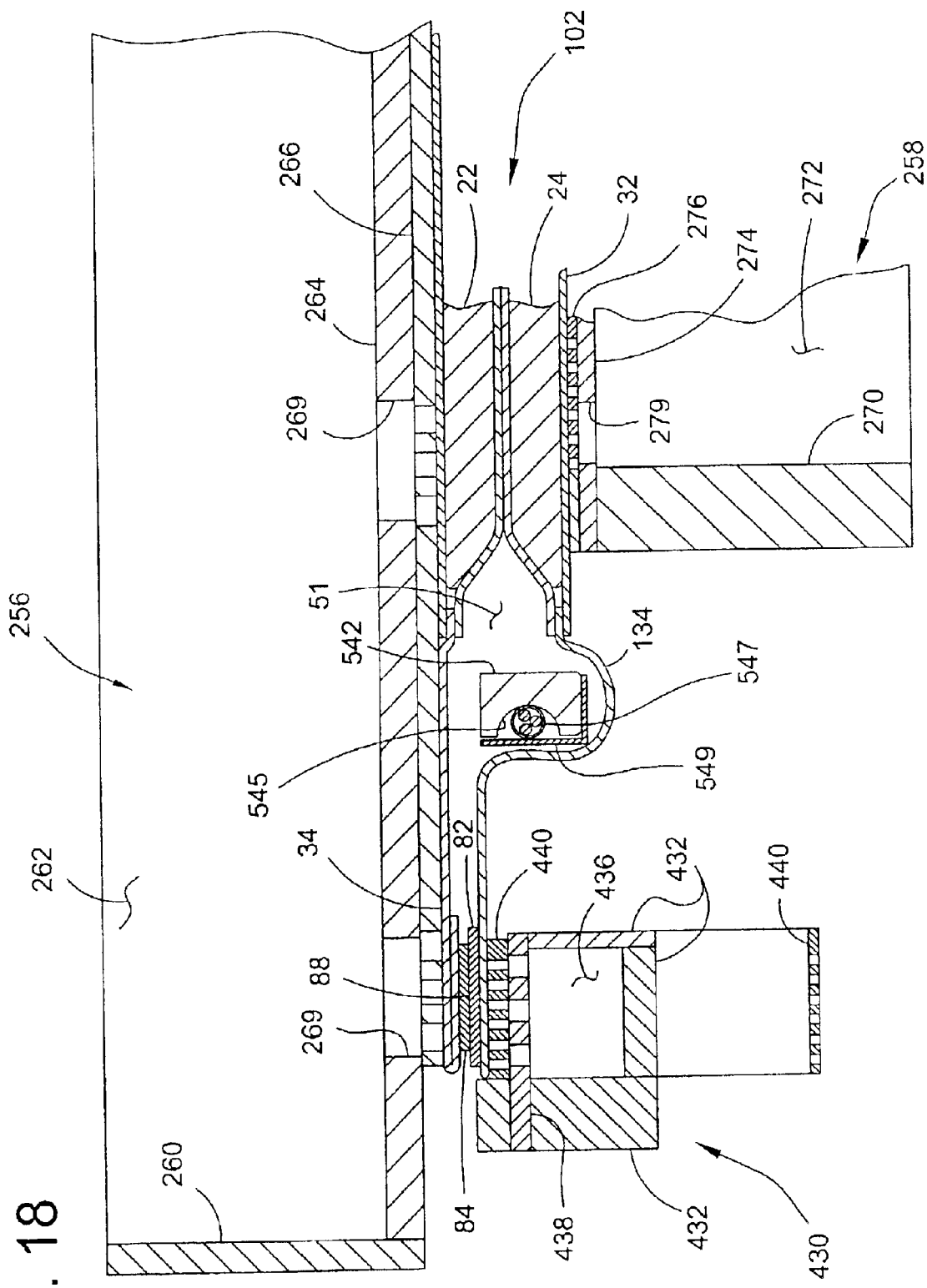
FIG. 18 is a partial section taken in the plane of line 18—18 of FIG. 11.

The bar 542 is disposed higher than the lower alignment conveyor 258 for positioning within the interior space 51 of the pants 102 between the front and back side panels 34, 134 upon conveyance of the training pants in the machine direction 108 over the bar. The bar 542 is also positioned laterally between the lower alignment conveyor 258 and the side panel transfer device 430 for interposition between the absorbent chassis 32 and the engagement seam 88 following connection of the fastening components 82, 84 as shown in FIG. 18 and described later herein. As best seen in FIGS. 17, 18 and 23, a cable 547 extends longitudinally within the channel 545 and is in electrical communication with an inspection system control (not shown) which controls operation of the inspection system 520 to inspect the engagement seam 88. An elongate channel cover 549 having a generally L-shaped cross-section is secured to the bar 542 by suitable fasteners (not shown) to cover the channel 545 formed therein to thereby enclose the cable within the channel. However, it is contemplated that the bar 542 may instead be of unitary construction and have a passage extending longitudinally therethrough for receiving the cable.

With particular reference to FIGS. 13, 22 and 23 an elongate support member 548 is mounted on the bar 542 generally at the downstream end 546 thereof and has an upstream end 550 spaced longitudinally (e.g., in the machine direction 108) from the downstream end 444 of the side panel transfer device 430. More particularly, the support member 548 comprises a top wall 552 having an inner edge margin 554 (FIG. 20) which overlays the bar 542 and is secured thereto by suitable fasteners (not shown). The top wall 552 of the support member 548 extends laterally out from the bar 542 generally parallel to the pants transport plane defined by the upper and lower alignment conveyors 256, 258 (which in the illustrated embodiment is horizontal).

Figure 20:
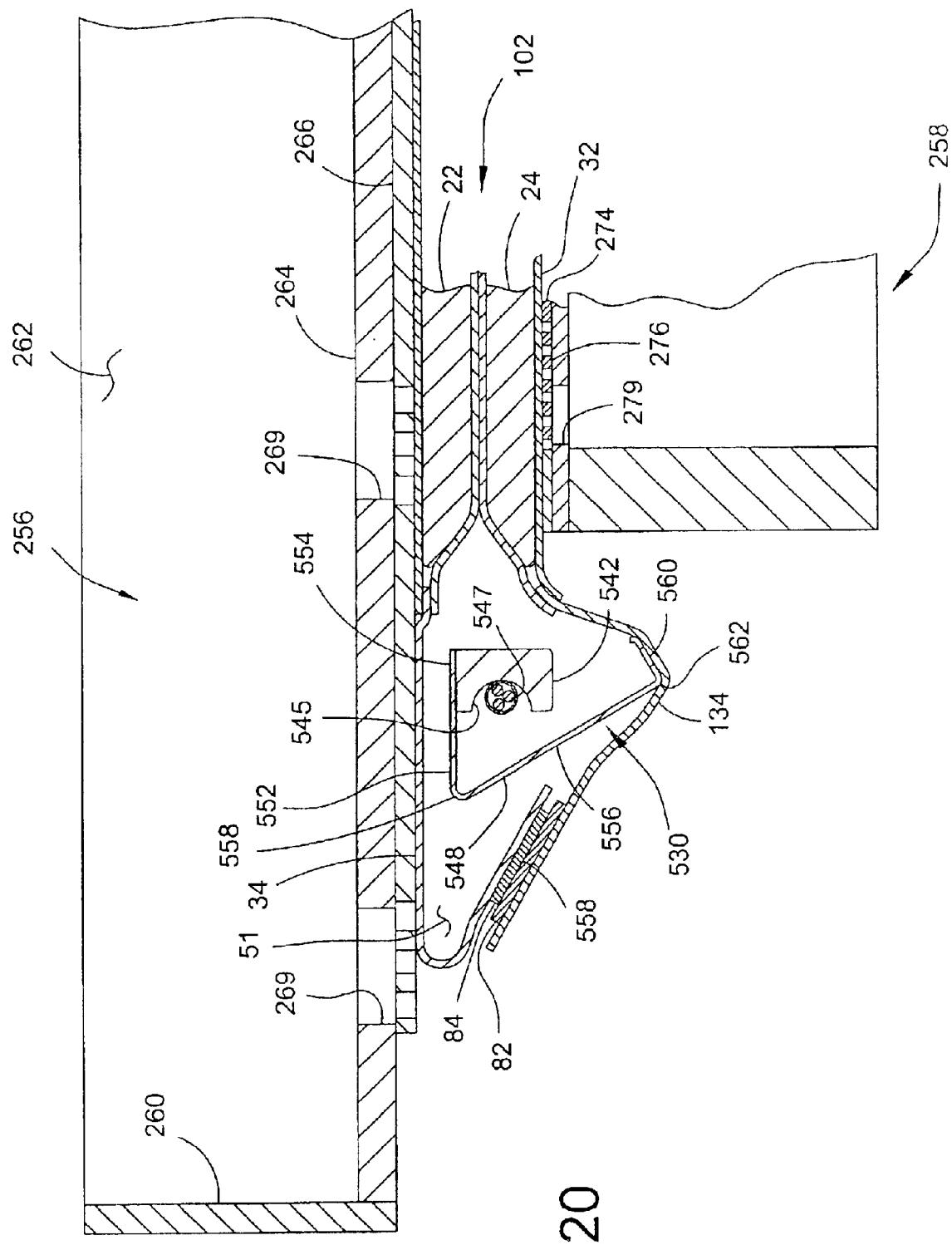
FIG. 20 is a partial section taken in the plane of line 20—20 of FIG. 12.

An outer side wall 556 (FIGS. 20, 22) is secured to the outer edge of the top wall 552, such as by being formed integrally therewith, to define an upper corner 558 of the support member 548 and depends from the top wall generally inward at an angle relative thereto. The cross-section of the support member 548 is thus generally V-shaped, and is more particularly the shape of the numeral "7." As an example, the outer side wall 556 desirably forms an angle with the top wall 552 in the range of about 50° to about 65°. However, it is understood that the angle formed by the outer side wall 556 and the top wall 552 may be less than 50° or greater than 65°; such as between 0° and 180° without departing from the scope of this invention. A bottom wall 560 is secured to the lower edge of the side wall 556, such as by being formed integrally therewith, to define a lower corner 562 of the support member 548 and extends generally inward and up from the side wall toward the lower alignment conveyor 258. However, it is contemplated that the bottom wall 548 may be omitted without departing from the scope of this invention. As shown in FIG. 20, the upper and lower corners 558, 562 of the support member 548 are desirably rounded to inhibit tearing of the front and back side panels 34, 134 as the side panels are conveyed over the support member.

As best seen in FIGS. 6, 12 and 13, the support member 548 has a tapered lead portion 564 which gradually increases in cross-sectional dimension as the support member extends from its upstream end 550 where the cross-sectional dimension of the support member corresponds generally to that of the bar 542 to a main portion 566 of the support member along which its cross-sectional dimension is generally uniform. As an example, the main portion 566 of the support member 548 of the illustrated embodiment has a width of about 0.25 to about 3 inches and a height of about 0.25 to about 4 inches. As an additional example, the support member 548 is approximately 15.25 inches in length, with the lead portion 564 being about 5.5 inches long and the main portion 566 being about 9.75 inches long.

The support member further comprises an inner side wall 563 (FIGS. 21–23) which extends between the top wall 552 and the bottom wall 560 in generally parallel spaced relationship with the outer side wall 556 along the length of the main portion 566 of the support member 548 to define a channel 565 therebetween. For example, the support member channel 565 of the illustrated embodiment is approximately 0.5 inches wide. An upper portion 567 of the inner side wall 563 extends laterally beneath the top wall 552 of the support member 548 to between the top wall and the support assembly bar 542 such that the inner side wall is secured to the bar by the same fasteners (not shown) which secure the top wall to the bar.

The support member 548 is supported by the bar 542 for positioning within the interior space 51 of the training pants 102 generally vertically between the portions of the front and back side panels 34, 134 extending on opposite sides of the engagement seam 88 as the pants are conveyed in the machine direction 108 over the support member. The lower corner 562 of the support member 548 along the main portion 566 thereof is disposed substantially below the lower alignment conveyor 258 (and hence below the back waist region 24 of the absorbent chassis 32). The support member 548 is also supported for positioning laterally out from the lower alignment conveyor 258, between the absorbent chassis 32 and the engagement seam 88. It is contemplated that the vertical and/or lateral position of the support member 548 relative to the lower alignment conveyor 258 may vary to adjust the positioning and relative expansion of the side panels 34, 134 as the pants 102 are conveyed over the support member in the manner to be described. However, the lateral spacing of the support member 548 from the lower alignment conveyor 258 is desirably sufficient to inhibit pinching or binding of the back side panel 134 therebetween.

Figure 21:
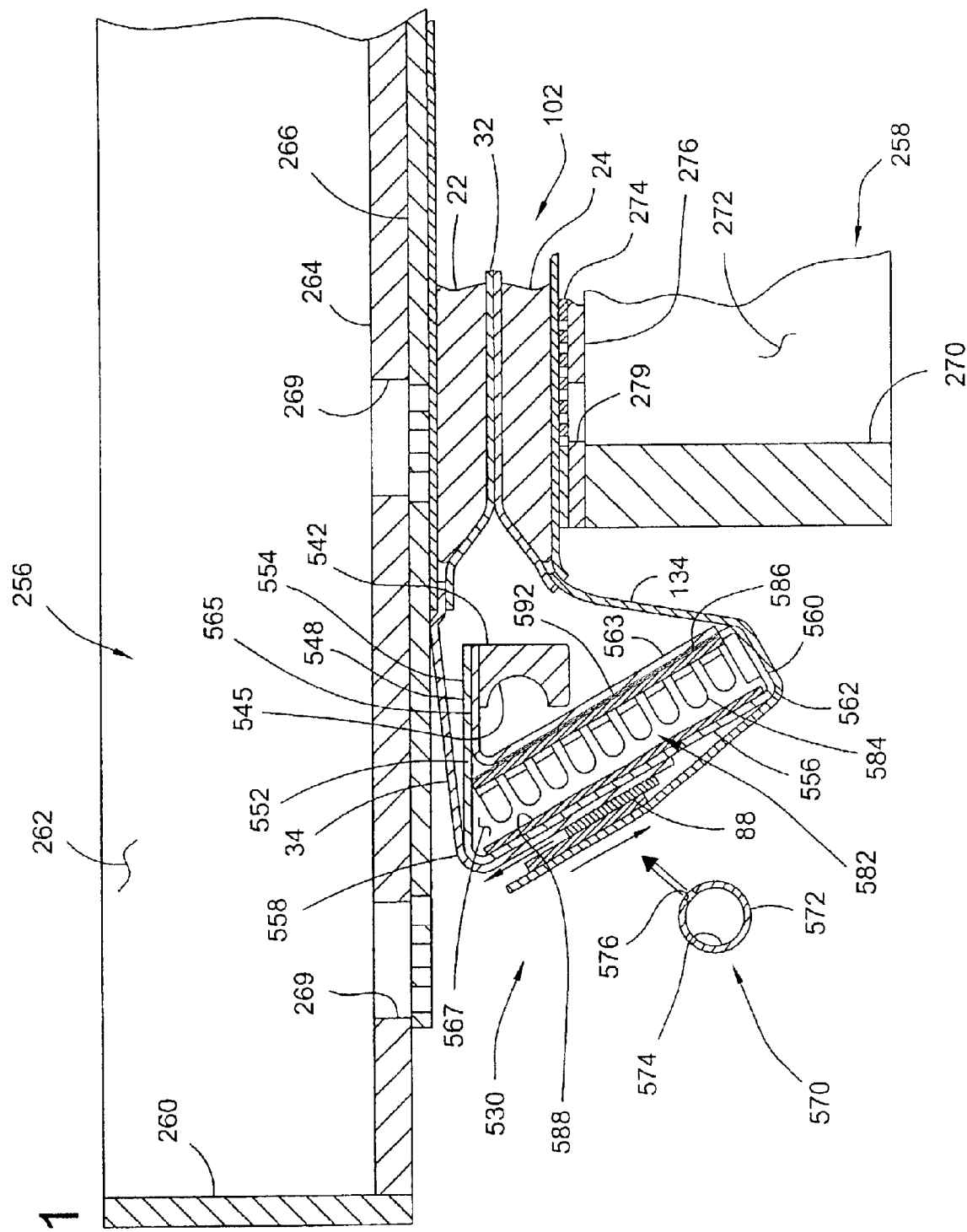
FIG. 21 is a partial section taken in the plane of line 21—21 of FIG. 12.

In the illustrated embodiment, the inspection system 520 also comprises an air bar (broadly, a fluid delivery device), generally indicated at 570 (FIGS. 6, 12 and 21), extending longitudinally in parallel spaced relationship with the main portion 566 of the support member 548 at a position which is generally lower than and laterally outward of the lower corner 562 of the support member. The air bar 570 comprises an elongate, cylindrical tube 572 in fluid communication with a source (not shown) of pressurized fluid, such as air, for receiving pressurized air within an internal passage 574 (FIG. 21) of the tube. Exhaust openings 576 (one of which is shown in FIG. 21) are formed in the side wall of the tube 572 in longitudinally spaced relationship with each other along the length of the tube. The exhaust openings are located on an upward and slightly inward facing portion of the side wall to direct pressurized fluid exhausted from the tube toward the outer side wall 556 of the support member 548 for impacting at least one of the front and back side panels 34, 134 at the engagement seam 88 to thereby urge the engagement seam 88 to lay generally flat on the outer side wall of the support member.

As an example, the air bar 570 of the illustrated embodiment has a length of about 9.75 inches, an internal diameter of about 0.5 inches and exhaust openings 576 each having a diameter of about 0.05 inches and spaced about one inch apart along the length of the air bar. Pressurized fluid received by the air bar 570 and exhausted therefrom toward the side wall 556 of the support member 548 is desirably in the range of about 10 psi to about 40 psi. It is understood that the air bar 570 may be positioned other than below and outward of the lower corner 562 of the support member 548, as long as pressurized fluid exhausted from the air bar is directed generally inward toward the side wall 556 of the support member. It is also contemplated that the air bar 570 may be omitted without departing from the scope of this invention. Instead of an air bar 570, the fluid delivery device may instead be a nozzle (not shown), an air knife (not shown) or other suitable device for directing pressurized fluid to impact the side panels 34, 134 at the engagement seam 88.

In the illustrated embodiment, the inspection system 520 further comprises a radiation source, generally indicated at 582 in FIGS. 21–23, disposed within the support member channel 565 formed by the inner and outer side walls 563, 556 of the support member 548 for positioning within the interior space 51 of the pants 102 as the pants are conveyed in the machine direction 108 over the support member. The radiation source 582 of the illustrated embodiment is an infrared radiation source capable of emitting radiation in the near infrared/infrared spectrum (i.e., radiation having a wavelength between about 700 nanometers and one millimeter). More desirably, the infrared radiation source 582 emits radiation in the range of about 700 to about 1200 nanometers. As an example, the radiation source 582 shown in FIGS. 21–23 comprises an array of infrared LED's 584 mounted on a circuit board 586. The LED's 584 are each about 3 mm to about 5 mm in length and capable of emitting infrared radiation at a wavelength of about 940 nanometers. As an additional example, the radiation source 582 of the illustrated embodiment is about 8.52 inches long, about 1.71 inches wide and comprises about 432 infrared LED's. One such radiation source 582 is available from RVSI of Weare, N.H., U.S.A. as part number 010-904504.

It is contemplated that certain zones (not shown) of the radiation source 582 may emit radiation at a different intensity level or wavelength than other zones. For example, with reference to the radiation source 582 illustrated in FIG. 23, one or more groupings of the LED's 584, such as those disposed generally toward the longitudinal ends of the radiation source, may generate infrared radiation at a lower intensity level than the remaining LED's disposed longitudinally central of the radiation source. Various configurations and operation of a radiation source 582 having multiple zones of varying radiation intensity are described in co-assigned U.S. application entitled "Apparatus and Method for Making and Inspecting Pre-Fastened Articles," which is incorporated herein by reference. It is also understood that the radiation source 582 for emitting infrared radiation may instead comprise mercury vapor lamps, argon lamps, arc lamps, lasers and other suitable radiation emitting devices without departing from the scope of this invention. Also, the radiation source 582 may instead, or may additionally, emit visible and/or ultraviolet radiation. For example, one such radiation source is a fiber optic light source which emits radiation in the range of about 400 to about 700 nanometers using a tungsten or halogen bulb and is available from E.G. & G., Electro-Optics of Salem, Mass., U.S.A.

The radiation source 582 is in electrical communication with the inspection system control via the cable 547 and may be operated by the control to emit radiation either intermittently or continuously. For example, the inspection system control may operate the radiation source 582 to emit radiation therefrom intermittently in response to the engagement seam 88 of the training pants 102 being conveyed in the machine direction 108 over the support member 548.

Referring particularly to FIG. 23, the support member 548, including the top wall 552, the inner and outer side walls 563, 556 and the bottom wall 560 are generally constructed of metal, and more desirably steel. However, a rectangular portion of the outer side wall 556 of the support member 548 is constructed of a material which permits the transmission therethrough of radiation emitted by the radiation source 582. More particularly, the outer side wall 556 partially comprises a diffuser plate 588 constructed of a material which diffuses radiation emitted by the radiation source 582 as radiation is transmitted out through the diffuser plate. The diffuser plate 588 of the illustrated embodiment is generally rectangular and is received in a rectangular opening 590 of the outer side wall 556 in generally flush alignment therewith. The thickness of the diffuser plate 588 is desirably in the range of about 0.125 inches to about 0.375 inches. However, it is understood that the material from which the diffuser plate 588 is constructed, as well as the thickness of the diffuser plate, may vary depending on the radiation source 582 and the desired diffusion of radiation emitted by the radiation source. As an example, the illustrated diffuser plate 588 for diffusing infrared radiation emitted by the radiation source 582 is approximately 9.75 inches long, 1.94 inches wide and has a thickness of about 0.125 inches. One suitable material from which the diffuser plate 588 may be constructed is available from Quadrant Engineering Plastics Products, Inc. of Reading, Pa., U.S.A. under the tradename ACETRON® GP.

An insulating sheet 592 (FIG. 23) constructed of an electrically insulating material is positioned between the circuit board 586 of the radiation source 582 and the inner side wall 563 of the support member 548 to electrically isolate the radiation source from the support member. For example, the insulating sheet 592 of the illustrated embodiment is constructed of plastic and has a thickness of about 0.008 inches.

An image capturing device, generally indicated at 594 (FIGS. 13 and 24), of the inspection system 520 is mounted on suitable frame structure 596 for positioning exterior of the training pants 102 as the pants are conveyed in the machine direction 108 over the support member 548 and radiation source 582. In the illustrated embodiment, the image capturing device 594 is mounted on the frame structure 596 by an adjustable mounting assembly, generally indicated at 598, to permit selective adjustment of the device position and orientation relative to the support member 548, such as in the machine direction and in the cross-machine direction. However, it is understood that the image capturing device 594 may instead be secured to the frame structure 596 against movement relative to the support member 548 without departing from the scope of this invention.

The image capturing device 594 of the illustrated embodiment is aimed generally toward the support member 548, and is more particularly aimed toward the outer side wall 556 of the support member along a sight line (not shown) which is generally perpendicular to the outer side wall. The device 594 is desirably operable to detect infrared radiation transmitted by the radiation source 582 through the diffuser plate 588 and the front and back side panels 34,134 at the engagement seam 88 and to produce a two-dimensional image of the engagement seam. As a result, the captured image will include variations therein which correspond to variations in radiation intensity (and/or wavelengths) detected by the device 594 from exterior of the pants 102 (e.g., looking at the outside of the engagement seam 88). In one embodiment, the image produced by the device 594 is a black-and-white image in which radiation level variations are depicted in varying grayscale levels. Alternatively, such variations may be depicted in the image in another manner, such as in the form of color variations. The image capturing device 594 is in electrical communication with the inspection system control and may be operated continuously or it may be shuttered at a speed corresponding to the intermittent operation of the radiation source 582 to irradiate the engagement seam 88.

The image capturing device 594 shown in FIG. 24 is a vision inspection camera capable of detecting visible and ultraviolet radiation as well as infrared radiation at wavelengths up to about 1200 nanometers. For example, one such device 594 is a charge coupled device ("CCD") vision camera available from Sony Corporation of Japan under the model designation XC-75/73. However, it is understood that other image capturing devices may used, such as line scan cameras capable of building an image one line at a time from detected radiation as the pants 102 are is conveyed past the device, as well as any other device capable of producing a one, two or three dimensional image from detected radiation, without departing from the scope of this invention.

The image capturing device 594 may also be provided with a filter (not shown) for filtering unwanted wavelengths of radiation, including those in the infrared and/or other spectrums, as desired. Such filters include low-pass filters which remove radiation above a predefined wavelength, high-pass filters which remove radiation below a predefined wavelength, band-pass filters which remove all radiation except that having a wavelength within a predefined range, and combinations thereof. One or more of these filters may be useful for removing ambient, scattered, or even incident radiation from the image captured by the image capturing device 594. For example, the image capturing device 594 of the illustrated embodiment for detecting infrared radiation is desirably provided with a filter for removing (i.e., blocking) radiation, such as ambient and/or scattered radiation, having a wavelength of or below about 830 nanometers (e.g., a high pass filter having a nominal value of about 830 nanometers), including visible and ultraviolet radiation. Alternatively (or additionally), one or more shrouds (not shown) may surround the device 594 to shield the device from, e.g., extraneous radiation sources such as ceiling lights, natural light, etc.

Figure 19:
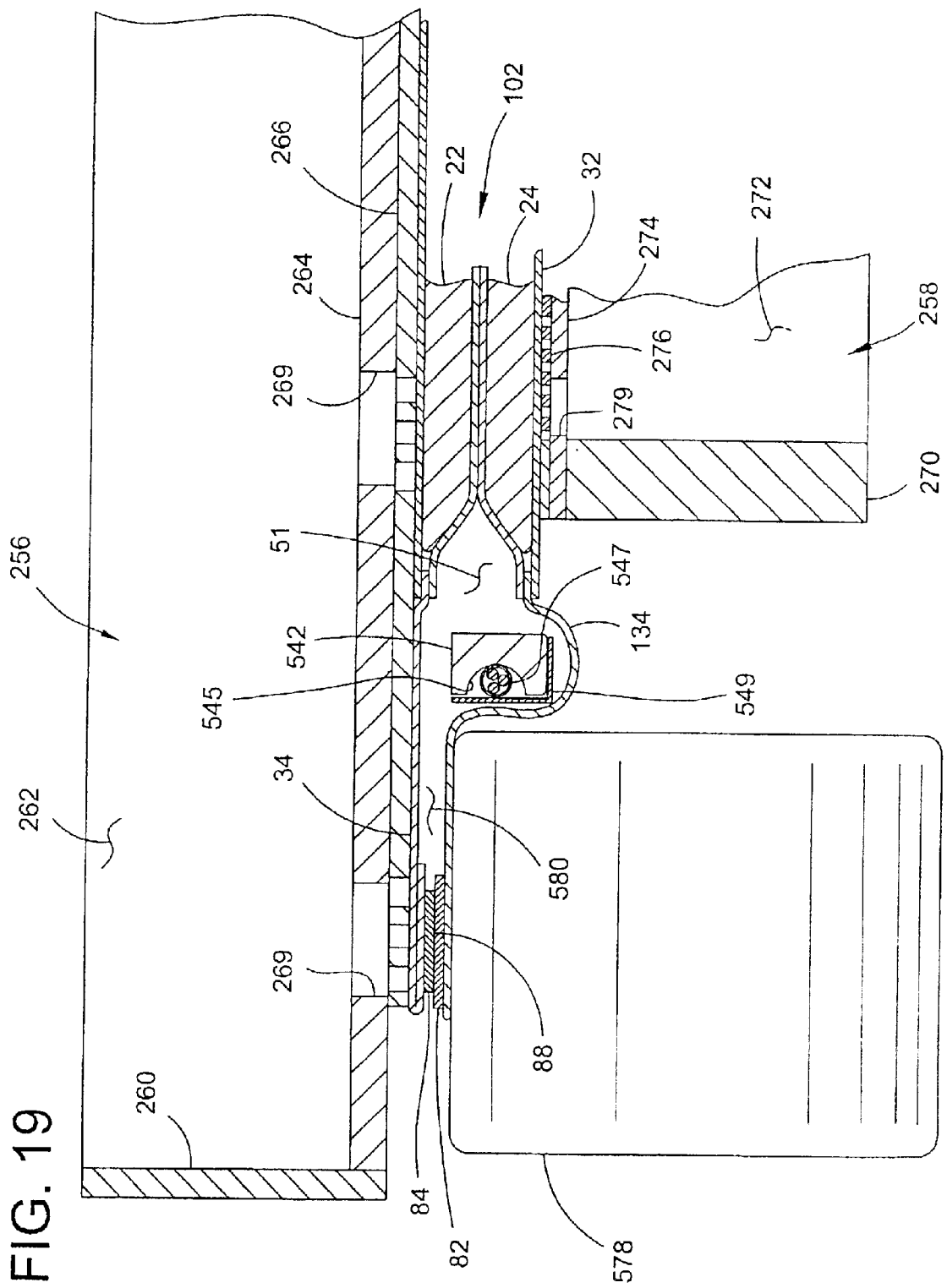
FIG. 19 is a partial section taken in the plane of line 19—19 of FIG. 12.

Now referring back to FIGS. 13 and 19, the seaming section 250 further comprises a pair of rollers 578 mounted for rotation on respective axles (one of which is shown in FIG. 12 and indicated at 579). Each of the axles is supported by a lever arm 581 which is pivotably mounted on the lower alignment conveyor 258 immediately downstream of the side panel transfer devices 430, e.g., between the downstream ends 444 of the side panel transfer devices and the upstream ends 550 of the tensioning members 548. The rollers 578 are sized and positioned vertically for close contact relationship with the upper alignment conveyor 256 to define contact nips 580 (one of which is shown in FIG. 19) therebetween through which the engagement seams 88 pass following initial engagement of the respective fastening components 84, 82 of the side panels 34, 134. Each lever arm 581 is operatively connected to a respective suitable pneumatic device 583 which biases the roller 578 into contact with the upper alignment conveyor 258. As an example, the rollers 578 of the illustrated embodiment have an outer diameter of about three inches and a face (e.g., width) of about 2.75 inches.

The lever arm 581 supporting the roller 578 is pivotable to allow pivoting of the roller down away from the upper alignment conveyor as the side panels 34, 134 are conveyed through the contact nip 580. The pneumatic pressure which biases each roller 578 toward the upper alignment conveyor 258 is desirably sufficiently low to permit the side panels 34, 134 to urge the roller to pivot down away from the upper alignment conveyor upon passing through the contact nip 280, but sufficiently high to urge the fastening components 82, 84 together at the engagement seam 88. For example, the pneumatic pressure of the device 583 is such that the pressure of the roller 578 against the upper alignment conveyor 258 (and hence the fastening components 82, 84 as they pass therebetween) is in the range of about 1 to about 50 lbs., and more desirably in the range of about 5 to 20 pounds. It is understood, however, that the rollers 578 may be omitted altogether without departing from the scope of this invention. It is also contemplated that the rollers 578 may instead be maintained in spaced relationship with the upper alignment conveyor 258, such as in the range of about zero to about 5 mm, to define the nips 280. A corresponding roller (not shown) is disposed within the upper alignment conveyor 258 in contact with the conveyor belt 266 and in opposed relationship with the rollers 578 to provide a corresponding bearing surface for the rollers 578.

In operation, the partially assembled and folded training pants 102 are received from the folding section 200 into the upstream end of the seaming section 250 generally in the configuration shown in FIG. 10, e.g., with the front waist region 24 of the absorbent chassis 32 folded over the back waist region 22 and the front and back side panels 34, 134 extending laterally out from the front and back waist regions. At the downstream location shown in FIG. 14, the front side panel 34 is drawn against the upper alignment conveyor 256 in an outstretched configuration, with the fastening component 84 of the front side panel facing up toward the upper alignment conveyor. An outer portion of the back side panel 134 is drawn through the slot 342 of the positioning device 330 into the internal flow chamber 340 thereof.

Figure 15:
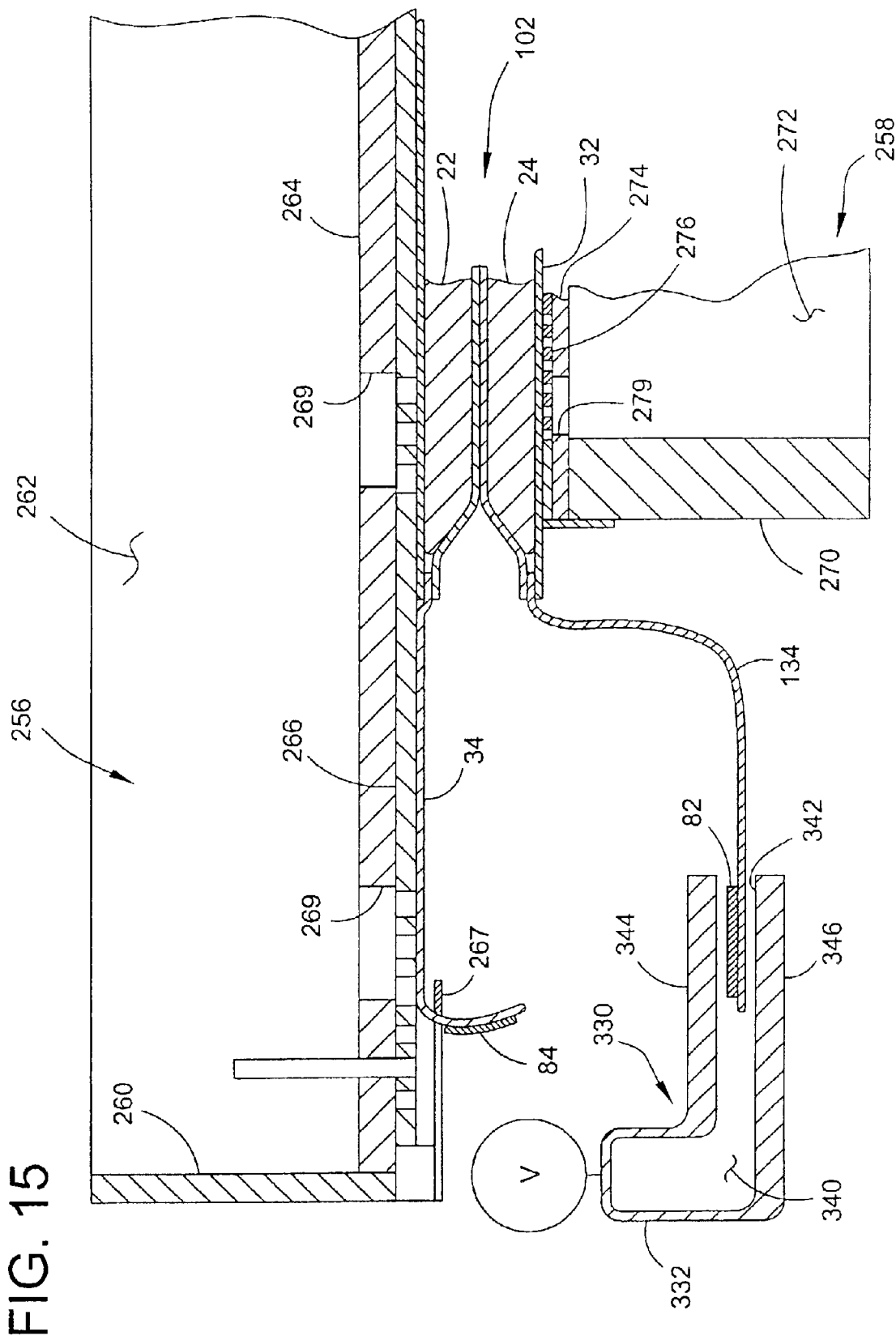
FIG. 15 is a partial section taken in the plane of line 15—15 of FIG. 11.

Further downstream, such as the location illustrated in FIG. 15, the positioning device 340 has repositioned the back side panel 134 such that the fastening component 82 is laterally nearer the machine centerline. Vacuum is inhibited from drawing a laterally outward portion of the front side panel 34, including the fastening component 84, against the upper alignment conveyor, such as by closing off laterally outer holes 269 of the vacuum cover plate 264. As a result, the laterally outward portion of the front side panel 34 tends to drop, due to gravity, away from the upper alignment conveyor 256 and folds over a folding finger 267. Alternatively, the upper alignment conveyor 256 can provide a uniform or nonuniform vacuum profile in the cross machine direction. In particular embodiments, the upper alignment conveyor 256 can draw a nonuniform vacuum in the cross-machine direction. Specifically, the upper alignment conveyor 256 can draw a concentrated vacuum at laterally outward regions as well as some area of vacuum in a central region disposed between the laterally outward regions. The laterally outward regions can be positioned such that they correspond to locations of the front side panels 34 immediately laterally inward from the locations of the fastening components 84. The concentrated vacuum adjacent the inside edge of the fastening components 84 can encourage the inside edge thereof to generally function as a hinge point for folding. The concentrated vacuum can be formed by a plurality of slots or an increase in the number of apertures in the vacuum cover plate 264, by separate vacuum chambers, or the like. The focused vacuum in the central region can reduce energy consumption and lessen draw of the back side panels 134 toward the upper alignment conveyor 256.

Figure 16:
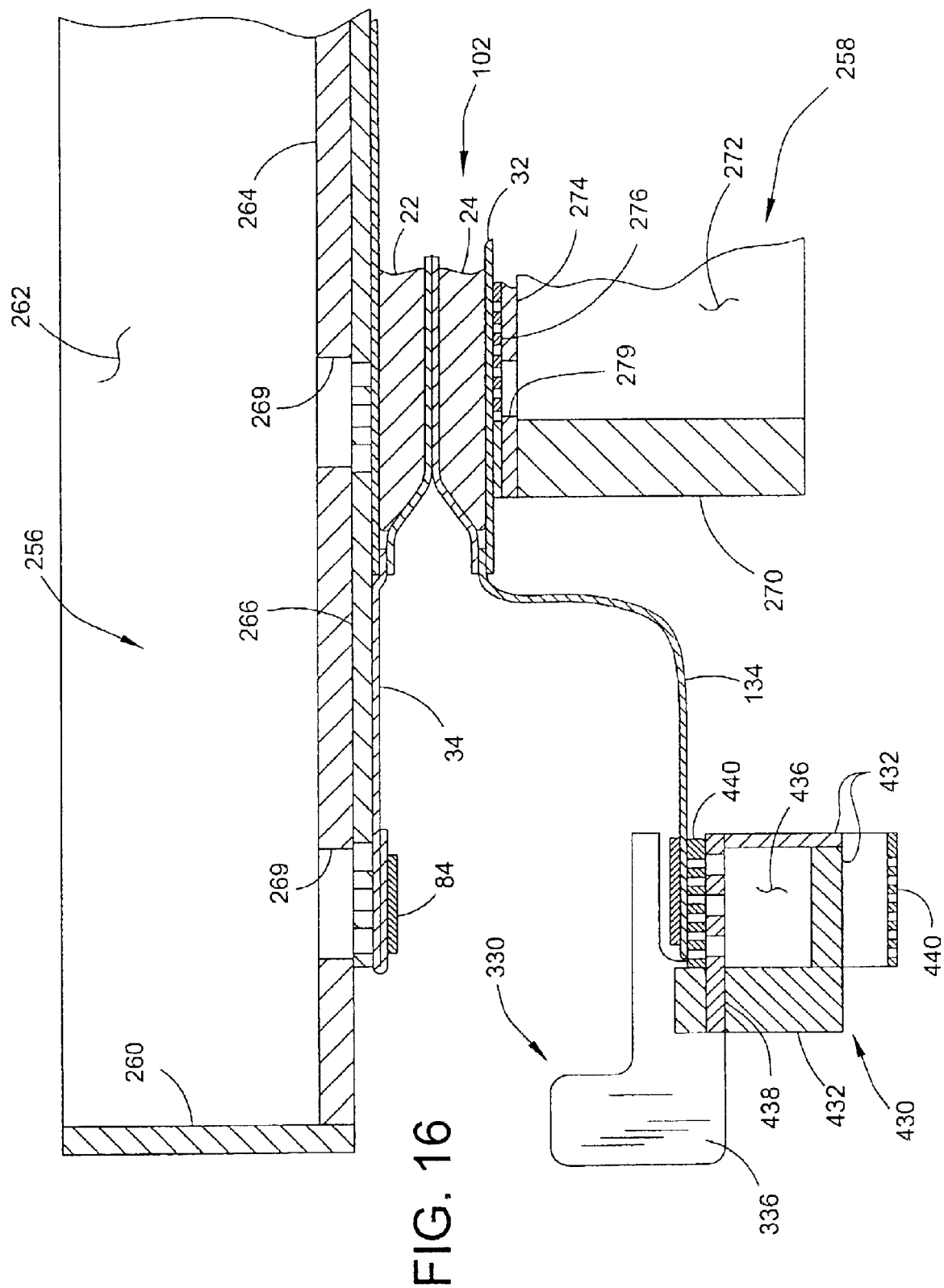
FIG. 16 is a partial section taken in the plane of line 16—16 of FIG. 11.

Upon reaching the location shown in FIG. 16, the laterally outward portion of the front side panel 34 has been folded through approximately 180 degrees by a suitable panel folding device (not shown) such that the fastening component 84 of the front side panel is now facing down in generally opposed relationship with the fastening component 82 of the back side panel 134. The panel folding device (not shown) acts on the laterally outward portion of the front side panel 34 after the panel is folded down over the folding finger 267 and can comprise, for example, one or more air nozzles (not shown) which blow the laterally outward portion of the front side panel 34, including the initially outward-facing fastening component 84, to a horizontal orientation directed toward the center line of the upper alignment conveyor 256. The panel folding device can operate on a continuous or timed intermittent basis, and can progressively fold the side panel 34 or fold the side panel as a single unit. The panel folding device can alternatively comprise other mechanisms for creating a suitable force to fold or assist to fold the front side panel 34. For example, the panel folding device can comprise folding boards or skis which fold the front side panel through 180 degrees; a helical surface that pushes the front side panel into the folded configuration; or the like. Once folded inward, the folded portion of the front side panel 34, including the fastening component 84, is drawn against the upper alignment conveyor to maintain the folded configuration of the front side panel.

The side panel transfer device 430 intersects the downstream end 336 of the positioning device 330 such that the portion of the back side panel corresponding to the fastening component 82 is supported by the side panel transfer device as the back side panel exits the positioning device. At this location, the fastening components 82, 84 are in opposed, vertically spaced relationship with each other. The side panel transfer device 430 elevates the fastening component 82 of the back side panel 134 generally in a "z-direction" perpendicular to the machine direction 108 while the remaining extent of the back side panel hangs generally limp between the lower alignment conveyor 258 and the transfer device. Further downstream, as shown in FIG. 17, the fastening component 82 of the back side panel 134 has been elevated further up toward the fastening component 84 of the front side panel 34. The support plate 532 of the tensioning assembly 530 extends inward from the side panel transfer device 430 over the back side panel 134 to separate the fastening components 82, 84.

Finally, upon reaching the downstream end 444 of the side panel transfer device 430 (FIG. 18), the fastening component 82 of the back side panel 134 has been elevated into engagement with the fastening component 84 of the front side panel 34 to define the engagement seam 88. As a result, the interior space 51 of the pants is now bounded in part by the engagement seam 88 and in part by the opposed portions of the front and back side panels extending on opposite sides of the engagement seam. The support assembly bar 542 is thus positioned within the interior space 51 of the pants 102 generally vertically between the front and back side panels 34, 134 and laterally between the lower alignment conveyor 258 and the engagement seam 88 upon connection of the fastening components 82, 84. The connected fastening components 82, 84 are urged together upon passing between the nip defined by the downstream end 444 of the transfer device 430 and the upper alignment conveyor 256 to facilitate increased engagement between the fastening components as the training pants 102 are conveyed further downstream. The training pants 102 are then transported downstream past the roller 578 whereby the engaged fastening components 82, 84 pass through the nip 580 between the roller and the upper alignment conveyor 256 as shown in FIG. 19 to further urge the fastening components together.

Downstream of the nip 580, the pair of training pants 102 is transported past the upstream end 550 of the support member 548. FIG. 20 illustrates the side panels 34, 134 at a location along the tapered lead portion 564 of the support member 548. At this location, vacuum drawing the folded portion of the front side panel 34 to the upper alignment conveyor 256 is substantially reduced to release the fastening component 84 from being drawn toward the upper alignment conveyor. As a result, the fastening component 84 of the front side panel 34 hangs down from the upper alignment conveyor 256 and supports the back side panel 134 in a generally limp configuration via engagement between the fastening components 82, 84. In the illustrated embodiment, the back side panel 134 contacts the bottom wall 560 and lower corner 562 of the support member 548 at the tapered lead portion 564 thereof and is positioned substantially below the lower alignment conveyor 256 and the back waist region 24 of the absorbent chassis 32. However, it is contemplated that the back side panel 134 may hang down below the tapered lead portion 564 of the support member 548 at the location shown in FIG. 20.

Finally, the training pants 102 are conveyed further downstream over the main portion 566 of the support member 548 as shown in FIG. 21. Based on the vertical and lateral positioning of the support member 548 relative to the upper and lower alignment conveyors 256, 258 (and hence the absorbent chassis 32), as well as the orientation and cross-sectional dimensions of the main portion 566 of the support member, the front and back side panels 34, 134 contact the support member and are generally expanded (e.g., pulled or otherwise spaced apart) outward, such as laterally and/or vertically, relative to the absorbent chassis and pulled taut around the support member.

More particularly, the front side panel 34 is expanded by the support member to extend laterally out over the top wall 552 of the support member 548 and down over the upper corner 558 such that the fastening component 84 of the front side panel (and hence the engagement seam 88) is in opposed relationship with the diffuser plate 588 of the angled outer side wall 556. The back side panel 134 is expanded to extend below the bottom wall 560 of the support member 548 in spaced relationship with the front side panel 34, and up over the lower corner 562 of the support member. Expanding the side panels 34, 134 relative to the absorbent chassis in this manner substantially straightens, or pulls the side panels taut at the engagement seam 88 and positions the engagement seam in generally opposed relationship with the diffuser plate 588. More particularly, tensioning the side panels 34, 134 around the support member 548 urges the side panels 34, 134 to lay generally flat on the diffuser plate 588 at the engagement seam 88. Pressurized fluid exhausted from the air bar 570 is directed to impact at least one of the side panels 34, 134 at the engagement seam 88 to urge the engagement seam in toward the diffuser plate 588 to further urge the fastening components 82, 84 together.

Tensioning the side panels 34, 134 also pulls the engaged fastening components 82, 84 in opposite directions, e.g., by applying a pulling force to the fastening component of the front side panel 34 generally up along the side wall 556 and applying an opposite pulling force to the fastening component of the back side panel 134 generally down along the side wall as indicated by the directional arrows in FIG. 21. As a result, one of the fastening components 82, 84 is urged to slide relative to the other fastening component, and more particularly in the illustrated embodiment the fastening components are urged to slide relative to each other. The tensioning thus generates a shear stress at the engagement seam 88 to promote increased engagement between the fastening components 82, 84. For example, where the fastening components 82, 84 are hook and loop fasteners, generating a shear stress at the engagement seam 88 urges sliding movement of one fastening component relative to the other such that the hooks become further embedded or otherwise entangled in the loops, thereby strengthening the engagement between the fastening components. Where the base material of the loop fastener is constructed of an elastic material, the applied shear stress may alternatively, or may additionally, result in stretching (which is also broadly considered herein as a sliding movement) of the loop fastener relative to the hook fastener, thereby increasing the spacing between the loops to allow the hooks to embed deeper therein.

With the front and back side panels 34, 134 expanded out over the main portion 566 of the support member 548 so that the engagement seam 88 lays generally flat on the diffuser plate 588, the inspection control system operates the radiation source 582 to emit radiation. Radiation from the radiation source 582 diffuses through the diffuser plate 588 toward the engagement seam 88 to irradiate the side panels 34, 134 at the engagement seam from within the interior space 51 of the pants 102. The inspection control system also operates the image capturing device 594 to detect radiation transmitted outward through the engagement seam 88 to thereby capture an image of the engagement seam. The image is then processed and analyzed by a suitable image analyzer (not shown). For example, one desired image analyzer and method for analyzing the captured image is described in co-assigned U.S. application filed by Tomsovic et al. and entitled "Infrared Detection of Composite Article Components."

While the side panels 34, 134 of the illustrated embodiment are pulled taut around the support member 548 to subject the engagement seam 88 to a shear stress during inspection of the engagement seam, it is understood that the side panels need not be taut and that engagement seam may not be subjected to a shear stress during inspection of the engagement seam, as long as the fastening components 82, 84 at the engagement seam lay generally flat on the radiation source 582, and more particularly on the diffuser plate 588. For example, the fastening components 82, 84 at the engagement seam 88 may be urged to lay flat on the diffuser plate 588 (and hence, more broadly, the radiation source 582) by pressurized fluid from the air bar 570 or in another suitable manner without subjecting the engagement seam to a shear stress.

Figure 25:
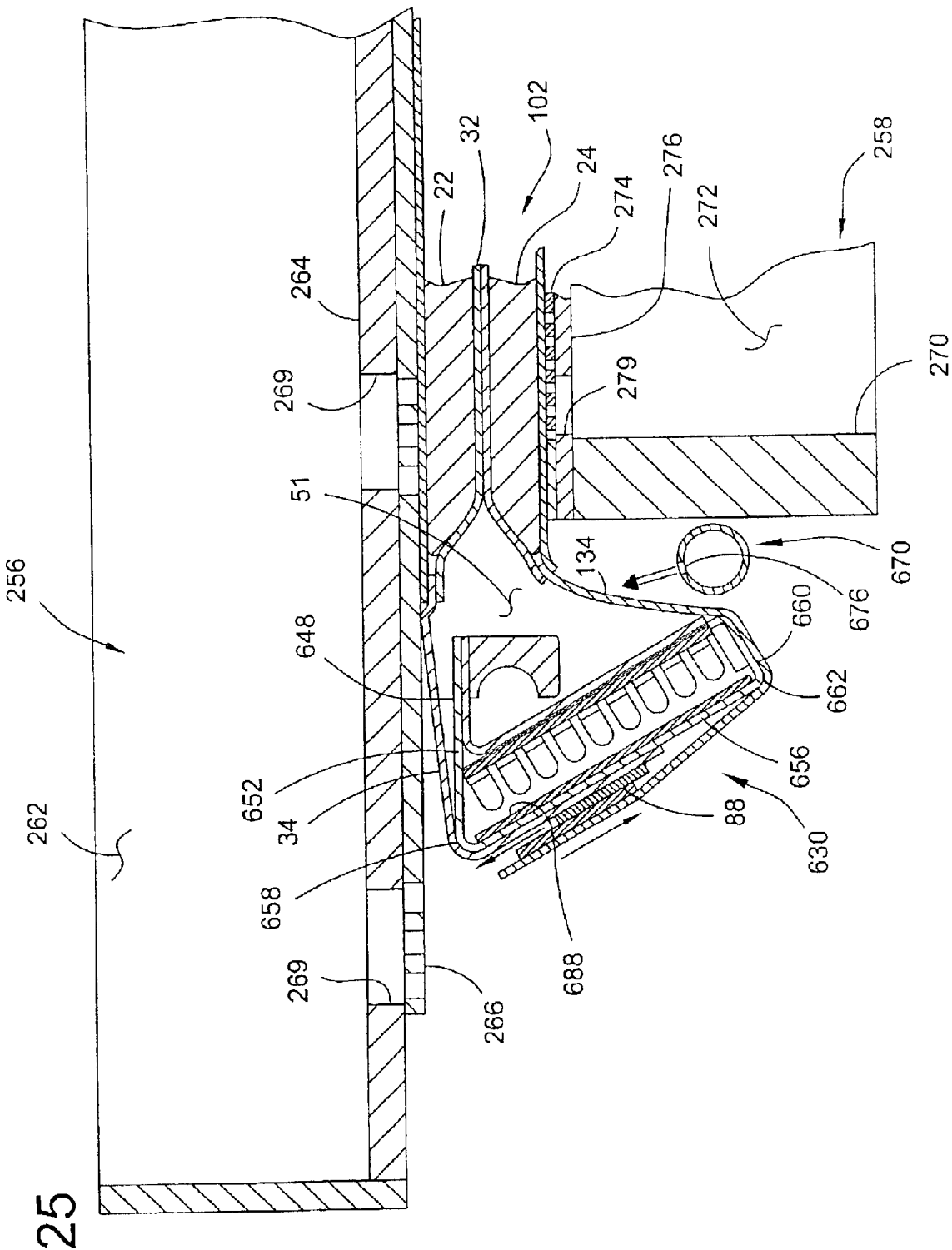
FIG. 25 is a partial section of a second embodiment of a seaming section of apparatus for making articles such as training pants, the section being taken at a location corresponding to the section shown in FIG. 21.

FIG. 25 is a cross-section of a second embodiment of a seaming section of apparatus of the present invention. The seaming section of this second embodiment is similar to that of the first embodiment except that the support assembly 630 further comprises an air bar, generally indicated at 670, positioned below and laterally inward of the bottom wall 660 of the support member 648. Exhaust openings 676 (one of which is shown in FIG. 25) of the air bar 670 are positioned so as to direct pressurized fluid, such as air, exhausted therefrom to impact the portion of the back side panel 134 extending between the back waist region 24 of the absorbent chassis 32 and the bottom wall 660 of the support member 648. The pressurized fluid urges the back side panel 134 to become taut around the bottom wall 660 and lower corner 662 of the support member 648. As a result, the front side panel 34 is pulled taut against the top wall 652 and upper corner 658 of the support member 648 to thereby urge the engagement seam 88 in toward the diffuser plate 688 to lay flat on the plate and to generate a shear stress at the engagement seam 88. It is contemplated that the fluid pressure of fluid exhausted from the air bar 670 may be selectively adjusted to control the tension in the side panels 34, 134.

While the support member 548, 648 of the illustrated embodiment has a cross-section generally in the shape of the numeral "7" so that the engagement seam 88 lays against a flat surface (e.g., the outer side wall 556, 656) upon tensioning of the front and back side panels 34, 134, it is contemplated that the support member may have a cross-section of generally any shape, such as circular (e.g., such as by using a roller), semi-circular, polygonal, U-shaped, C-shaped or any other suitable shape. The support member 548, 648 may also be oriented vertically (e.g., normal to the machine direction) instead of longitudinally. Also, the side panels 34, 134 need not lie on the support member 548, 648, diffuser plate 588, 688 or other flat surface upon tensioning of the front and back side panels 34, 134 at the engagement seam, but may instead remain free from contact with any structure without departing from the scope of this invention as long as the engagement seam is exposed to radiation emitted within the interior space 51 of the pants 102.

Moreover, the length of the support member 548, 648 over which the engagement seam 88 is conveyed may be substantially shorter than the length of the engagement seam so that only a portion of the engagement seam is conveyed over the support member at any given time. In this manner, the fastening components 82, 84 would tend to bend, or flex at the engagement seam 88 as the fastening components are conveyed over the support member 548, 648 to further work the fastening components together. It is also understood that the shear stress applied to the engagement seam 88 may alternatively, or may additionally, be generated in the machine direction (e.g., longitudinally) in which the training pants are transported through the seaming section, such as by applying a longitudinally oriented force (e.g., pulling, friction, etc.) to one of the fastening components 82, 84, or by applying longitudinally opposite forces to the fastening components.

Figure 26:
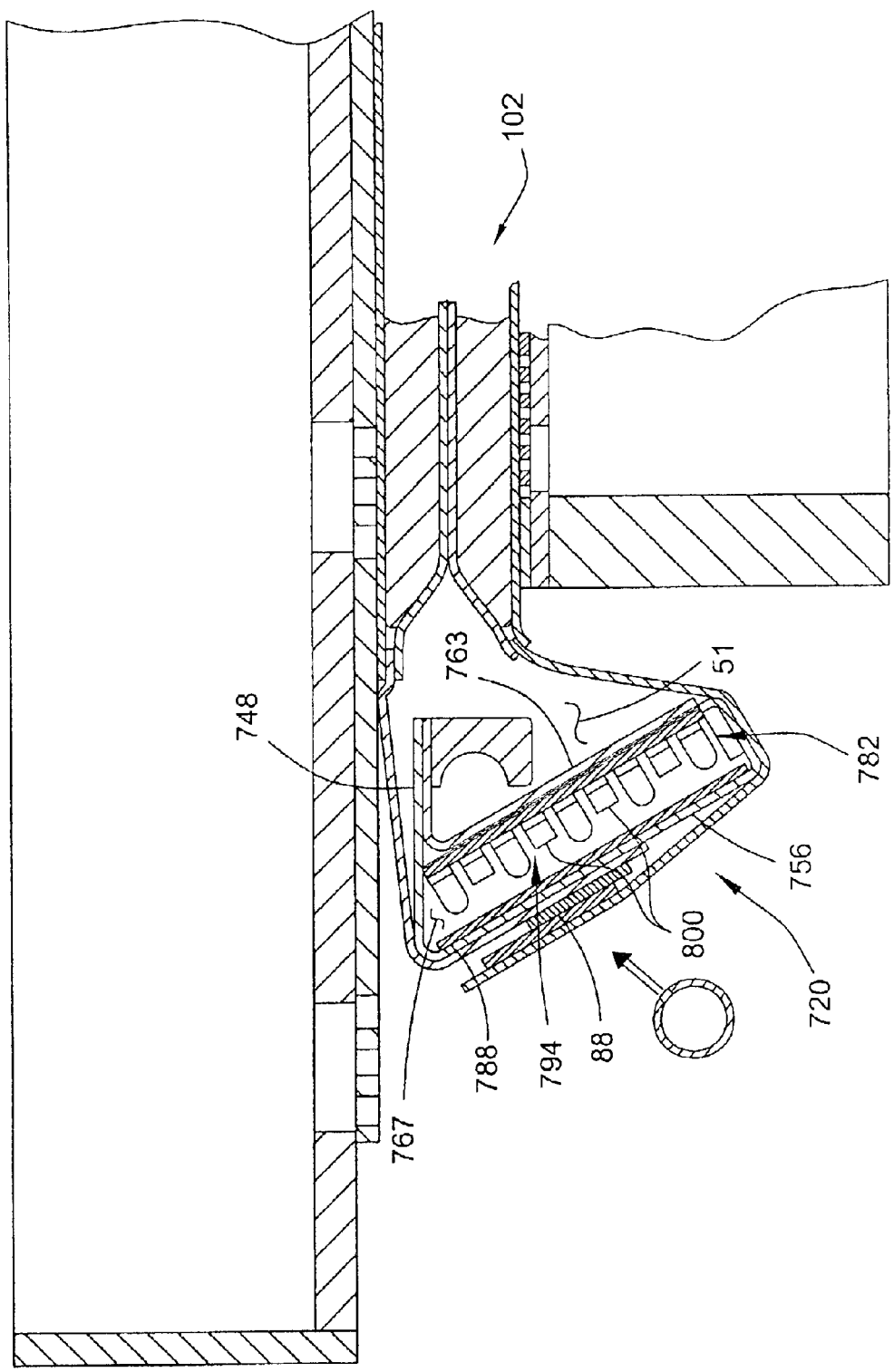
FIG. 26 is a partial section of a second embodiment of an inspection system of apparatus for making articles such as training pants, the section being taken at a location corresponding to the section shown in FIG. 21.

FIG. 26 illustrates a cross-section of an alternative embodiment of an inspection system 720 for inspecting the engagement seam 88 of the pants 102. The inspection system 720 is substantially similar to that of the first embodiment except that the image capturing device 794 is supported by the support member 748 for positioning within the interior space 51 of the pants 102 upon conveyance of the pants over the support member. More particularly, the device 794 is disposed within the channel 767 between the outer side wall 756 and inner side wall 763 of the support member 748 and aimed out toward the engagement seam 88. Instead of a diffuser plate (such as the diffuser plate 588 described previously), a transparent plate 788 is used to permit the image capturing device 794 to capture radiation reflected by the engagement seam back through the plate. As an example, a number of the LED's 584 of the radiation source 582 illustrated in FIG. 23 may replaced with one or more charged coupled devices 800 as shown in FIG. 26, or by linescan devices (not shown) or other suitable devices for detecting radiation. As another example, the image capturing device 794 may be a two-way image capturing device capable of emitting and detecting radiation.

In operation, the image capturing device 794 detects radiation emitted by the radiation source 782 and reflected by the engagement seam 88 to capture an image of the engagement seam. Positioning the image capturing device 794 within the interior space 51 of the pants 102 in this manner as the pants are conveyed over the support member 748 allows the device to capture a clearer image of the front side panel 34 (e.g., the underlying panel) at the engagement seam 88 since the device does not have to "look" through the back side panel 134 (e.g., the overlapping panel).

Figure 27:
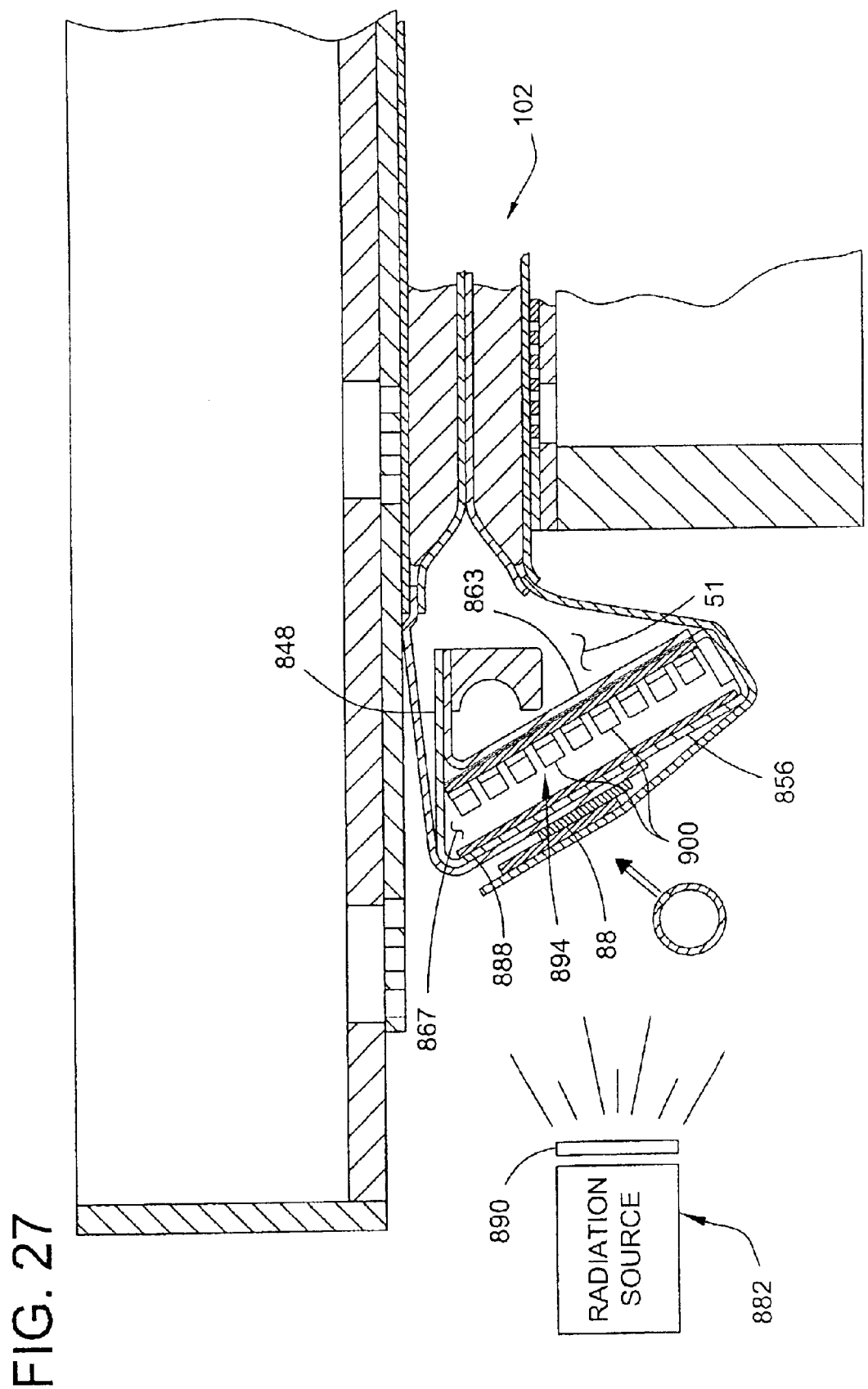
FIG. 27 is a partial section of a third embodiment of an inspection system of apparatus for making articles such as training pants, the section being taken at a location corresponding to the section shown in FIG. 21.

In another alternative embodiment, as shown in FIG. 27, a radiation source, indicated generally at 882, is positioned exterior of the support member 848 in spaced relationship with the outer side wall 856 of the support member and emits radiation in toward the engagement seam 88. A diffuser 890 is positioned between the radiation source 882 and the support member 848. The image capturing device 894 is positioned within the channel 867 between the outer side wall 856 and inner side wall 863 of the support member 848 and aimed out toward the engagement seam 88. Thus, radiation emitted by the radiation source 882 transmits through the diffuser 890 to the engagement seam 88, and then inward through the engagement seam and transparent plate 888 for detection by the image capturing device 894. The image capturing device 894 of the illustrated embodiment may comprise an array of charged coupled devices 900 as shown in FIG. 27, or by linescan devices (not shown) or other suitable devices for detecting radiation.

While expansion of the training pants 102 of the illustrated embodiment to facilitate inspection of the engagement seam 88 by the inspection system 520, 720 entails expanding the front and back side panels 34, 134 outward relative to the absorbent chassis 32, it is understood that the pants may be expanded in other suitable manners to straighten or otherwise pull the side panels taut at the engagement seam without departing from the scope of this invention. For example, while not shown in the drawings, the spacing between the upper and lower alignment conveyers 256, 258 may substantially increase toward the downstream end of the seaming section 250 following connection of the front and back side panels 34, 134 at the engagement seam 88 to expand the entire article at the absorbent chassis 32, e.g., by pulling the front and back waist regions 22, 24 of the absorbent chassis apart from each other. Increasing the spacing between the front and back waist regions 22, 24 causes the connected side panels 34, 134 to generally straighten therebetween to the pull the side panels taut at the engagement seam 88. As a result, the side panels 34, 134 do not need to be supported by the support member 548, 748 during inspection of the engagement seam 88.

Also, the methods and apparatus of the present invention are shown and described herein in connection with making a pair of child's training pants 20 and inspecting an engagement seam 88 thereof. However, it is understood that the methods and apparatus can be used to make and inspect a variety of articles other than pants 20 where such articles comprise at least two flexible elements connected together during the making of such articles in overlapping relationship with other to define an engagement seam as long as the article has an interior space bounded in part by the engagement seam. Such articles may include other disposable garments such as diapers, feminine hygiene products, incontinence products, other personal care or health care garments, swim pants, athletic clothing, pants and shorts, as well as other articles, such as balloons, tents, sleeves, cigarette packages, bags, and the like, whether such articles are disposable or not and whether such articles are absorbent or not.

It also contemplated that a shear stress may alternatively, or may additionally, be generated at the engagement seam 88 other than by the seaming section 250. For example, from the seaming section 250, the pre-fastened training pants 20 can be processed through various finishing stations 254 (FIG. 6) for operations such as side panel tucking, packaging, and the like, during which a shear stress may be applied to the engagement seam 88. FIG. 28 schematically illustrates a side panel tucking station, generally indicated at 730, downstream of the upper and lower alignment conveyors 256, 258 of the seaming section 250. The tucking station 730 comprises opposed upper and lower vacuum conveyors 732, 734 having an upstream end 736 generally aligned with the upper and lower alignment conveyors 256, 258 of the seaming section 250 for receiving the pre-fastened training pants 20 into the tucking station.

In the illustrated embodiment, the upper and lower vacuum conveyors 732, 734 are generally angled relative to the upper and lower alignment conveyors 256, 268 of the seaming section 250 for conveying the side panels from a downstream end 738 of the tucking station to subsequent processing apparatus (not shown). The vacuum conveyors 732, 734 are also angled relative to each other such that the spacing between the upper and lower vacuum conveyors at the upstream end 736 of the tucking station 730 is substantially greater than the spacing therebetween at the downstream end 738 of the tucking station.

A blade assembly, generally indicated at 740, is mounted on the upper vacuum conveyor 732 intermediate the upstream and downstream ends 736, 738 of the tucking station 730. The blade assembly comprises a pair of drive shafts 742 (one of which is shown in FIG. 28) spaced laterally outward from opposite sides of the upper and lower vacuum conveyors 732, 734. The drive shafts 742 are operatively connected to a suitable motor (not shown) for driven rotation about respective axes extending generally normal to the lower vacuum conveyor 732. Three blades 744 (two of which are shown in FIG. 28) are secured to each drive shaft 742 and extend outward from the drive shaft transverse to the rotation axis thereof for conjoint rotation with the drive shaft relative to the upper and lower vacuum conveyors 732, 734. As shown in FIG. 29, the blades 744 are positioned and sized to extend transversely between the upper and lower vacuum conveyors 732, 734 for contacting the connected front and back side panels 34, 134 of the training pants 20 upon rotation of the blades, and are more desirably positioned and sized in length such that upon rotation between the upper and lower vacuum conveyors, each blade is capable of extending substantially laterally inward of the side edges 36 of the absorbent chassis 32 of the training pants 20.

In operation, the pre-fastened training pants 20 are received between the upper and lower vacuum conveyors 732, 734 at the upstream end 736 of the tucking station 730. The front waist region 22 of the absorbent chassis 32 is drawn and held against the upper vacuum conveyor 732 and the back waist region 24 is drawn and held against the lower vacuum conveyor 734. The spacing between the conveyors 732, 734 at the upstream end 736 of the tucking station 730 pulls the front and back waist regions 22, 24 apart, thereby generally straightening the engaged front and back side panels 34, 134 (e.g., orienting the side panels more vertically) for exposure to the blades 744. As the training pants 20 are conveyed past the blade assembly 740 as shown in FIG. 28, the blades 744 rotate on the rotation axis of the drive shafts 742 into contact with the side panels (e.g., the back side panels 134 in the illustrated embodiment) to urge the engaged side panels 34, 134 laterally inward between the front and back waist regions 22, 24 of the training pants 20 to a tucked configuration.

The positioning and length of the blades 744 is such that the front and back side panels 34, 134 are pulled taut as shown in FIG. 28 upon being tucked between the front and back waist regions 22, 24 of the training pants 20. As a result, oppositely directed pulling forces, as indicated by direction arrows, are applied to the fastening components 82, 84 to generate shear stresses at the engagement seams 88. It is contemplated that the blades 744 on each side of tucking station 730 may instead contact the front side panels 34, or the blades on one side of the tucking station may contact the respective back side panel 134 and the blades on the opposite side of the tucking station may contact the respective front side panel 134, without departing from the scope of this invention.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method for making a pre-fastened article having at least two generally flexible elements capable of connection with each other during initial assembly of the article to at least partially form said pre-fastened article, the method comprising;

arranging a portion of one of the generally flexible elements in overlapping relationship with a portion of the other one of said elements;

connecting said element portions together to define an engagement seam of said article;

arranging the article to define an interior space thereof whereby the interior space is bounded in part by the engagement seam;

irradiating said elements at the engagement seam from within the interior space of the article; and capturing an image of the irradiated engagement seam.

2. A method as set forth in claim 1 wherein the step of irradiating comprises positioning a source of radiation within the interior space of the article and operating said radiation source to emit radiation toward the engagement seam.

3. A method as set forth in claim 2 wherein the radiation is infrared radiation.

4. A method as set forth in claim 3 wherein the radiation has a wavelength in the range of about 700 nanometers to about 1,200 nanometers.

5. A method as set forth in claim 2 further comprising diffusing the radiation emitted from the radiation source toward the engagement seam.

6. A method as set forth in claim 2 further comprising the step of conveying the article in a predetermined direction over the radiation source such that the radiation source is positioned within the interior space of the article upon conveyance of the article over said radiation source.

7. A method as set forth in claim 2 further comprising supporting the generally flexible elements on a support member disposed generally within the interior space of the article such that the support member is positioned generally between the radiation source and the engagement seam, said support member being at least partially constructed of a material which permits the transmission of radiation therethrough whereby radiation emitted by the radiation source generally within the interior space of the article passes through the support member toward the engagement seam.

8. A method as set forth in claim 7 further comprising urging the generally flexible elements to lay generally flat on the support member at the engagement seam while capturing an image of the engagement seam.

9. A method as set forth in claim 8 wherein the step of urging the elements comprises directing pressurized fluid toward the support member to impact at least one of the elements generally at the engagement seam whereby the pressurized fluid urges the elements to lay generally flat on the support member at the engagement seam.

10. A method as set forth in claim 8 further comprising mechanically handling the article to generally tension the elements over the support member whereby tensioning the elements urges the elements in toward the support member to facilitate laying the elements generally flat on the support member at the engagement seam.

11. A method as set forth in claim 10 wherein tensioning of the elements generates a shear stress at the engagement seam.

12. A method as set forth in claim 1 wherein the step of capturing an image of the engagement seam comprises detecting radiation transmitted generally through the elements at the engagement seam to capture an image thereof.

13. A method as set forth in claim 12 wherein the step of capturing an image of the engagement seam further comprises positioning an image capturing device exterior of the article and operating said device to detect radiation transmitted from generally within the interior space of the article out through the elements at the engagement seam.

14. A method as set forth in claim 1 wherein the step of capturing an image of the engagement seam comprises detecting radiation which is generally reflected by the engagement seam to capture an image thereof.

15. A method as set forth in claim 14 wherein the step of capturing an image of the engagement seam further comprises positioning an image capturing device generally within the interior space of the article and operating said device to detect radiation generally reflected by the engagement seam.

16. A method as set forth in claim 1 further comprising mechanically handling the article to generate a shear stress at the engagement seam at least one of before and during the step of capturing the image of said engagement seam.

17. A method for making a pre-fastened article having at least two generally flexible elements capable of connection with each other during initial assembly of the article to at least partially form said pre-tastened article, the method comprising:
    arranging a portion of one ct the generally flexible elements in overlapping relationship with a portion of the other one of said elements;
    connecting said element portions together to define an engagement seam of said article;
    arranging the article to define an interior space thereof whereby the interior space is bounded in part by the engagement seam;
    irradiating the elements at the engagement seam; and
    capturing an image of the irradiated engagement seam from generally within the interior space of the article.

18. A method as set forth in claim 17 wherein the step of irradiating the elements at the engagement seam comprises emitting radiation generally within the interior space of the article toward the engagement seam.

19. A method as set forth in claim 17 wherein the elements are irradiated with infrared radiation.

20. A method as set forth in claim 19 wherein the radiation has a wavelength in the range of about 700 nanometers to about 1,200 nanometers.

21. A method as set forth in claim 17 wherein the step of capturing an image of the engagement seam comprises positioning an image capturing device generally within the interior space of the article with the device aimed generally toward the engagement seam and operating the image capturing device to capture an image of the irradiated engagement seam.

22. A method as set forth in claim 21 further comprising the step of conveying the article in a predetermined direction over the image capturing device such that the image capturing device is positioned within the interior space of the article, said steps of irradiating the elements at the engagement seam and operating the image capturing device being performed while the article is conveyed over the image capturing device.

23. A method as set forth in claim 17 further comprising supporting the generally flexible elements on a support member disposed generally within the interior space of the article whereby the support member is positioned generally between the image capturing device and the elements at the engagement seam, said support member being at least partially constructed of a material which permits the transmission of radiation therethrough.

24. A method as set forth in claim 23 further comprising urging the elements to lay generally flat on the support member at the engagement seam while capturing an image of the engagement seam.

25. A method as set forth in claim 24 wherein the step of urging the elements comprises directing pressurized fluid toward the support member to impact at least one of the elements generally at the engagement seam whereby the pressurized fluid urges the elements to lay generally flat on the support member at the engagement seam.

26. A method as set forth in claim 24 further comprising mechanically handling the article to generally tension the elements over the support member at the engagement seam whereby tensioning the elements urges the engagement seam in toward the support member to facilitate laying the engagement generally flat on the support member.

27. A method as set forth in claim 26 wherein tensioning the elements generates a shear stress at the engagement seam.

28. A method as set forth in claim 17 further comprising mechanically handling the article to generate a shear stress at the engagement seam at least one of before and during the step of capturing the image of said engagement seam.

29. A method as set forth in claim 17 wherein the step of irradiating the elements at the engagement seam comprises emitting radiation generally exterior of the article toward the engagement seam.

30. A method for inspecting an engagement seam of pre-fastened disposable pants comprising an absorbent chassis having a front waist region, a back waist region and a crotch region extending longitudinally therebetween, a front side panel extending laterally out from the front waist region, a back side panel extending laterally out from the back waist region, a portion of the front side panel being connected to a portion of the back side panel in overlapping relationship therewith to define an engagement seam, and an interior space bounded in part by the front and back side panels at the engagement seam, said method comprising the steps of:
    irradiating the front and back side panels at the engagement seam from generally within the interior space of the pants; and
    capturing an image of the irradiated engagement seam.

31. A method as set forth in claim 30 wherein the step of irradiating comprises positioning a source of radiation within the interior space of the pants and operating said radiation source to emit radiation within said interior space toward the engagement seam.

32. A method as set forth in claim 31 wherein the radiation is infrared radiation.

33. A method as set forth in claim 32 wherein the radiation has a wavelength in the range of about 700 nanometers to about 1,200 nanometers.

34. A method as set forth in claim 31 further comprising diffusing the radiation within the interior space of the pants as said radiation radiates toward the engagement seam.

35. A method as set forth in claim 31 further comprising the step of conveying the pants in a predetermined direction over the radiation source such that the radiation source is positioned within the interior space of the pants.

36. A method as set forth in claim 31 further comprising supporting the front and back side panels on a support member disposed generally within the interior space of the pants whereby the support member is positioned generally between the radiation source and the engagement seam, said support member being at least partially constructed of a material which permits the transmission of radiation therethrough such radiation emitted by the radiation source generally within the interior space of the pants passes through the support member toward the engagement seam.

37. A method as set forth in claim 36 further comprising urging the engagement seam to lay generally flat on the support member while capturing an image of the engagement seam.

38. A method as set forth in claim 37 wherein said urging step comprises directing pressurized fluid to impact at least one of the panels generally at the engagement seam whereby the pressurized fluid urges the engagement seam to lay generally flat on the support member.

39. A method as set forth in claim 37 further comprising mechanically handling the pants to generally tension the panels over the support member whereby tensioning of the panels urges tho engagement seam in toward the support member to facilitate laying the engagement generally flat on the support member.

40. A method as set forth in claim 39 wherein tensioning the panels generates a shear stress at the engagement seam.

41. A method as set forth in claim 30 wherein the step of capturing an image of the engagement seam comprises detecting radiation transmitted generally through the panels at the engagement seam to capture an image thereof.

42. A method as set forth in claim 41 wherein the step of capturing an image of the engagement seam further comprises positioning an image capturing device exterior of the pants and operating said device to detect radiation transmitted generally through the panels at the engagement seam.

43. A method as set forth in claim 30 wherein the step of capturing an image of the engagement seam comprises detecting radiation which is generally reflected by the engagement seam to capture an image thereof.

44. A method as set forth in claim 43 wherein the step of capturing an image of the engagement seam further comprises positioning an image capturing device generally within the interior space of the pants and operating said device to detect radiation generally reflected by the engagement seam.

45. A method as set forth in claim 30 further comprising generating a shear stress at the engagement seam at least one of before and during the step of capturing the image of said engagement seam.

46. A method as set forth in claim 30 further comprising expanding at least a portion of the pants to generally tension the front and back side panels at the engagement seam at least one of before and during the step of capturing the image of said engagement seam.

47. A method as set forth in claim 46 wherein the front and back side panels are expanded generally outward relative to the absorbent chassis to tension the side panels at the engagement seam.

48. A method as set forth in claim 47 further comprising gripping the absorbent chassis as the side panels are expanded outward relative to the absorbent chassis.

49. A method for inspecting an engagement seam of pre-fastened disposable pants comprising an absorbent chassis having a front waist region, a back waist region and a crotch region extending longitudinally therebetween, a front side panel extending laterally out from the front waist region, a back side panel extending laterally out from the back waist region, a portion of the front side panel being connected to a portion of the back side panel in overlapping relationship therewith to define an engagement seam, and an interior space bounded in part by the front and back side panels at the engagement seam, said method comprising the steps of:

irradiating the front and back side panels at the engagement seam; and capturing an image of the irradiated engagement seam from generally within the interior space of the pants.

50. A method as set forth in claim 49 wherein the step of irradiating the panels at the engagement seam comprises emitting radiation generally within the interior space of the article out toward the engagement seam.

51. A method as set forth in claim 49 wherein the panels are irradiated with infrared radiation.

52. A method as set forth in claim 51 wherein the radiation has a wavelength in the range of about 700 nanometers to about 1,200 nanometers.

53. A method as set forth in claim 49 further comprising the step of positioning an image capturing device generally within the interior space of the article and aiming the device generally out toward the engagement seam.

54. A method as set forth in claim 53 further comprising conveying the pants in a predetermined direction over the image capturing device such that the image capturing device is positioned within the interior space of the article, said steps of irradiating the panels at the engagement seam and operating the image capturing device being performed while the article is conveyed over the image capturing device.

55. A method as set forth in claim 54 further comprising arranging the article to have a generally closed cross-section transverse to said predetermined direction.

56. A method as set forth in claim 49 further comprising supporting the panels on a support member disposed generally within the interior space of the pants whereby the support member is positioned generally between the image capturing device and the engagement seam, said support member being at least partially constructed of a material which permits the transmission of radiation therethrough.

57. A method as set forth in claim 56 further comprising urging the engagement seam to lay generally flat on the support member while capturing an image of the engagement seam.

58. A method as set forth in claim 57 wherein the engagement seam is urged toward the support member by pressurized fluid directed to impact at least one of the panels generally at the engagement seam whereby the pressurized fluid urges the engagement seam to lay generally flat on the support member.

59. A method as set forth in claim 56 further comprising mechanically handling the article to generally tension the panels over the support member whereby tensioning of the panels urges the engagement seam in toward the support member to facilitate laying the engagement generally flat on the support member.

60. A method as set forth in claim 59 wherein tensioning the panels generates a shear stress at the engagement seam.

61. A method as let forth in claim 49 further comprising mechanically handling the article to generate a shear stress at the engagement seam at least one of before and during the step of capturing the image of said engagement seam.

62. A method as set forth in claim 49 wherein the steps of irradiating the panels at the engagement seam comprises emitting radiation generally exterior of the article toward the engagement seam.

63. A method for making pre-fastened disposable pants comprising an absorbent chassis having a front waist region, a back waist region and a crotch region extending longitudinally therebetween a front side panel extending laterally out from the front waist region, a back side panel extending laterally out from the back waist region, a portion of the front side panel being adapted for connection to a portion of the back side panel, said method comprising:

arranging the front and back side panels relative to each other such that the connectable portions of the front and back side panels are in at least partially opposed relationship with each other;

connecting said portions of the side panels together to define an engagement seam;

expanding at least a portion of the pants to tension the front and back side panels generally at the engagement seam; and inspecting the engagement seam while said portion of the pants is expanded.

64. A method as set forth in claim 63 further comprises assembling the pants in a generally unfolded, laid flat configuration to form the absorbent chassis and the front and back side panels extending respectively out from the front and back waist regions of the absorbent chassis, said assembling step being performed prior to said arranging step, said arranging step comprising folding the pants on a foldline extending laterally through the crotch region of the absorbent chassis such that the front waist region is in opposed relationship with the back waist region and the front side panel is in opposed relationship with the back side panel.

65. A method as set forth in claim 64 further comprising the step of tucking the front and back side panels at the engagement seam between the front and back waist regions of the absorbent chassis following inspection of the engagement seam.

66. A method as set forth in claim 65 further comprising tensioning the side panels as the side panels are tucked between the front and back waist regions whereby said tensioning generates a shear stress at the engagement seam.

67. A method as set forth in claim 64 wherein the arranging step further comprises overlapping the connectable portion of one of said side panels with the connectable portion of the other one of said side panels.

68. A method as set forth in claim 63 wherein the step of expanding at least a portion of the pants comprises pulling the front and back side panels in generally opposite directions to tension the side panels at the engagement seam.

69. A method as set forth in claim 68 wherein the step of expanding at least a portion of the pants comprises expanding the side panels generally outward relative to the absorbent chassis.

70. A method as set forth in claim 69 wherein the step of expanding the side panels comprises tensioning the side panels over a support member.

71. A method as set forth in claim 70 further comprising urging the engagement seam to lay generally flat on the support member while capturing an image of the engagement seam.

72. A method as set forth in claim 71 wherein the engagement seam is urged toward the support member by pressurized fluid directed to impact at least one of the side panels generally at the engagement seam whereby the pressurized fluid urges the engagement seam to lay generally flat on the support member.

73. A method as set forth in claim 63 further comprising mechanically handling the pants to generate a shear stress at the engagement seam at least one of before and during the step of capturing the image of said engagement seam.

74. A method as set forth in claim 63 wherein the pants are configured to have an interior space following connection of the front and back side panels at the engagement seam whereby the interior space is bounded in part by the engagement seam, said inspecting step comprising irradiating the front and back side panels at the engagement seam from within said interior space.

75. A method as set forth in claim 74 wherein the inspection step further comprises capturing an image of the engagement seam from within said interior space.

76. A method as set forth in claim 63 wherein the pants are configured to have an interior space following connection of the front and back side panels at the engagement seam whereby the interior space is bounded in part by the engagement seam, said inspecting step comprising capturing an image of the engagement seam from within said interior space.

77. A method as set forth in claim 63 further comprising conveying the pants in a predetermined direction while performing each of said arranging, connecting, expanding and image capturing steps.

78. Apparatus for making a pre-fastened article, said article comprising two generally flexible elements capable of connection with each other to assemble said article, said apparatus comprising:

a seaming section adapted to connect the elements in overlapping relationship with each other to define an engagement seam and to configure the article so as to define an interior space thereof whereby the interior space is bounded in part by the engagement seam; and an inspect ion system for inspecting the engagement seam, said inspection system comprising a source of radiation operable to emit radiation generally within the interior space of said article toward the engagement seam for irradiating said elements at the engagement seam, and an image capturing device adapted to capture an image of the irradiated engagement seam.

79. Apparatus as set forth in claim 78 wherein the radiation source emits infrared radiation.

80. Apparatus as set forth in claim 79 wherein the radiation source emits infrared radiation having a wavelength in the range of about 700 nanometers to about 1,200 nanometer.

81. Apparatus as set forth in claim 78 further comprising a diffuser plate for diffusing radiation emitted by the radiation source toward the engagement seam.

82. Apparatus as set forth in claim 78 wherein the image capturing device is positioned relative to the radiation source such that said device is disposed exterior of the article when the radiation source is disposed within the interior space of said article.

83. Apparatus as set forth in claim 78 wherein the image capturing device is positioned relative to the radiation source for detecting radiation generally reflected by the elements at the engagement seam upon irradiation of the engagement seam from within the interior space of the article.

84. Apparatus as set forth in claim 83 wherein the image capturing device is positioned relative to the radiation source such that said device and said radiation source are each disposed within the interior space of the article.

85. Apparatus as set forth in claim 78 wherein the inspection system further comprises a support member adapted for positioning generally within the interior space of the article to support the elements during operation of the image capturing device to capture an image of the engagement seam, said support member being at least partially constructed of a material which permits the transmission therethrough of radiation emitted by the radiation source.

86. Apparatus as set forth in claim 85 wherein the inspection system further comprises a fluid delivery device for directing pressurized fluid toward the support member to impact at least one of said elements generally at the engagement seam whereby said pressurized fluid urges the engagement seam to lay generally flat on the support member.

87. Apparatus as set forth in claim 85 wherein the support member is adapted to generally tension the elements at the engagement seam whereby said tensioning urges the engagement seam to lay generally flat on the support member.

88. Apparatus as set forth in claim 87 wherein said apparatus is adapted to convey the article therethrough in a predetermined direction over the support member, said support member being adapted to tension the elements at the engagement seam as the article is conveyed in the predetermined direction over the support member.

89. Apparatus as set forth in claim 88 wherein the support member is arranged and configured for expanding the article to thereby tension said elements at the engagement seam as the article is conveyed in the predetermined direction over the support member.

90. Apparatus for making a pre-fastened article, said article comprising two generally flexible elements capable of connection with each other to assemble said article, said apparatus comprising:
   a seaming section adapted to correct the flexible elements in overlapping relationship with each other to define an engagement seam and to configure the article so as to define an interior space thereof whereby the interior space is bounded in part by the engagement seam; and
   an inspection system for inspecting the engagement seam, said inspection system comprising a source of radiation adapted to irradiate the engagement seam, and an image capturing device operable to capture an image of the irradiated engagement seam generally from within the interior space of the article.

91. Apparatus as set forth in claim 90 wherein the image capturing device is operable to detect infrared radiation.

92. Apparatus as set forth in claim 91 wherein the image capturing device is operable to detect infrared radiation having a wavelength in the range of about 700 nanometers to about 1,200 nanometers.

93. Apparatus as set forth in claim 90 wherein the image capturing device is operable to detect at least one of radiation transmitted through the elements at the engagement seam and radiation reflected by the engagement seam.

94. Apparatus as set forth in claim 90 wherein the inspection system further comprises a support member adapted for positioning generally within the interior space of the article to support the elements during operation of the image capturing device to capture an image of the engagement seam, said support member being at least partially constructed of a material which permits the transmission therethrough of radiation emitted by the radiation source.

95. Apparatus as set forth in claim 94 wherein the inspection system further comprises a fluid delivery device for directing pressurized fluid toward the support member to impact at least one of said elements generally at the engagement seam whereby said pressurized fluid urges the engagement seam to lay generally flat on the support member.

96. Apparatus as set forth in claim 94 wherein the support member is adapted to generally tension the elements at the engagement seam whereby said tensioning urges the engagement seam to lay generally flat on the support member.

97. Apparatus as set forth in claim 96 wherein said apparatus is adapted to convey the article therethrough in a predetermined direction over the support member, said support member being adapted to tension the elements at the engagement seam as the article is conveyed in the predetermined direction over the support member.

98. Apparatus as set forth in claim 97 wherein the support member is arranged and configured for expanding the article to thereby tension said elements at the engagement seam as the article is conveyed in the predetermined direction over the support member.

99. Apparatus as set forth in claim 94 wherein the image capturing device is supported by the support member.

100. Apparatus for making pre-fastened disposable pants comprising an absorbent chassis having a front waist region, a back waist region and a crotch region extending longitudinally therebetween, a front side panel extending laterally out from the front waist region, a back side panel extending laterally out from the back waist region, a portion of the front side panel being adapted for connection with a corresponding portion of the back side panel whereby the pre-fastened pants are at least partially formed by connecting said panel portions together, the apparatus being adapted for conveying the article in a machine direction therethrough, said apparatus comprising:
   a seaming section adapted to connect the side panels in overlapping relationship with each other upon movement of the pants in the machine direction to define an engagement seam and to configure the pants so as to define an interior space thereof whereby the interior space is bounded in part by the engagement seam; and
   an inspection system for inspecting the engagement seam, said inspection system comprising a source of radiation operable to emit radiation generally within the interior space of said pants toward the engagement seam for irradiating said engagement seam, a support member and an image capturing device adapted to capture an image of the irradiated engagement seam.

101. Apparatus as set forth in claim 100 wherein the inspection system further comprises a support member adapted for interposition between the front and back side panels within the interior space of the pants upon conveyance of the pants in the machine direction to support said panels during inspection of the engagement seam.

102. Apparatus as set forth in claim 101 wherein the inspection system further comprises a fluid delivery device adapted to direct pressurized fluid toward a portion of the support member to impact at least one of said side panels at the engagement seam to urge the engagement seam to lay generally flat against said portion of the support member.

103. Apparatus as set forth in claim 101 wherein the support member is adapted to tension the front and basic side panels whereby said tensioning of the side panels generally urges the engagement seam to lay flat on said support member.

104. Apparatus as set forth in claim 101 wherein the image capturing device is supported by the support member.

105. Apparatus as set forth in claim 104 wherein the support member comprises an outer side wall and an inner side wall in generally parallel, spaced relationship with the outer side wall to define a channel therebetween, the image capturing device being disposed within said channel.

106. Apparatus as set forth in claim 105 wherein the radiation source is disposed within said channel.

107. Apparatus as set forth in claim 100 wherein the image capturing device is operable to detect infrared radiation.

108. Apparatus as set forth in claim 107 wherein the image capturing device is operable to detect infrared radiation having a wavelength in the range of about 700 nanometers to about 1,200 nanotmeters.

109. Apparatus as set forth in claim 100 further comprising an assembly section adapted to at least partially assemble the pants such that the pants exit the assembly section in a generally unfolded configuration with the front and back side panels disconnected from each other, the assembly section being disposed from the seaming section in the machine direction of said apparatus.

110. Apparatus as set forth in claim 109 further comprising a folding section intermediate the assembly section and the seaming section, the folding suction being operable to fold the pants along a fold line extending generally laterally through the crotch region of the absorbent chassis such that the front waist region of the absorbent chassis is in opposed relationship with the back waist region thereof and the front side panel is in opposed relationship with the back side panel prior to the pants being conveyed downstream to the seaming section.

111. Apparatus as set forth in claim 110 further comprising a tucking station disposed downstream of the seaming section and adapted to tuck the front and back side panels generally between the opposed front and back waist regions of the absorbent chassis.

112. Apparatus for making pre-fastened disposable pants comprising an absorbent chassis having a front waist region, a back waist region and a crotch region extending longitudinally therebetween, a front side panel extending laterally out from the front waist region, a back side panel extending laterally out from the back waist region, a portion of the front side panel being adapted for connection with a corresponding portion of the back side panel whereby the pre-fastened pants are at least partially formed by connecting said panel portions together, the pre-fastened pants being conveyed in a machine direction through the apparatus, said apparatus comprising:

a seaming section adapted to connect the side panels in overlapping relationship with each ocher upon movement of the pants in the machine direction to define an engagement seam and to configure the pants so as to define an interior space thereof whereby the interior space is bounded in part by the engagement seam; and an inspection system for inspecting the engagement seam, the inspection system comprising a support member for supporting the side panels at the engagement seam generally within the interior of the pants, a source of radiation operable to irradiate said side panels at the engagement seam and an image capturing device operable to capture an image of the irradiated engagement seam.

113. Apparatus as set forth in claim 112 wherein the inspection system is adapted to tension the side panels at the engagement seam to facilitate inspection thereof.

114. Apparatus as set forth in claim 113 wherein the support member is configured and arranged to tension the side panels at the engagement seam.

115. Apparatus as set forth in claim 113 wherein the inspection system further comprises a fluid delivery device adapted to direct pressurized fluid toward the support member to impact at least one of said side panels at the engagement seam to urge the engagement seam to lay generally flat against said portion of the support member.

116. Apparatus as set forth in claim 112 further comprising an assembly section adapted to at least partially assemble the pants such that the pants exit the assembly section in a generally unfolded configuration with the front and back side panels disconnected from each other, the assembly section being disposed upstream from the seaming section in the machine direction of said apparatus.

117. Apparatus as set forth in claim 116 further comprising a folding section intermediate the assembly section and the seaming section, the folding section being operable to fold the pants along a fold line extending generally laterally through the crotch region of the absorbent chassis such that the front waist region of the absorbent chassis is in opposed relationship with the back waist region thereof and the front side panel is in opposed relationship with the back side panel prior to the pants being conveyed downstream to the seaming section.

118. Apparatus as set forth in claim 117 further comprising a tucking station disposed downstream of the seaming section and adapted to tuck the front and back side panels generally between the opposed front and back waist regions of the absorbent chassis.

119. An inspection system for inspecting an engagement seam of pre-fastened pants, said pants being of the type comprising an absorbent chassis having a front waist regions a back waist region and a crotch region extending longitudinally therebetween, a front side panel extending laterally out from the front waist region, a back side panel extending laterally out from the back waist region, a portion of the front side panel being adapted for connection with a corresponding portion of the back side panel to define an engagement seam whereby the pre-fastened pants are at least partially formed by connecting said panel portions together, said inspection system comprising:

a support member adapted for configuring the pants to define an interior space thereof bounded in part by the front and back side panels at the engagement seam, the support member being further configured to generally expand the pants to tension the side panels at the engagement seam, a source of radiation for irradiating the side panels at the engagement seam, and an image capturing device for capturing an image of the irradiated engagement seam.

120. An inspection system as set forth in claim 119 wherein the support member is positionable within the interior space of the pants to support the side panels at the engagement seam upon tensioning thereof, said support member having a generally flat surface oriented for opposed relationship with the engagement seam upon tensioning of the front side back side panels.

121. An inspection system as set forth in claim 120 wherein the support member is elongate and is oriented to extend generally parallel to the engagement seam.

122. An inspection system as set forth in claim 120 wherein the support member is supported by said apparatus and is oriented such that the side panels lay generally flat on the flat surface of the support member at the engagement seam upon tensioning of said side panels.

123. An inspection system as set forth in claim 120 wherein the support member comprises a first wall and a second wall connected to said first wall and defining said flat surface.

124. An inspection system as set forth in claim 123 wherein the second wall is angled relative to said first wall.

125. An inspection system as set forth in claim 124 wherein the second wall is angled relative to said first wall at an angle of about 50 degrees to about 65 degrees.

126. An inspection system as set forth in claim 124 wherein the support member has a cross-sectional shape generally resembling the numeral seven.

127. Apparatus as set forth in claim 120 wherein the inspection system further comprises a fluid delivery device adapted to direct pressurized fluid toward the support member to impact at least one of said side panels at the engagement seam to urge the engagement seam to lay generally flat against said flat surface of the support member.

128. Apparatus as set forth in claim 120 wherein the support member is adapted to tension the front and back side panels at the engagement seam whereby said tensioning of the side panels generally urges the engagement seam to lay flat on said flat surface of the support member.

129. Apparatus as set forth in claim 120 wherein at least one of the radiation source and the image capturing device is supported by the support member.

130. Apparatus as set forth in claim 120 wherein the support member comprises an outer side wall and an inner side wall in generally parallel, spaced relationship with the outer side wall to define a channel therebetween, at least one of the radiation source and the image capturing device being disposed within said channel.

131. A method for making a pre-fastened article having at least two generally flexible elements capable of connection with each other during initial assembly of the article to at least partially form said pre-fastened article, the method comprising:
    arranging a portion of one of the generally flexible elements in overlapping relationship with a portion of the other one of said elements;
    connecting said element portions together to define an engagement seam of said article;
    arranging the article to define an interior space thereof whereby the interior space is bounded in part by the engagement seam;
    urging said elements at the engagement seam to lay generally flat on a source of radiation;
    emitting radiation from said radiation source toward the engagement seam to irradiate said elements at the engagement seam; and
    capturing an image of the irradiated engagement seam.

132. A method as set forth in claim 131 wherein the radiation is infrared radiation.

133. A method as set forth in claim 131 further comprising diffusing radiation emitted from the radiation source toward the engagement seam.

134. A method as set forth in claim 131 wherein the step of urging the elements comprises directing pressurized fluid to impact at least one of the elements generally at the engagement seam whereby the pressurized fluid urges the elements to lay generally flat on the radiation source at the engagement seam.

135. A method as set forth in claim 131 wherein the radiation source emits radiation from within the interior space of the article.

136. Apparatus for making a pre-fastened article, said article comprising two generally flexible element, capable of connection with each other to assemble said article, said apparatus comprising:
    a seaming section adapted to connect the elements in overlapping relationship with each other to define an engagement seam and to configure the article so as to define an interior space thereof whereby the interior space is bounded in part by the engagement seam; and
    an inspection system for inspecting the engagement seam, said inspection system comprising a source of radiation operable to emit radiation toward the engagement seam for irradiating said elements at the engagement seam, a fluid delivery device for directing pressurized fluid to impact at least one of said elements generally at the engagement seam whereby said pressurized fluid urges the engagement seam to lay generally flat over the radiation source, and an image capturing device adapted to capture an image of the irradiated engagement seam.

137. Apparatus as set forth in claim 136 wherein the radiation source emits infrared radiation.

138. Apparatus as set forth in claim 136 further comprising a diffuser plate for diffusing radiation emitted by the radiation source toward the engagement seam, the fluid delivery device urging said engagement seam to lay generally flat on the diffuser plate.

139. Apparatus as set forth in claim 136 wherein the radiation source is operable to emit radiation generally within the interior space of said article.

140. A method for making pre-fastened disposable pants comprising an absorbent chassis having a front waist region, a back waist region and a crotch region extending longitudinally therebetween, a front side panel extending laterally cut from the front waist region, a back side panel extending laterally out from the back waist region, a portion of the front side panel being adapted for connection with a corresponding portion of the back side panel whereby the pre-fastened pants are at least partially formed by connecting said panel portions together, said method comprising:
    assembling the pants in a generally unfolded configuration with the front and back side panels disconnected from each other;
    folding the pants on a foldline extending laterally through the crotch region of the absorbent chassis such that the front waist region is in at least partially opposed relationship with the back waist region and the front side panel is in at least partially opposed relationship with the back side panel;
    connecting said portions of the side panels together to define an engagement seam,
    inspecting the engagement seam; and
    tucking at least a portion of the front and back side panels at the engagement seam between the at least partially opposed front and back waist regions of the absorbent chassis.

141. A method as set forth in claim 140 wherein the pants are configured to have an interior space following connection of the front and back side panels at the engagement seam whereby the interior space is bounded in part by the engagement seam, said inspecting step comprising irradiating the front and back side panels at the engagement seam from within said interior space and capturing an image of the irradiated engagement seam.

142. A method as set forth in claim 140 further comprising tensioning the front and back side panels generally at the engagement seam.

143. A method as set forth in claim 142 wherein said tensioning step is performed generally concurrently with the inspecting step.

* * * * *

UNITED STATES PATENT AND TRADEMARK OFFICE
CERTIFICATE OF CORRECTION

PATENT NO. : 6,888,143 B2
DATED : May 3, 2005
INVENTOR(S) : Vogt et al.

It is certified that error appears in the above-identified patent and that said Letters Patent is hereby corrected as shown below:

Column 3,
Line 53, "the generally" should read -- the article generally --.

Column 5,
Line 6, should not be a new paragraph.

Column 11,
Line 40, "N.J." should read -- N.J., --.

Column 12,
Line 9, "Minn." should read -- Minn., --.

Column 13,
Line 10, "Pa." should read -- Pa., U.S.A. --.
Line 20, "bonded carded" should read -- bonded-carded --.

Column 17,
Line 24, "Minn." should read -- Minn., --.

Column 18,
Line 65, "134" should read -- 34 --.

Column 19,
Line 15, "100" should read -- 100 --.

Column 29,
Line 20, "Del." should read -- Del., --.

Column 30,
Line 59, "application" should read -- Application --.
Line 59, "10/010110" should read -- 10/010,110 --.

Column 35,
Line 47, "may used" should read -- may be used --.
Line 49, "are is conveyed" should read -- are conveyed --.

Column 42,
Line 11, "to the pull" should read -- to pull --.
Line 23, "with other" should read -- with each other --.

UNITED STATES PATENT AND TRADEMARK OFFICE
CERTIFICATE OF CORRECTION

PATENT NO. : 6,888,143 B2
DATED : May 3, 2005
INVENTOR(S) : Vogt et al.

It is certified that error appears in the above-identified patent and that said Letters Patent is hereby corrected as shown below:

Column 45,
Line 39, "ct" should read -- of --.

Column 47,
Line 30, "engagement generally" should read -- engagement seam generally --.

Column 48,
Line 64, "let" should read -- set --.

Column 49,
Line 8, "therebetween" should read -- therebetween, --.

Column 52,
Line 55, "basic" should read -- back --.

Column 53,
Line 17, "suction" should read -- section --.
Line 43, "ocher" should read -- other --.

Column 54,
Line 25, "regions" should read -- region, --.

Column 55,
Line 59, "element," should read -- elements --.

UNITED STATES PATENT AND TRADEMARK OFFICE
CERTIFICATE OF CORRECTION

PATENT NO. : 6,888,143 B2
DATED : May 3, 2005
INVENTOR(S) : Vogt et al.

It is certified that error appears in the above-identified patent and that said Letters Patent is hereby corrected as shown below:

Column 56,
Line 27, "cut" should read -- out --.

Signed and Sealed this

Fourth Day of October, 2005

JON W. DUDAS
*Director of the United States Patent and Trademark Office*